(12) United States Patent
Chakravarty et al.

(10) Patent No.: US 9,505,725 B2
(45) Date of Patent: Nov. 29, 2016

(54) CRYSTALLINE AND MESOMORPHOUS FORMS OF AN AKT INHIBITING PYRIMIDINYL-CYCLOPENTANE COMPOUND, COMPOSITIONS AND METHODS THEREOF

(71) Applicant: Genentech, Inc., South San Francisco, CA (US)

(72) Inventors: Paroma Chakravarty, South San Francisco, CA (US); Sanjeev Kothari, South San Francisco, CA (US); Francis Gosselin, South San Francisco, CA (US); Scott J. Savage, South San Francisco, CA (US); Jeffrey Stults, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 15/018,636

(22) Filed: Feb. 8, 2016

(65) Prior Publication Data

US 2016/0152575 A1 Jun. 2, 2016

Related U.S. Application Data

(63) Continuation of application No. 14/401,092, filed as application No. PCT/US2013/041728 on May 17, 2013, now Pat. No. 9,290,458.

(60) Provisional application No. 61/648,536, filed on May 17, 2012.

(51) Int. Cl.
| | |
|---|---|
| *C07D 239/70* | (2006.01) |
| *A61K 31/496* | (2006.01) |
| *C07D 403/04* | (2006.01) |
| *A61K 31/517* | (2006.01) |

(52) U.S. Cl.
CPC ........... *C07D 239/70* (2013.01); *A61K 31/517* (2013.01); *C07D 403/04* (2013.01)

(58) Field of Classification Search
CPC . C07D 239/70; C07D 403/04; A61K 31/517
USPC .................... 514/252.16; 544/253
See application file for complete search history.

(56) References Cited

U.S. PATENT DOCUMENTS

| | | |
|---|---|---|
| 7,169,928 B2 | 1/2007 | Schwartz et al. |
| 8,063,050 B2 | 11/2011 | Mitchell et al. |
| 9,290,458 B2 | 3/2016 | Chakravarty et al. |
| 2005/0130954 A1 | 6/2005 | Mitchell et al. |
| 2011/0015204 A1 | 1/2011 | Bencsik et al. |
| 2011/0281844 A1 | 11/2011 | Schwartz et al. |
| 2012/0149684 A1 | 6/2012 | Beight et al. |
| 2014/0121193 A1 | 5/2014 | Katz et al. |
| 2015/0099880 A1 | 4/2015 | Babu et al. |
| 2015/0099881 A1 | 4/2015 | Lane et al. |
| 2015/0148559 A1 | 5/2015 | Remarchuk et al. |
| 2015/0152067 A1 | 6/2015 | Askin et al. |

FOREIGN PATENT DOCUMENTS

| | | |
|---|---|---|
| WO | 9515684 | 6/1995 |
| WO | 9844797 | 10/1998 |
| WO | 9856234 | 12/1998 |
| WO | 9961408 | 12/1999 |
| WO | 0052134 | 9/2000 |
| WO | 0122963 | 4/2001 |
| WO | 03063822 | 8/2003 |
| WO | 2004108673 | 12/2004 |
| WO | 2008006040 | 1/2008 |
| WO | 2009047255 | 4/2009 |
| WO | 2010120935 | 10/2010 |
| WO | 2012009649 | 1/2012 |
| WO | 2012040258 | 3/2012 |
| WO | 2012177925 | 3/2012 |
| WO | 2014127350 | 8/2014 |
| WO | 2014150395 | 9/2014 |

OTHER PUBLICATIONS

Bastin, et al., "Salt Selection and Optimisation Procedures for Pharmaceutical New Chemical Entities", Organic Process Research & Development 4, 427-435 (2000).
Haleblian, "Characterization of Habits and Crystalline Modification of Solids and Their Pharmaceutical Applications", Journal of Pharmaceutical Sciences, vol. 64 (8), 1269-1288 (1975).
Hancock, et al., "Characteristics and Significance of the Amorphous State in Pharmaceutical Systems", Journal of Pharmaceutical Sciences, vol. 86 (1), 1-12 (1997).
Llinas, et al., "Polymorph control: past, present and future", Drug Discovery Today, vol. 13 (5/6), 198-210 (2008).
Marques, et al., "Liquid-filled Gelatin Capsules", Pharmacopeia! Forum vol. 35 (4), 1029-1041 (2009).
Patent Cooperation Treaty, International Searching Authority, Search Report and Written Opinion for PCT/US2013/041728, 12 pages, Jul. 18, 2013.
Tadwee, et al., "Liquid Crystals Pharmaceutical Application: A Review", International Journal of Pharmaceutical Research & Allied Sciences, vol. 1 (2), 6-11 (2012).
Vippagunta, et al., "Crystalline solids", Advanced Drug Delivery Reviews 48, 3-26 (2001).
Yu, "Amorphous pharmaceutical solids: preparation, characterization and stabilization", Advanced Drug Delivery Reviews 48, 27-42 (2001).

(Continued)

*Primary Examiner* — Kristin Vajda
(74) *Attorney, Agent, or Firm* — Viksnins Harris & Padys PLLP

(57) ABSTRACT

Disclosed is (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride, forms, formulations, pharmaceutical compositions, processes of manufacturing and methods of use thereof.

17 Claims, 61 Drawing Sheets

CRYSTALLINE AND MESOMORPHOUS FORMS OF AN AKT INHIBITING PYRIMIDINYL-CYCLOPENTANE COMPOUND, COMPOSITIONS AND METHODS THEREOF

PRIORITY OF INVENTION

This application is a continuation of U.S. patent application Ser. No. 14/401,092 filed Nov. 13, 2014, which is a 35 U.S.C 371 national stage application of International Patent Application No. PCT/US2013/041728, filed May 17, 2013, which claims priority to U.S. Provisional Application No. 61/648,536, that was filed on May 17, 2012, which are incorporated herein by reference in their entirety.

FIELD OF INVENTION

Disclosed herein are forms and formulations of a pyrimidinylcyclopentane compound with therapeutic activity against diseases such as cancer and processes for making the same.

BACKGROUND OF INVENTION

The Protein Kinase B/Akt enzymes are a group of serine/threonine kinases that are overexpressed in certain human tumors. International Patent Application Publication Number WO 2008/006040 and U.S. Pat. No. 8,063,050 discuss a number of inhibitors of AKT, including the compound (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one (GDC-0068), which is being investigated in clinical trials for the treatment of various cancers. The free base and dihydrochloride salt form of GDC-0068 isolated in Example 14 of U.S. Pat. No. 8,063,050 are hygroscopic and difficult to develop into a solid dosage form. What is needed are forms and formulations of GDC-0068 and its salts that have improved pharmaceutical properties.

SUMMARY OF INVENTION

One aspect includes amorphous (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride (a compound of formula I), pharmaceutical compositions, formulations and a process of manufacturing thereof.

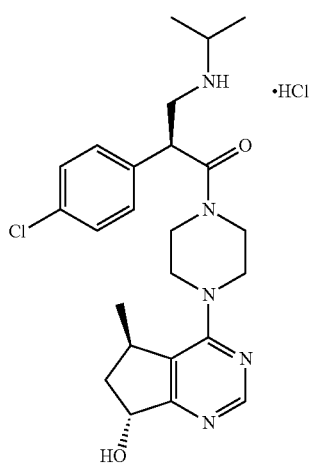

I

Another aspect includes a mesomorphous form of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)-propan-1-one monohydrochloride, pharmaceutical compositions, formulations and a process of manufacturing thereof.

Another aspect includes a condis crystalline form of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride, pharmaceutical compositions, formulations and a process of manufacturing thereof.

Another aspect includes crystalline forms of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride, pharmaceutical compositions, formulations and a process of manufacturing thereof.

Another aspect includes compositions comprising (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)-propan-1-one monohydrochloride and solvent, pharmaceutical compositions, formulations and a process of manufacturing thereof. In certain embodiments, the composition is a solid composition.

Another aspect includes compositions comprising solvates of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride, pharmaceutical compositions, formulations and a process of manufacturing thereof.

Another aspect includes a process of producing amorphous (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride, comprising spray drying a mixture comprising (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride or a solvate thereof and solvent.

Another aspect includes a process of producing amorphous (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride, comprising contacting a mixture comprising (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride or a solvate thereof with a gas, for example nitrogen and water.

Another aspect includes a tablet for oral delivery comprising amorphous (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride.

DESCRIPTION OF FIGURES

FIG. 1A shows an X-ray powder diffractometry (XRPD) pattern of a diffused halo, typical of amorphous material. FIG. 1B shows a polarized microscopy image. No birefringence was observed.

DETAILED DESCRIPTION OF INVENTION

Figure 1A:
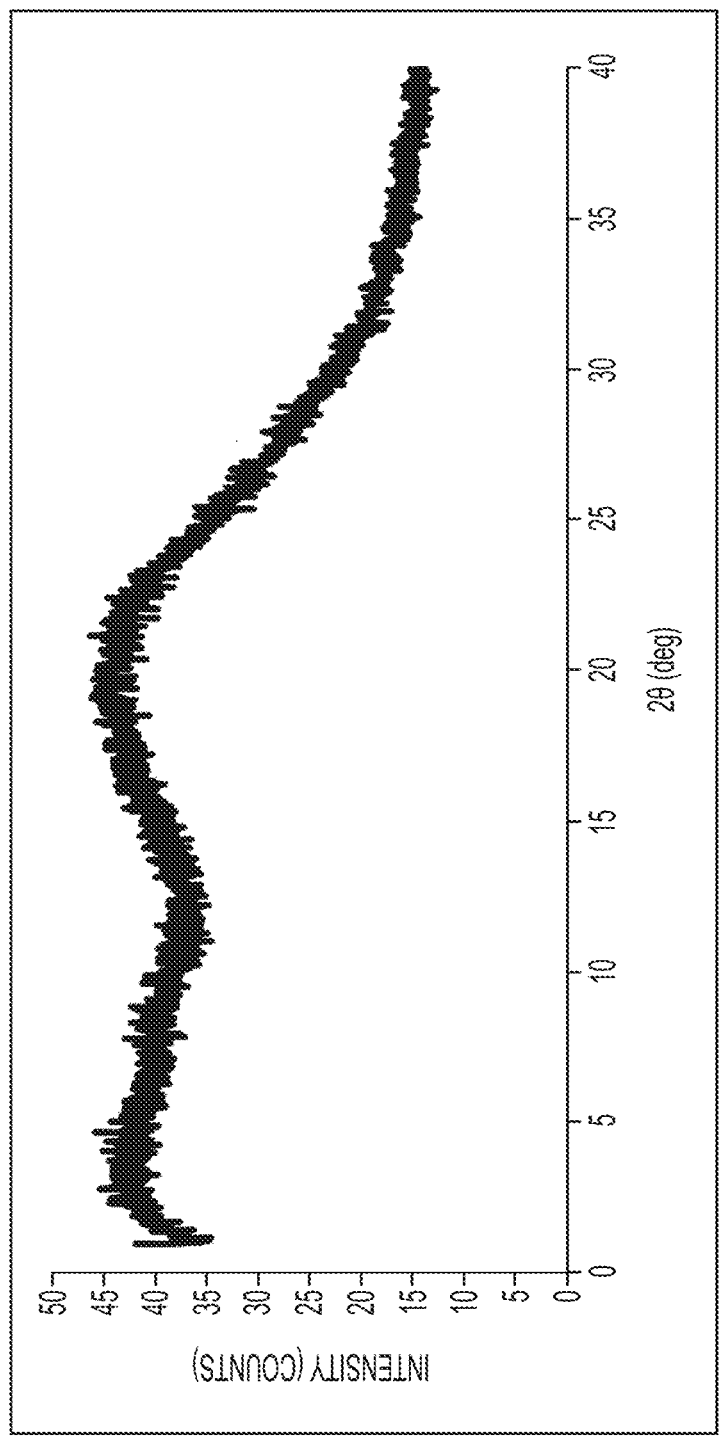
FIGS. 1A-B show physical characterization of amorphous form of compound of formula I.
Figure 1B:
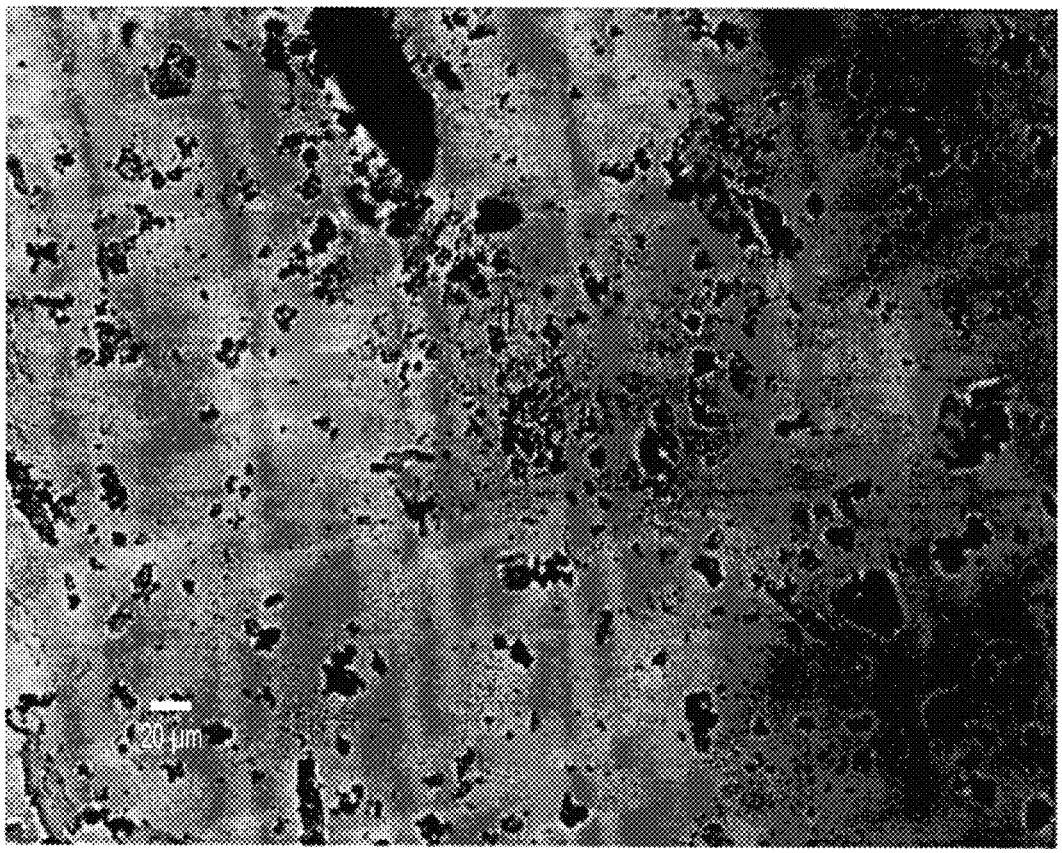
Figure 2:
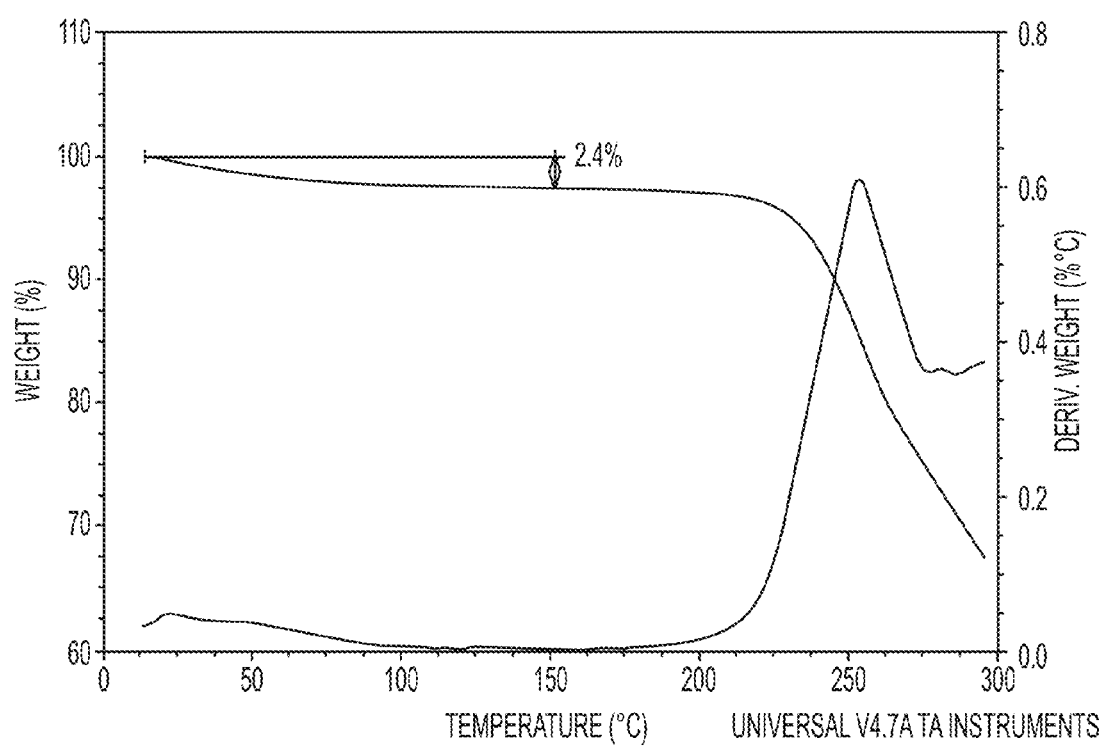
FIG. 2 shows a thermogravimetric analysis (TGA) profile of amorphous compound of formula I showing weight loss (due to presence of solvent: water and ethanol) up to 150° C.
Figure 3:
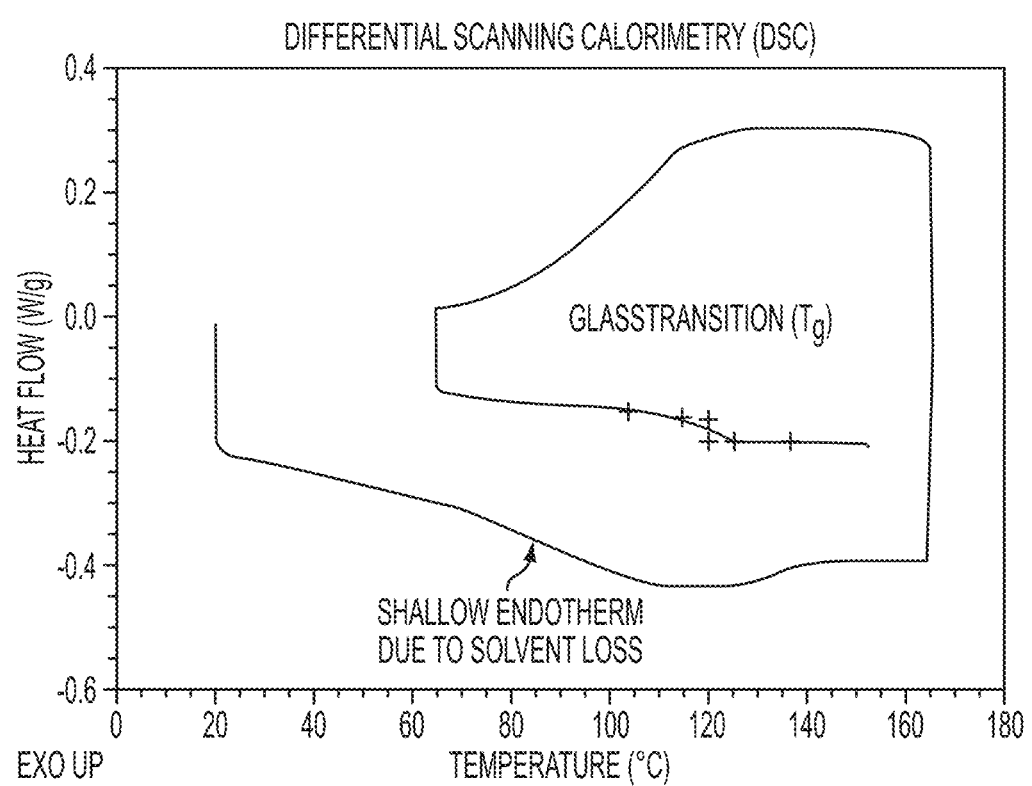
FIG. 3 shows a differential scanning calorimetry (DSC) profile of amorphous compound of formula I where glass transition is evident in the second heating cycle after solvent removal in the first heating cycle. Glass transition onset temperature for the sample is 114° C.
Figure 4:
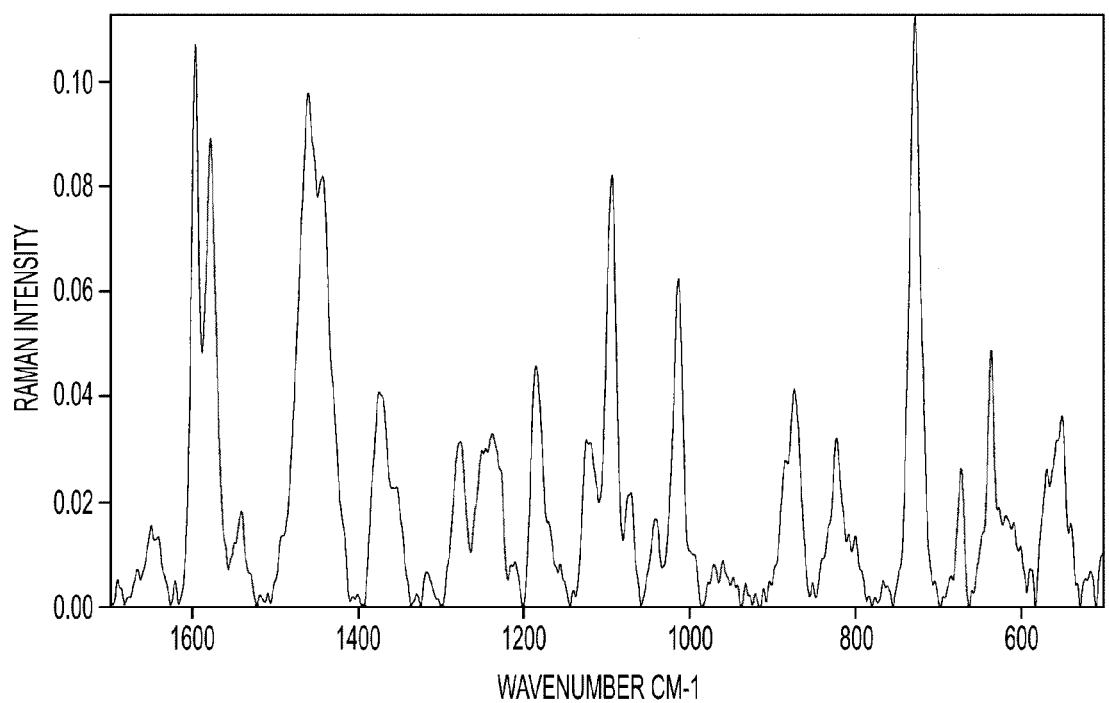
FIG. 4 shows a FT-Raman spectra of amorphous compound of formula I.

The term "a" as used herein means one or more.

Reference to "about" a value or parameter herein includes (and describes) embodiments that are directed to that value or parameter per se and in one embodiment plus or minus 20% of the given value. For example, description referring to "about X" includes description of "X".

"Pharmaceutically acceptable salts" include both acid and base addition salts. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, tromethamine, dicyclohexylamine, choline, and caffeine.

Compounds of the present invention, unless otherwise indicated, include compounds that differ only in the presence of one or more isotopically enriched atoms. For example, compounds of the present invention, wherein one or more hydrogen atoms are replaced by deuterium or tritium, or one or more carbon atoms are replaced by a $^{13}C$ or $^{14}C$ carbon atom, or one or more nitrogen atoms are replaced by a $^{15}N$ nitrogen atom, or one or more sulfur atoms are replaced by a $^{33}S$, $^{34}S$ or $^{36}S$ sulfur atom, or one or more oxygen atoms are replaced by a $^{17}O$ or $^{18}O$ oxygen atom are within the scope of this invention.

It has been unexpectedly discovered that isolating (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride (a compound of formula I) from particular solvents produces different physical forms of the compound, and that the different forms have different pharmaceutical properties. It has been found that certain forms have improved properties useful for formulating the compound into stable drug forms for treating diseases such as cancer.

One aspect includes a solid composition comprising a compound of formula I and solvent. Another aspect includes a crystalline solid composition comprising a compound of formula I and solvent. Example solvents for the solid composition include capryol glycol, lauryl glycol, MEK, MIBK, MTBK, chloroform, dichloromethane, ethyl acetate, toluene, chlorobenzene, ethylbenzene, THF, 2-MethylTHF, 1,2-dichloroethane, ortho-xylene, meta-xylene, para-xylene, anisole, methyl acetate, cumene, tetralin, propyl acetate, isopropyl acetate, diisobutyl ketone, isobutyl acetate, t-butyl acetate, amyl acetate, glycerol triacetate, 1,2-dimethoxyethane, 1,2-diethoxyethane, 2,2-dimethoxypropane, ethyl ether, t-butyl methyl ether, water and mixtures thereof (including ether-ethanol mixture). In certain embodiments, the solid composition comprises variable levels of solvent. In certain embodiments, the solid composition comprises solvent solvated to the compound of formula I. Example solvates of the solid composition include channel or layered solvates. In one example, the solid composition comprises compound of formula I, fully substituted with solvent, such as 1:1 molar ratio solvate. In another example, the solid composition comprises compound of formula I, partially substituted with solvent, such as in a w/w % (solvent:compound of formula I) in the range of about 0.1% to about 20%, alternatively about 1% to about 15%. In one specific example, a solid composition comprises a compound of formula I and ethyl acetate in a ratio of about 16% to about 1% ethyl acetate.

Another aspect includes a mesomorphous form of compound of formula I comprising intermediate order, which results from crystallizing the compound of formula I from a solvent mixture comprising antisolvent.

Another aspect includes a condis crystalline form of compound of formula I that has intermediate order, resulting from crystallizing from a solvent mixture comprising antisolvent.

Another aspect includes an amorphous form of compound of formula I that results from isolating from solvent. The amorphous form has certain improved pharmaceutical properties and can be formulated into stable drug forms for treating diseases such as cancer.

Therefore, one aspect includes amorphous (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride (a compound of formula I).

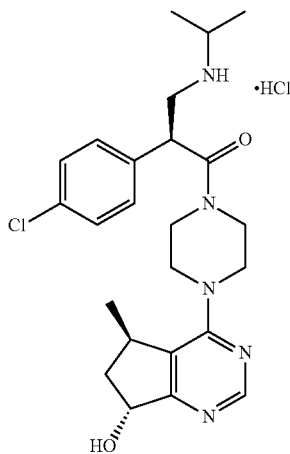

I

Another aspect includes a liquid-fill capsule formulation of compound of formula I, comprising a compound of formula I and a liquid fill solvent. Liquid fill solvents for use in the liquid fill formulations include solvents that comprise a lipidic (for example, $C_{3\text{-}20}$ alkyl) group and hydroxyl group. In one example, liquid fill solvents are mono-esters, di-esters and tri-esters of fatty acids ($C_{3\text{-}20}$ alkyl or $C_{8\text{-}18}$ alkyl) and glycerol, ethylene glycol, propylene glycol or polyethylene glycol. Examples include lipids, such as glyceryl stearates, for example esters of natural fatty, stearic and palmitic acids with glycerin, and alkylglycol caprylates, and the like. Other examples include propylene glycol monocaprylate type II (Capryol 90™), PEG-32 glyceryl laurate-(Gelucire® 44/14), Propylene glycol monocaprylate type I (Imwitor 792), PEG-6 glyceryl oleate, (Labrafil® M 1944CS), PEG-6 glyceryl linoleate, (Labrafil® M 2125 CS), Propylene glycol monolaurate type II, (Lauroglycol 90), Poloxamer 188, (Lutrol F68NF), Poloxamer 407, (Lutrol F127 NF), Polyethyleneglycol (PEG)1500, Propylene glycol, Glycerol (Glycerin), d-alpha tocopheryl PEG-1000 succinate, (VitaminE-TPGS), PEG-8 caprylic/capric glycerides (Labrasol®), and esters of caprylic or capric fatty acids with glycerin or propylene glycol (for example, Miglyol 810N or Miglyol 812N).

In another example, liquid fill solvents are those solvents with critical micelle concentration (cmc) values greater than about 0.9 g/g with the compound of formula I. In certain embodiments, the liquid fill solvent is propylene glycol caprylate (in one example, the product sold commercially as Capryol 90™, Gattefosse). The liquid fill solvent can be present in a range of about 36.5% w/w to about 60% w/w depending on the dosage strength, i.e., the amount of compound of formula I. In another example, the liquid fill solvent is a solvent in which the compound of formula I can be dissolved in concentrations between about 0.7 and 1 g/g, including propylene glycol monocaprylates (e.g., types I and II), PEG-8 caprylic/capric glycerides, glycyl laurate (for example Lauroglycol™), glycerol, propylene glycol and PEG-8 caprylic/capric glycerides.

In certain embodiments, the liquid fill solvent is selected from liquid fill solvents described herein that are further compatible with hydroxypropylmethyl cellulose and hard gelatin capsules such as propylene glycol monocaprylate type II (Capryol 90™) and Lauroglycol™ 90.

In certain embodiments, the liquid-fill formulation further comprises an antioxidant. Antioxidants include ascorbic acid, methionine, butylated hydroxyanisole (BHA) and butylated hydroxytoluene (BHT). In one example, the antioxidant comprises BHA. In one example, the antioxidant comprises BHT. In certain embodiments, the liquid fill formulation comprises about 0.1% w/w antioxidant.

In certain embodiments, the liquid-fill formulation further comprises anti-crystallization additives. In one example, the additive is PVP polymer.

The liquid-fill formulation allows for unexpectedly high concentrations of compound of formula I, which allows for the production of a single, high dosage unit with strengths between 100-mg and 400-mg. Such high doses are generally unachievable with active pharmaceutical ingredients in the lipid like liquid fill solvent systems. For example, it was unexpectedly discovered that compound of formula I is surface active in the presence of propylene glycol caprylate which provides the ability to reach high concentration liquid fill formulations. The critical micelle concentration for GDC-0068 in propylene glycol caprylate (e.g., Capryol 90™) was determined to be 0.945 g/g.

Additionally, several compounds with known high aqueous solubility as well as poor aqueous solubility were tested for the maximum amounts that could be dissolved in Capryol 90™. Highly water-soluble compounds tested were ascorbic acid, metformin, acetyl salicylic acid and acetaminophenol. Poorly water-soluble compounds tested were griseofulvin, indomethacin and naproxen. None of the model compounds could be dissolved at greater than 10% w/w concentration in Capryol 90™.

Therefore, another aspect includes a liquid fill formulation of a compound of formula I, comprising about 100 mg to about 400 mg of compound of formula I (measured as free base), about 36.5% w/w to about 60% w/w propylene glycol caprylate and about 0.1% w/w antioxidant. In one example, the antioxidant is BHA. In one example, a liquid-fill formulation comprises 100 mg compound of formula I. In one example, a liquid-fill formulation comprises 400 mg compound of formula I. In one example, the formulation further comprises a capsule.

Another aspect includes a tablet formulation, comprising amorphous compound of formula I and filler. In one example, the formulation comprises amorphous compound of formula I and silica. In another example, the formulation further comprises inhibitors of crystallization, such as PVP or hydroxypropyl methylcellulose (HPMC), and optionally further comprises antioxidant. such as BHT or BHA.

In certain embodiments, the tablet comprises about 33% w/w amorphous compound of formula I, about 15% w/w silica (in one example, the product sold commercially as Cab-o-sil, Cabot, Corp.), about 43% w/w microcrystalline cellulose, about 5% w/w croscarmellose sodium, about 2.5% w/w PVP, about 0.1% w/w BHA, and about 1% w/w stearic acid.

Another aspect includes a process of producing amorphous compound of formula I, comprising contacting a compound of formula I with a solvent, and removing the solvent to form the amorphous compound of formula I.

Alternatively, the process of producing amorphous compound of formula I comprises removing solvent from a solvate of a compound of formula I, such as by drying or contacting the solvate with moist nitrogen or other inert gas.

Alternatively, the process of producing amorphous compound of formula I comprises spray drying a solution of compound of formula I to form amorphous material. In one example of spray drying, the material (for example crystalline or mesomorphous material) is dissovled in a solvent and spray dried to produce the amorphous compound of formula I. Example solvents for use in the spray drying process include water and ethanol. The starting material can be any form of the compound of formula I, for example, a solvate of a compound of formula I, such as the ethyl acetate solvate, or material prepared according to Example 1. In one example, the spray dried amorphous product comprises about 0.01 to about 2.5% residual solvent. In one example, the spray dried amorphous product comprises about 0.01 to about 1.0% residual solvent. In one example, the ethyl acetate solvate is contacted with water and spray dried to give amorphous compound of formula I comprising less than about 1.0% w/w water and about 0.25% w/w or less ethyl acetate. In another example, the ethyl acetate solvate is contacted with ethanol and spray dried to give amorphous compound of formula I comprising less than about 1.0% w/w water, about 2.5% w/w or less ethanol and about 0.25% w/w or less ethyl acetate. In certain embodiments, the process further comprises drying the spray-dried amorphous material to further reduce the amount of water and solvent. In one example, the further dried amorphous spray-dried compound of formula I comprises less than about 0.5% solvent.

In certain embodiments, the contacting of a compound of formula I with a solvent further comprises dissolving the compound of formula I in the solvent. In certain embodiments, the solvent comprises ethanol. In one example, the solvent comprises water. In certain embodiments the solvent comprises ethanol:water, for example in 1:1 mixture. In certain embodiments, the solvent further comprises additives, for example, inhibitors of crystallization, such as polymers, for example polyvinylpyrrolidone (PVP), and other additives, such as antioxidants or preservatives, for example, BHA or BHT.

Another aspect includes a pharmaceutical formulation comprising an amorphous compound of formula I.

Another aspect includes a process of producing a tablet formulation comprising amorphous compound of formula I, comprising contacting a compound of formula I with a solvent comprising ethanol to form a mixture; contacting the mixture with filler comprising crystalline cellulose; and removing the solvent to form the pharmaceutical formulation comprising amorphous compound of formula I. In certain embodiments, the solvent further comprises water. In certain embodiments, the solvent further comprises stabilizer, for example, PVP polymer, and antioxidant, for example BHA or BHT.

Another aspect includes a process of producing a tablet formulation comprising contacting a mesomorphous form of a compound of formula I, cellulose and silica (for example amorphous or colloidal silica). The process includes contacting the mesomorphous form, cellulose and silica with a solvent mixture of ethanol and water and removing the solvent mixture by drying the mixture to form the amorphous form of the compound of formula I, which is entrapped in the mixture. It was unexpectedly found that such a direct wet granulation process would result in an amorphous form of the drug substance of formula I. The hygroscopicity of the final formulation obtained by such a direct wet granulation is surprisingly similar to that of the formulation prepared from a solution mediated precipitation of the compound of formula I alone.

In certain embodiments, the tablet manufacturing process includes (a) dissolving antioxidant and stabilizer in a 50:50 mixture of solvent comprising ethanol, and optionally further comprising water to form a mixture; (b) dissolving compound of formula I into the mixture to form a solution; (c) granulating the solution with filler to form granules; (d) drying the granules; and (e) compressing the granules to produce the tablet. In one example, the process further comprises before (e): mixing additional ingredients to form a blend.

In certain embodiments, the granulating process further comprises high-shear granulating the solution with filler comprising crystalline cellulose. In certain embodiments, the filler comprises microcrystalline cellulose. In certain embodiments, the filler further comprises fumed amorphous silica, and optionally further comprises croscarmellose sodium. In one example, the filler comprises highly porous microcrystalline cellulose and fumed silica.

In certain embodiments, drying the granules further comprises drying at an elevated temperature. In certain embodiments, the temperature for drying granules is in the range of about 50° C. and 60° C.

Predicting and controlling the amount of crystallinity in a drug dosage form is important for several reasons including obtaining predictable bioavailability and quality control in manufacturing. It is also important to have stable drug forms of hygroscopic drug substances to prevent the drug forms from changing crystalline nature. Mesomorphous forms of a compound of formula I, for example, a condis-crystal form of the compound of formula I, can have analytically variable levels of crystallinity and is hygroscopic. The tablet production process described herein can transform a sample of compound of formula I from a mesomorphous form, and in one embodiment a condis-crystal form, to a drug product comprising amorphous compound of formula I, and mitigates hygroscopicity problems (i.e., deliquescence) by adsorbing the compound of formula I into a highly porous structure of filler (for example, fumed silica) and thereby protecting the compound of formula I from the moisture gain.

Another aspect provides a solid unit oral pharmaceutical dosage form comprising amorphous compound of formula I in an amount of 100 mg to 400 mg calculated as the freebase form, and pharmaceutically acceptable carrier, diluent, stabilizer or excipient. In certain embodiments, the solid unit oral pharmaceutical dosage form comprises amorphous compound of formula I in an amount of 100 mg. In certain embodiments, the solid unit oral pharmaceutical dosage form comprises amorphous compound of formula I in an amount of 400 mg. In certain embodiments, the oral dosage form is a tablet.

Another aspect includes a mesmorphous form of the compound of formula I. Another aspect includes a condis-crystal form of the compound of formula I.

Another aspect includes a process of producing mesomorphous form of compound of formula I, comprising contacting a compound of formula I with a solvent comprising antisolvent, for example, ethyl acetate, and removing the solvent to form the mesomorphous compound of formula I. In one example, the mesomorphous form is a condis-crystalline form. In certain embodiments, the solvent further comprises an alcohol, for example isopropanol. In certain embodiments the solvent comprises ethyl acetate:isopropanol in 1:1 mixture.

Antisolvents for the compound of formula I include liquids in which the compound of formula I has solubility less than about 20 mg/mL. In one example, antisolvents include pentane, hexane, cyclohexane, heptane, ethyl acetate, iso-propyl acetate, methyl t-butyl ether (MTBE) and methyl iso-butyl ketone.

Solvents for the compound of formula I include liquids in which the compound of formula I has solubility greater than about 20 mg/mL. In one example, solvents include water, alcohols such as methanol, ethanol, isopropanol, 2-butanol, t-butanol and 2-methoxy ethanol, polar ethers such as tetrahydrofuran and 2-methyltetrahydrofuran, toluene, chloroform, dichloromethane, 1,2-dichloroethane and acetone.

Another aspect includes a pharmaceutical formulation comprising a solid composition comprising compound of formula I and solvent. Another aspect includes a pharmaceutical formulation comprising mesomorphous form of compound of formula I. Another aspect includes a pharmaceutical formulation comprising condis-crystal form of compound of formula I.

Another aspect includes a process of producing a pharmaceutical formulation comprising mesomorphous compound of formula I, comprising contacting a compound of formula I with a solvent comprising antisolvent, for example, ethyl acetate to form mesomorphous compound of formula I.

Another aspect includes a process of producing a pharmaceutical formulation comprising condis-crystalline compound of formula I, comprising contacting a compound of formula I with a solvent comprising antisolvent, for example, ethyl acetate to form condis-crystalline compound of formula I.

Another aspect includes crystalline solvate of compound of formula I, wherein the compound of formula I forms a crystalline solvate with solvent selected from glyceryl capyrlate, glycol laurate, methyl ethyl ketone (MEK), methyl iso-butyl ketone (MIBK), methyl tert-butyl ketone (MTBK), chloroform, dichloromethane, ethyl acetate, toluene, tetrahydrofuran (THF), 2-Methyltetrahydrofuran (2-MeTHF), 1,2-dichloroethane, meta-xylene, anisole, methyl acetate, cumene, isopropyl acetate, diisobutyl ketone, isobutyl acetate, amyl acetate, and mixtures thereof (including ether-ethanol mixture). In certain embodiments, the solvate further comprises water. In certain embodiments, the water forms a hydrate with the compound of formula I or with the solvated compound of formula I, for example chloroform solvate hydrate and ethanol-ether hydrate.

Another aspect includes crystalline solvate of compound of formula I, wherein the compound of formula I forms a crystalline solvate with solvent selected from capryol glycol, lauryl glycol, MEK, MIBK, MTBK, chloroform, dichloromethane, ethyl acetate, toluene, chlorobenzene, ethylbenzene, THF, 2-MethylTHF, 1,2-dichloroethane, ortho-xylene, meta-xylene, para-xylene, anisole, methyl acetate, cumene, tetralin, propyl acetate, isopropyl acetate, diisobutyl ketone, isobutyl acetate, t-butyl acetate, amyl acetate, glycerol triacetate, 1,2-dimethoxyethane, 1,2-diethoxyethane, 2,2-dimethoxypropane, ethyl ether, t-butyl methyl ether and mixtures thereof (including ether-ethanol mixture). In certain embodiments, the solvate further comprises water. In certain embodiments, the water forms a hydrate with the compound of formula I or with the solvated compound of formula I, for example chloroform solvate hydrate and ethanol-ether hydrate.

Another aspect includes solid compositions comprising a compound of formula I and solvent selected from capryol glycol, lauryl glycol, MEK, MIBK, MTBK, chloroform, dichloromethane, ethyl acetate, toluene, THF, 2-MethylTHF, 1,2-dichloroethane, meta-xylene, anisole, methyl acetate, cumene, isopropyl acetate, diisobutyl ketone, isobutyl acetate, amyl acetate and mixtures thereof (including ether-ethanol mixture). In certain embodiments, the compositions comprising the solvate further comprise water. In certain embodiments, the water forms a hydrate with the compound of formula I or with the solvated compound of formula I. In certain embodiments, the solvent is solvated with compound of formula I.

Another aspect includes compositions comprising a compound of formula I and solvent selected from capryol glycol, lauryl glycol, MEK, MIBK, MTBK, chloroform, dichloromethane, ethyl acetate, toluene, THF, 2-MethylTHF, 1,2-dichloroethane, meta-xylene, anisole, methyl acetate, cumene, isopropyl acetate, diisobutyl ketone, isobutyl acetate, amyl acetate, chlorobenzene, ethylbenzene, ortho-xylene, THF, 2-MethylTHF, 1,2-dichloroethane, ortho-xylene, meta-xylene, para-xylene, tetralin, propyl acetate, t-butyl acetate, glycerol triacetate, 1,2-dimethoxyethane, 1,2-diethoxyethane, 2,2-dimethoxypropane, ethyl ether, t-butyl methyl ether and mixtures thereof (including ether-ethanol mixture). In certain embodiments, the compositions comprising the solvate further comprise water. In certain embodiments, the water forms a hydrate with the compound of formula I or with the solvated compound of formula I. In certain embodiments, the solvent is solvated with compound of formula I.

In certain embodiments, the compound of formula I forms a crystalline solvate with solvent selected from Capryol glycol and lauryl glycol.

EXAMPLE 1

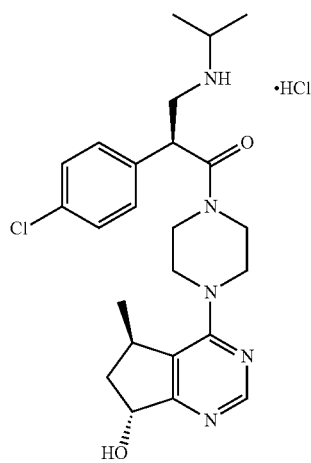 [SMILES: CC(C)NC[C@@H](C(=O)N1CCN(c2ncnc3c2[C@H](C)C[C@H]3O)CC1)c1ccc(Cl)cc1 ; Cl]

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride To a 500 mL reactor was added tert-butyl((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)(isopropyl)carbamate (49 g) and IPA (196 mL) and the reactor was heated to 50° C. A solution of HCl in 2-propanol (3M, 90 mL) was added to maintain the temperature from 50-70° C. The solution was maintained at 60° C. for 19 hours and the mixture was cooled to 0-5° C. Amberlyst A-21 resin (60.5 g) was washed with water (50 mL) and purged with N2 for 5 min to remove excess water. The resin was then washed with 2-propanol (50 mL) and purged with N2 for 5 min to remove excess 2-propanol. The reaction mixture was re-circulated through the packed resin bed for at least 2 hours until pH 3.55-7.0 was reached. The resin bed was purged with N2 for 5 min, collecting all the filtrates. The resin was washed with 2-propanol (294 mL), and the resin was purged with nitrogen for 5 min, combining all the filtrates. To the combined solution was added decolorizing charcoal (20 g) and the mixture was stirred at 15-25° C. for 1-2 hours. The charcoal was then filtered through diatomaceous earth and the solution was distilled under vacuum at 25-35° C. Ethyl Acetate (333.0 mL) was charged to obtain a ~87.5:12.5 EtOAc:IPA ratio. A seed slurry (1 g) of(S)-2-(4-chlorophenyl)-1-(4-((5R,7R)-7-hydroxy-5-methyl-6,7-dihydro-5H-cyclopenta[d]pyrimidin-4-yl)-3-(isopropylamino)propan-1-one monohydrochloride in EtOAc:IPA (~6 mL, 87.5:12.5) was added to the reactor and the mixture was stirred at 20-25° C. for 1 hour. The slurry was constant volume solvent-switched to EtOAc at 20-30° C. until a ratio of EtOAc:IPA≥97:3 was reached. The reactor was cooled to 0-10° C. and the slurry was filtered. The filter cake was washed with EtOAc (115 mL). Dried under vacuum at 85° C. for 16 hours to afford (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride as an off-white solid: 41.9 g (94% yield).

Figure 5:
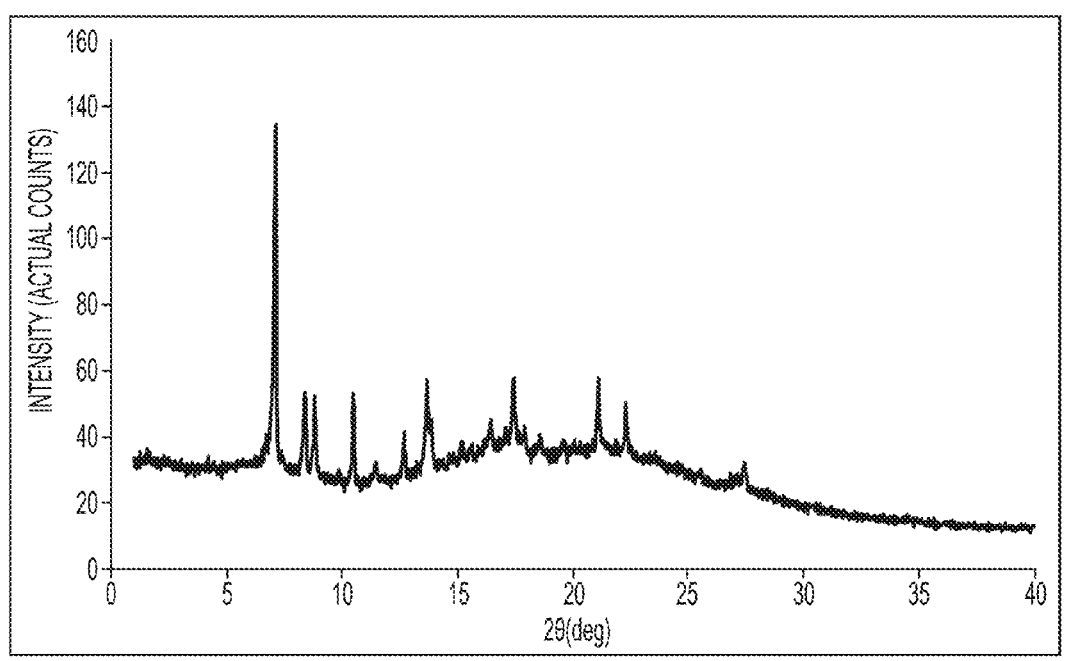
FIG. 5 shows an XRPD pattern of the product of Example 1, which shows both diffracted peaks and amorphous halo demonstrating by XRPD.
Figure 6:
FIG. 6 shows a polarized light microscopy image of the product of Example 1, where birefringence is observed.
Figure 7:
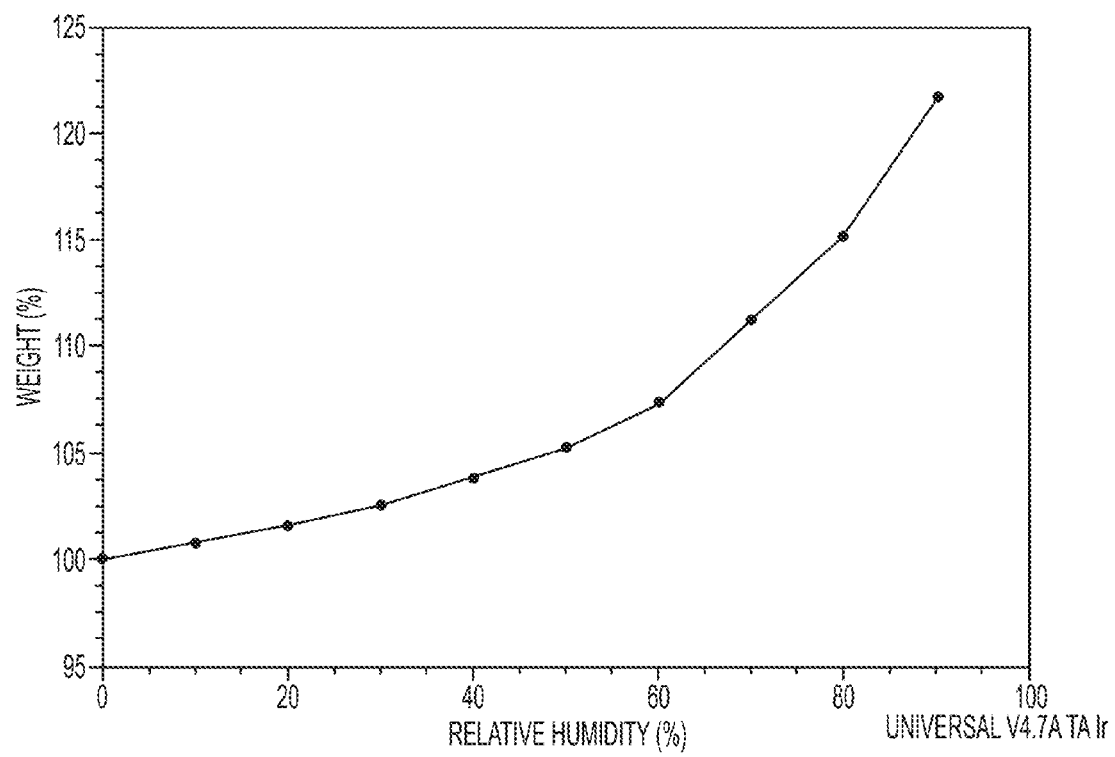
FIG. 7 shows a water sorption analysis of the product of Example 1, with continuous water sorption profile at 25° C. from 0-90% RH (deliquescence point at ~75% RH).
Figure 8:
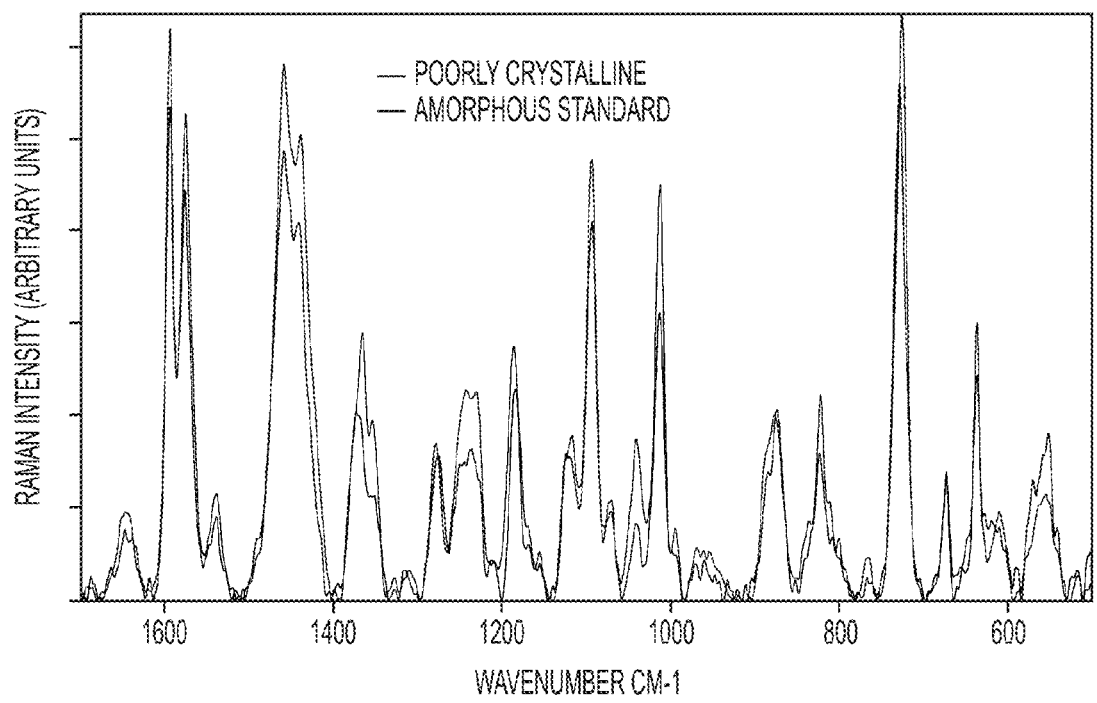
FIG. 8 shows a FT-Raman spectra of the product of Example 1, overlaid with amorphous form of compound of formula I.
Figure 9:
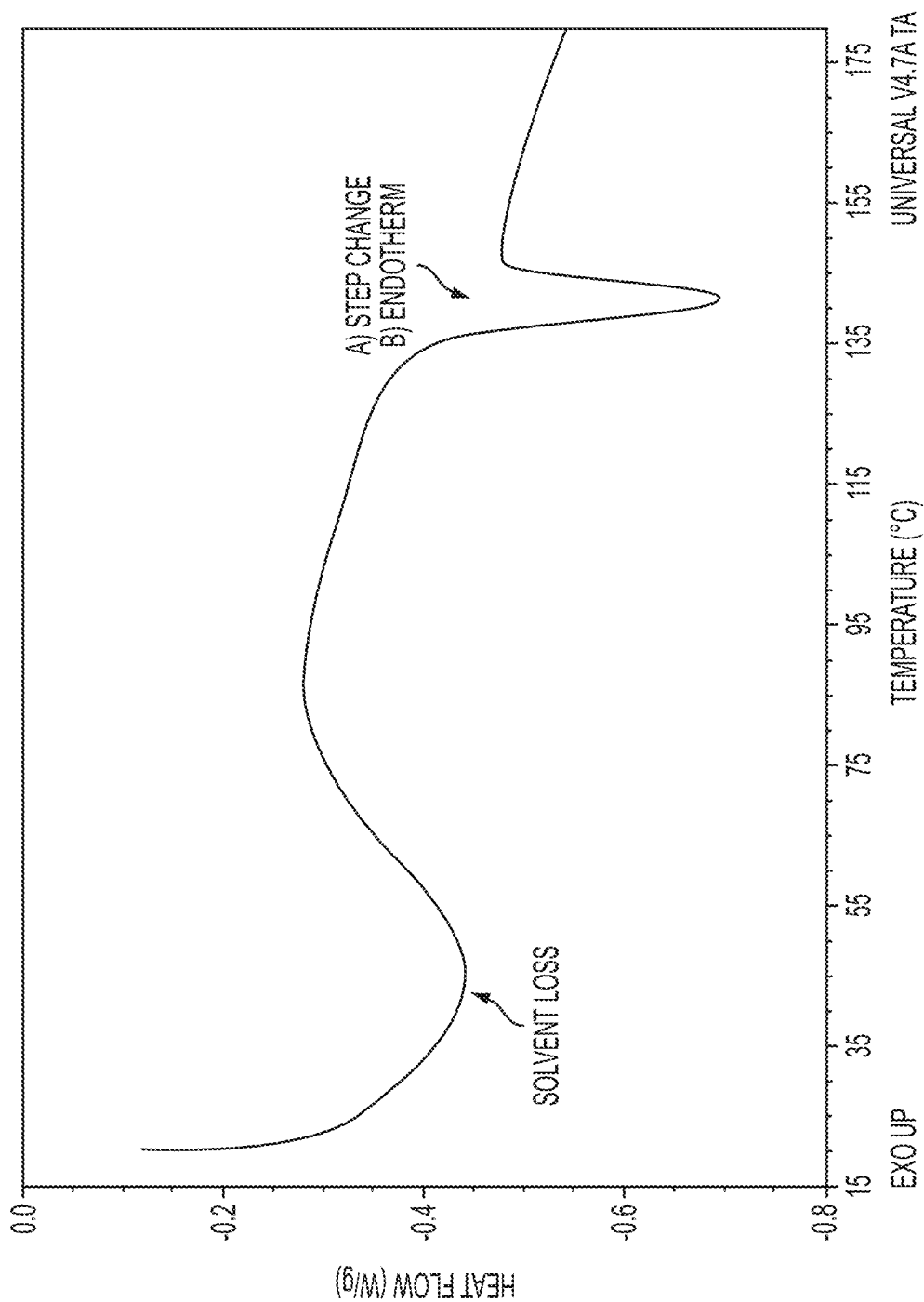
FIG. 9 shows a DSC profile of the product of Example 1. The first endotherm signifies solvent loss (water and ethanol). The second, sharp endotherm overlaps with a "step change" (change in baseline) event. To resolve these two events, a temperature modulation (±0.5° C. over 80 sec) was used, and the endotherm (with an associated enthalpy change of 7-11 J/g) was found to overlap with a glass transition temperature (onset ~130° C.).
Figure 10:
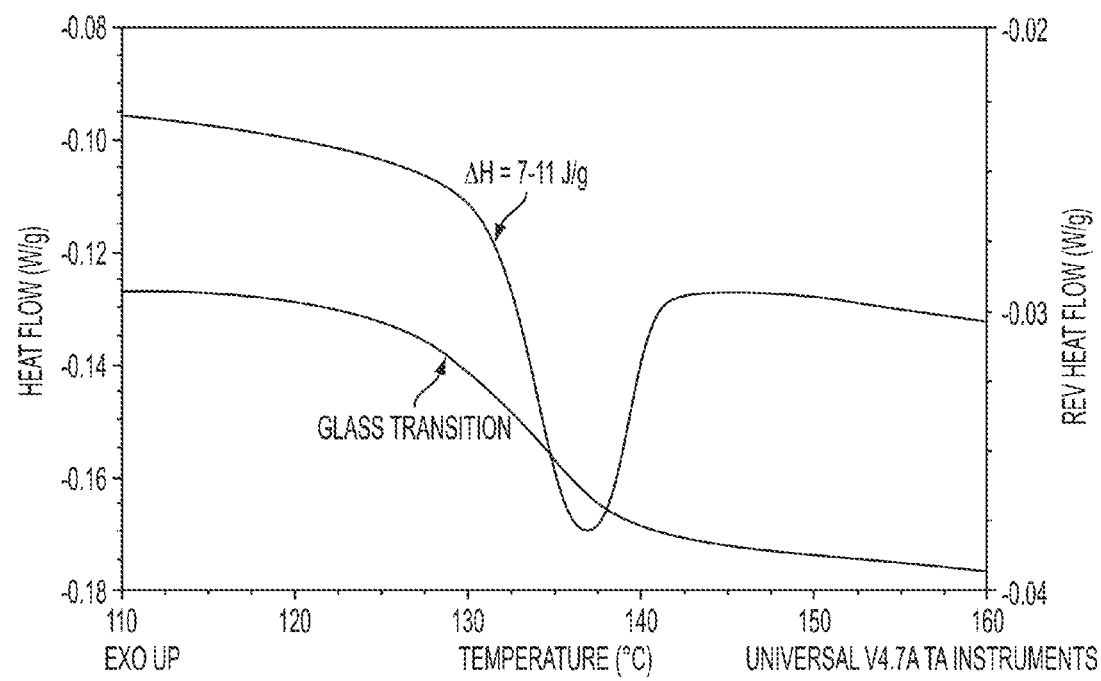
FIG. 10 shows a modulated DSC profile of the second endotherm of FIG. 9.
Figure 11:
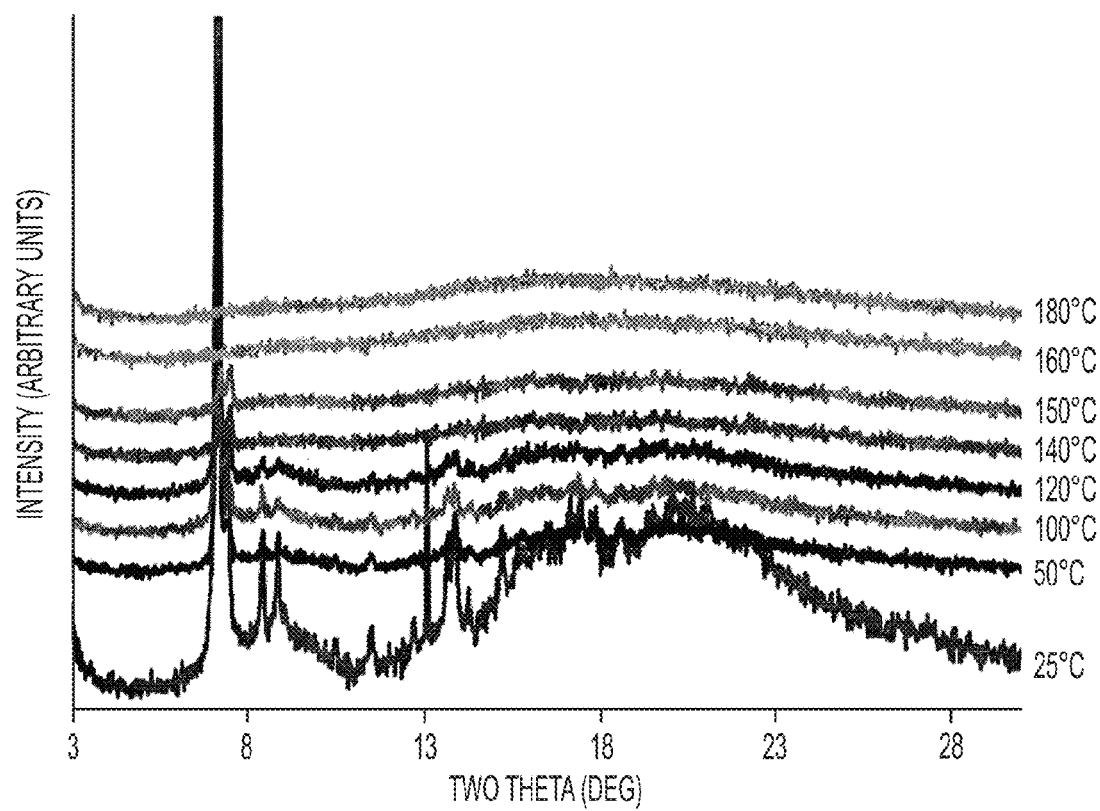
FIG. 11 shows various XRPD patterns as a function of temperature. Heating the the product of Example 1 leads to loss in structure (diffracted peaks start to disappear in the 100-160° C. range) and the solid-state form becomes amorphous.
Figure 12:
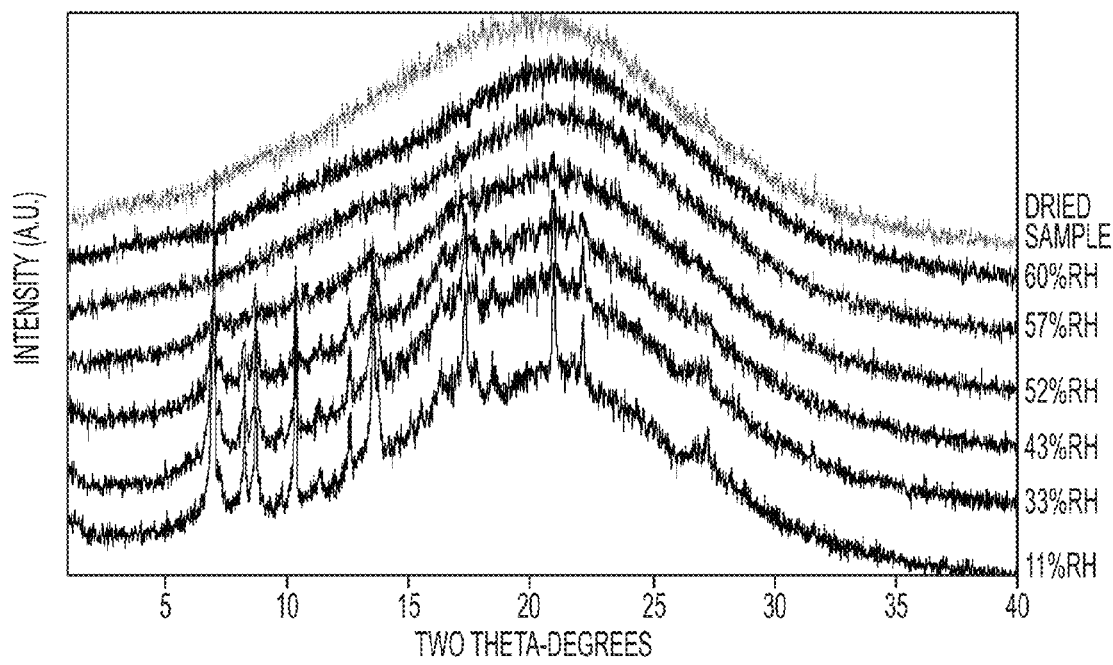
FIG. 12 shows various XRPD patters as a function of exposure to water vapor (relative humidity or RH) of the product of Example 1. Upon exposure to water vapor at room temperature (different RH/relative humidity conditions generated by using different salt solutions) for 5-7 days, the starting material loses crystallinity as suggested by loss of diffracted peak intensity as a function of increasing RH. Upon drying the sample exposed to 60% RH for 4 hours under reduced pressure (top most XRPD pattern), the crystallinity does not reappear.
Figure 13:
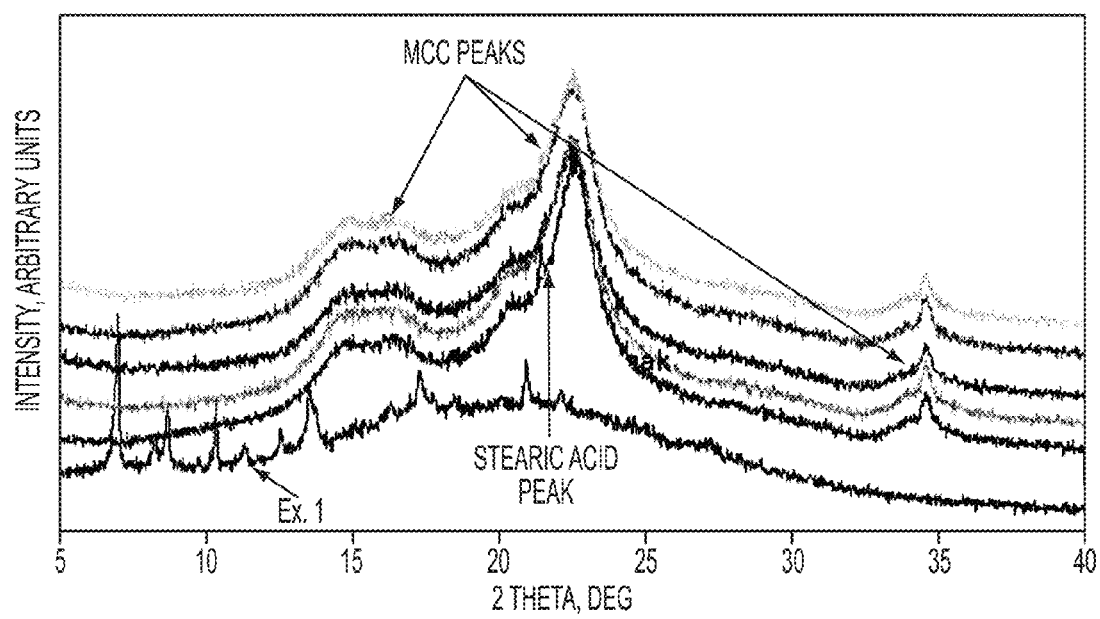
FIG. 13 shows representative XRPD patterns of the product of Example 1, (bottom) compared to granules of amorphous form of compound of formula I (prepared according to processes described herein) stored under ICH guidelines for 12 weeks. Diffracted peaks from crystalline regions are not present in the XRPD patterns of the granules of the amorphous form of formula I in the formulations described herein.
Figure 14:
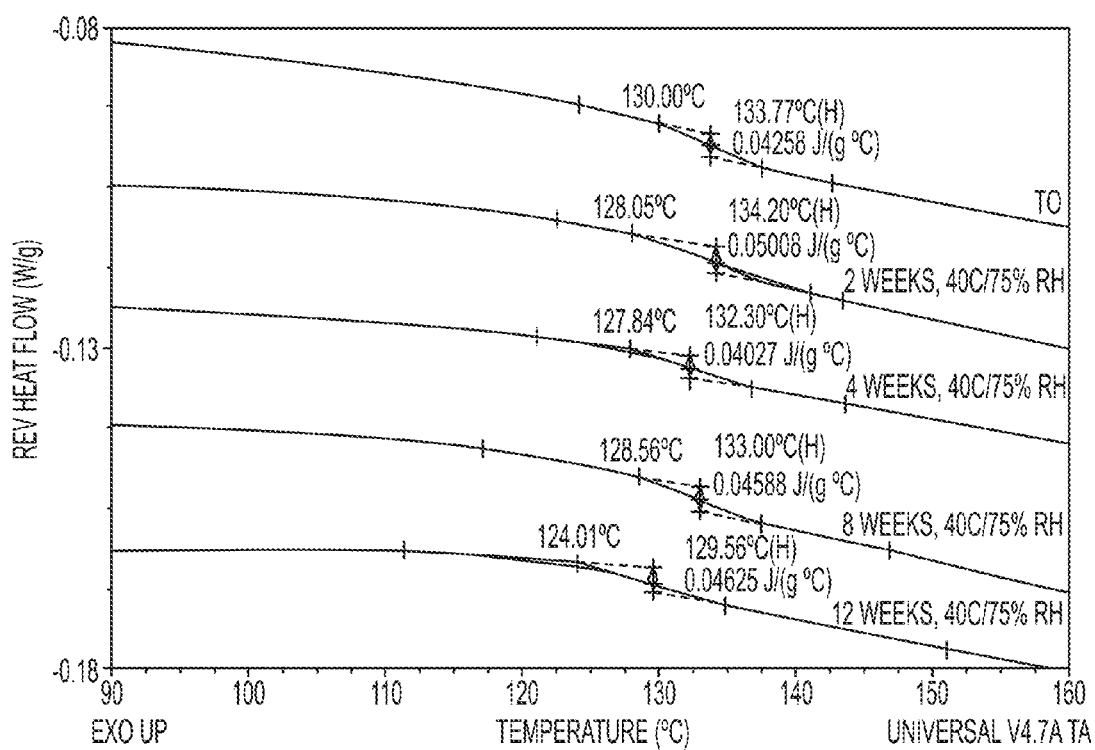
FIG. 14 shows DSC profiles of formulations comprising amorphous compound of formula I prepared as described herein. The profiles show consistent Tg of 124-130° C. (onset) over 12 weeks of storage for the formulation. The water content of granules stays between 3.5-4.5% (To water content=3.5-4%).
Figure 15:
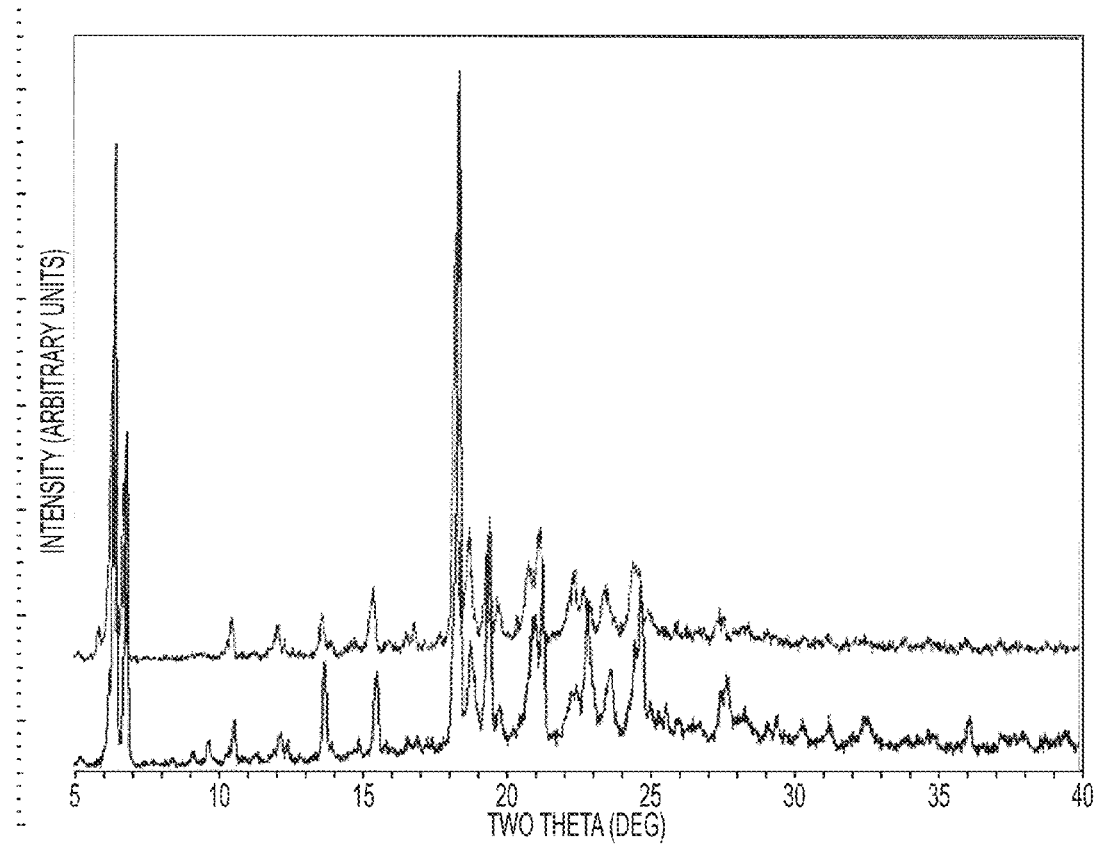
FIG. 15 shows XRPD profiles of two solvates of compound of formula I (glyceryl capyrlate top, glyceryl laurate bottom).
Figure 16:
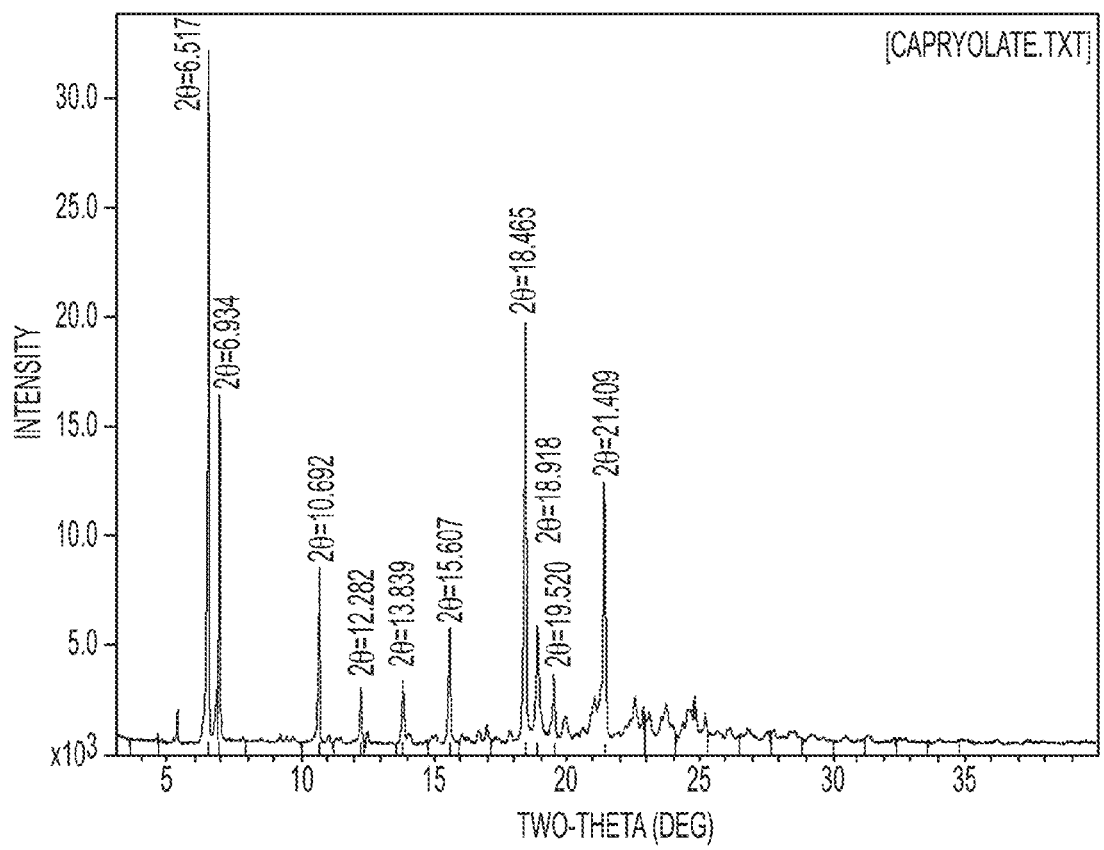
FIG. 16 shows variable temperature XRPD patterns of glyceryl capyrlate (Capryol 90™ solvate) of compound of formula I.
Figure 17:
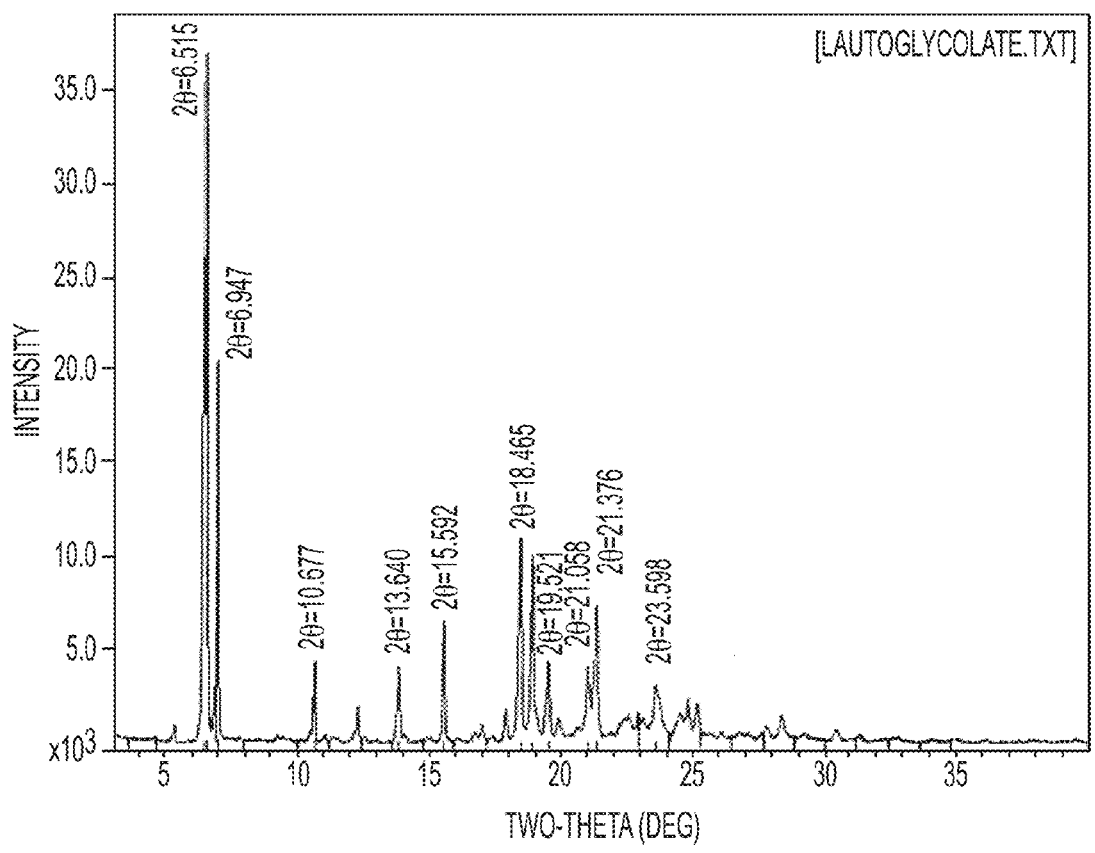
FIG. 17 shows variable temperature XRPD patterns of glyceryl laurate (Laurylglycol 90™ solvate) of compound of formula I.
Figure 18:
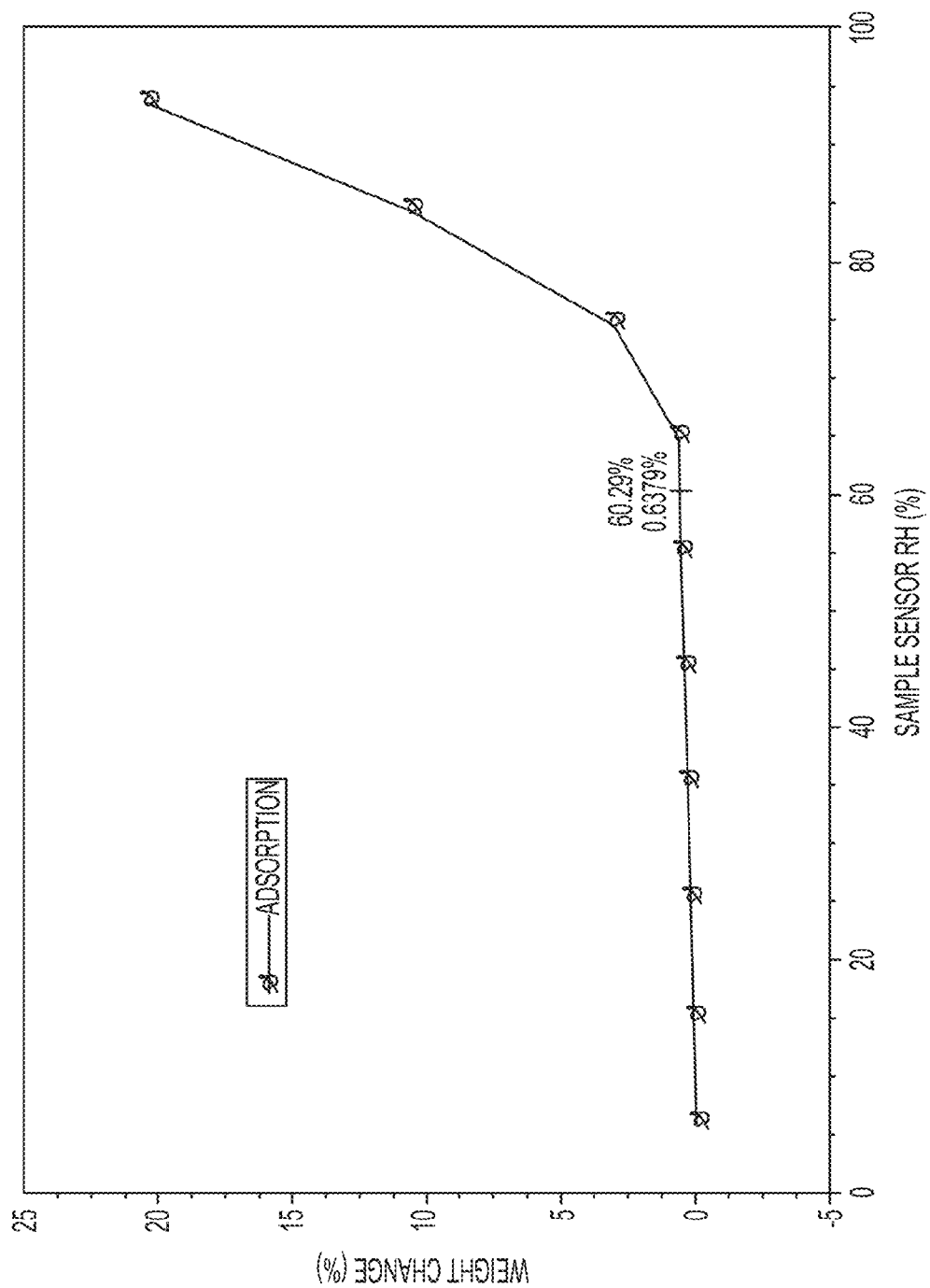
FIG. 18 shows a water sorption analysis of glyceryl capyrlate of compound of formula I at 25° C.
Figure 19:
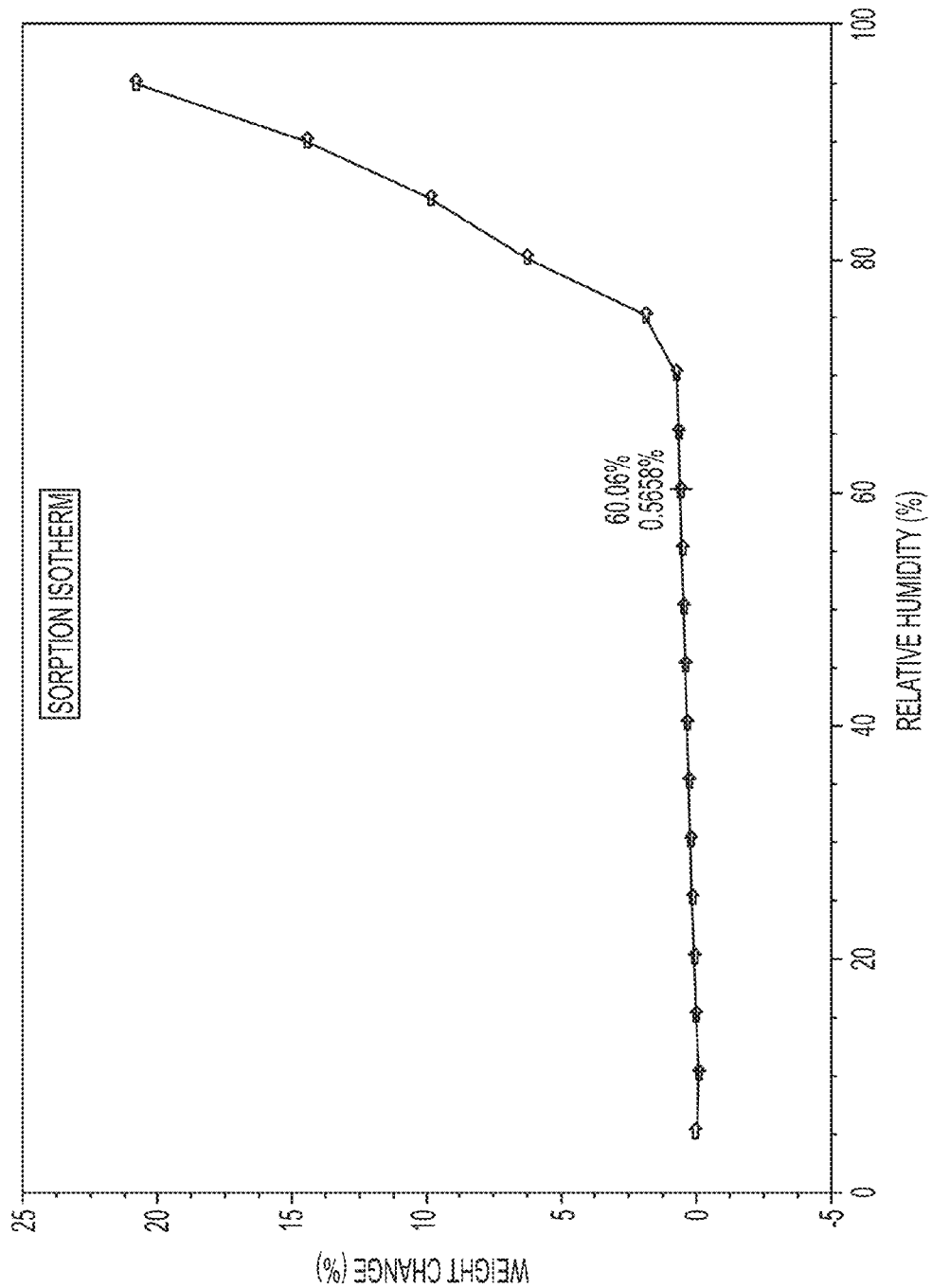
FIG. 19 shows a water sorption analysis of glyceryl laurate solvate of compound of formula I at 25° C.
Figure 20:
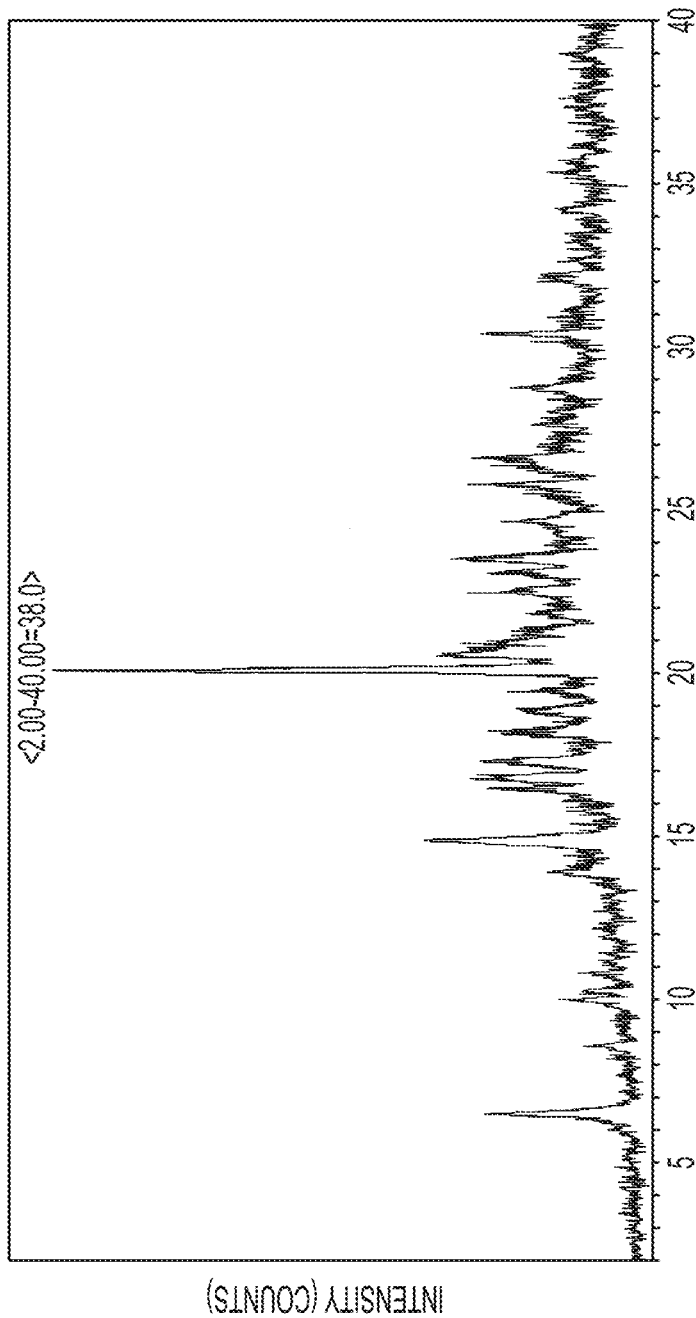
FIG. 20 shows the XRPD profile for a methyl tert-butyl ether (MTBE) solvate of compound of formula I formed by precipitating the solvate from MTBE or a mixture of MTBE with a solvent for example, chloroform.
Figure 21:
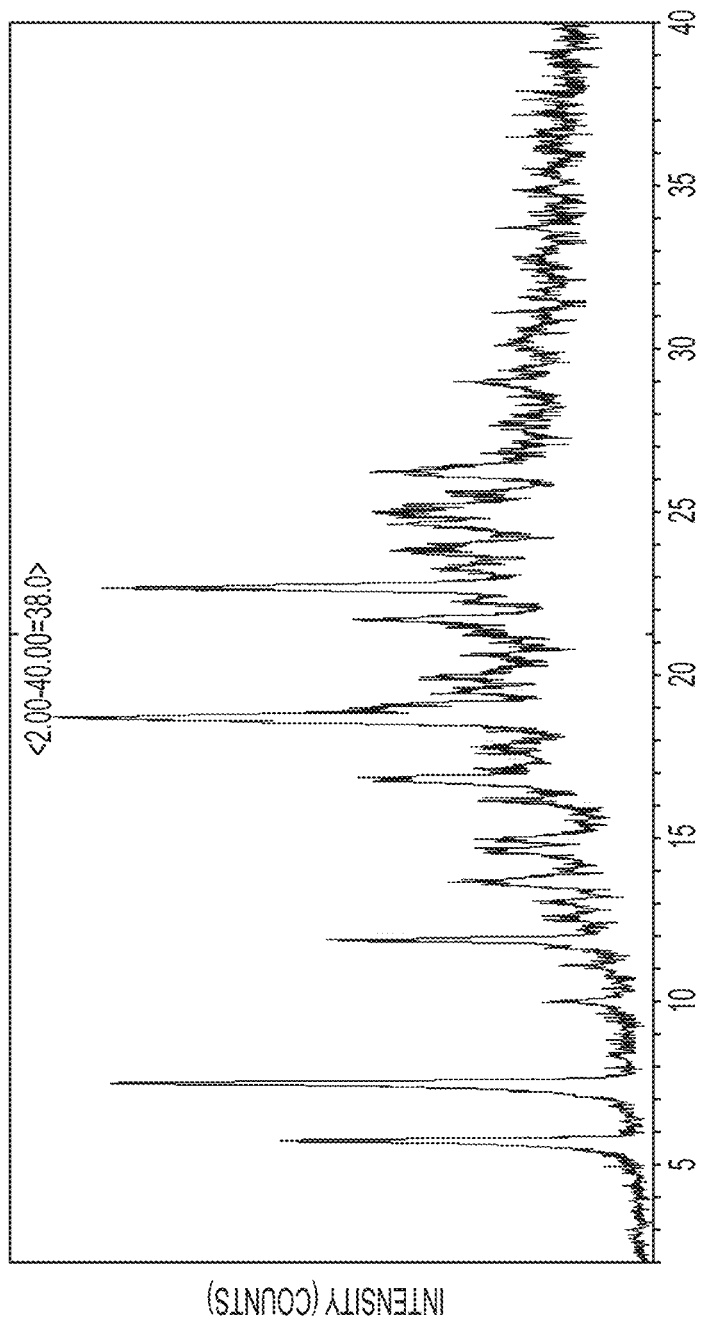
FIG. 21 shows the XRPD profile for a methyl ethyl ketone (MEK) solvate of compound of formula I formed by precipitating the solvate from MEK or a mixture of MEK with a solvent.
Figure 22:
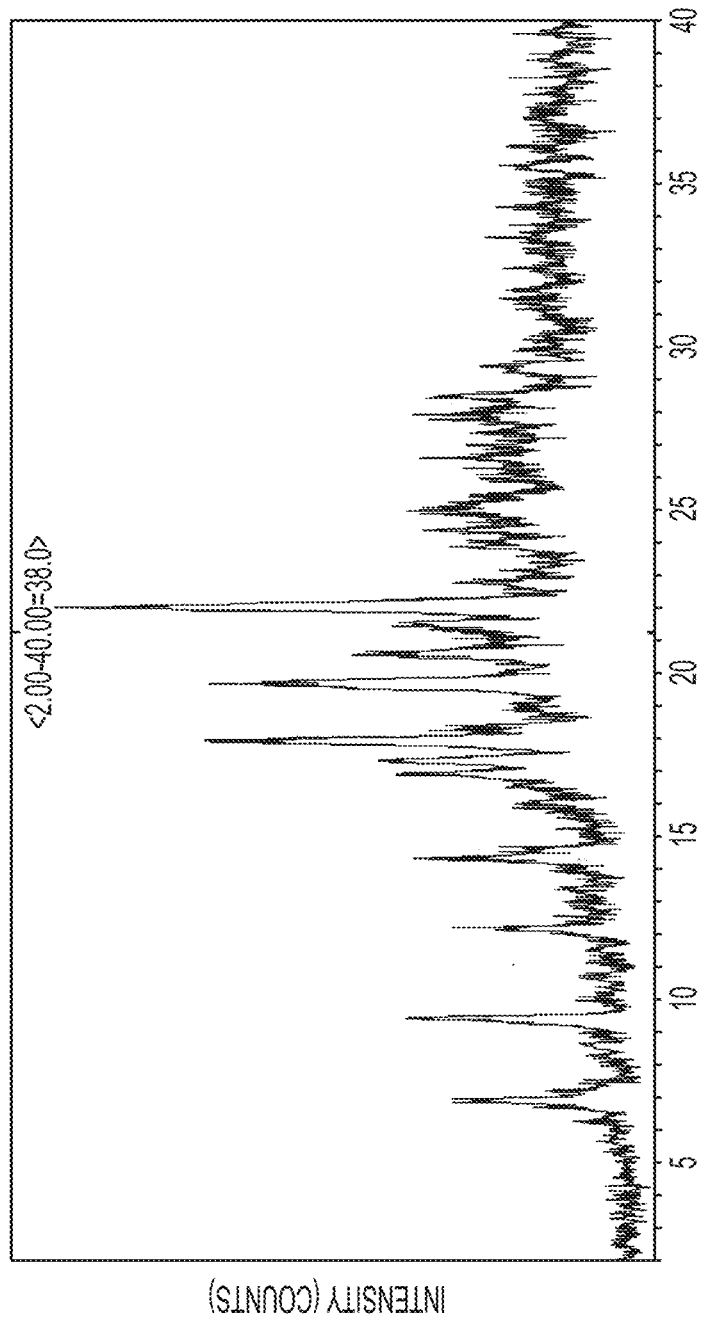
FIG. 22 shows the XRPD profile for a methyl isobutyl ketone (MIBK) solvate of compound of formula I formed by precipitating the solvate from MIBK or a mixture of MIBK with a solvent.
Figure 23:
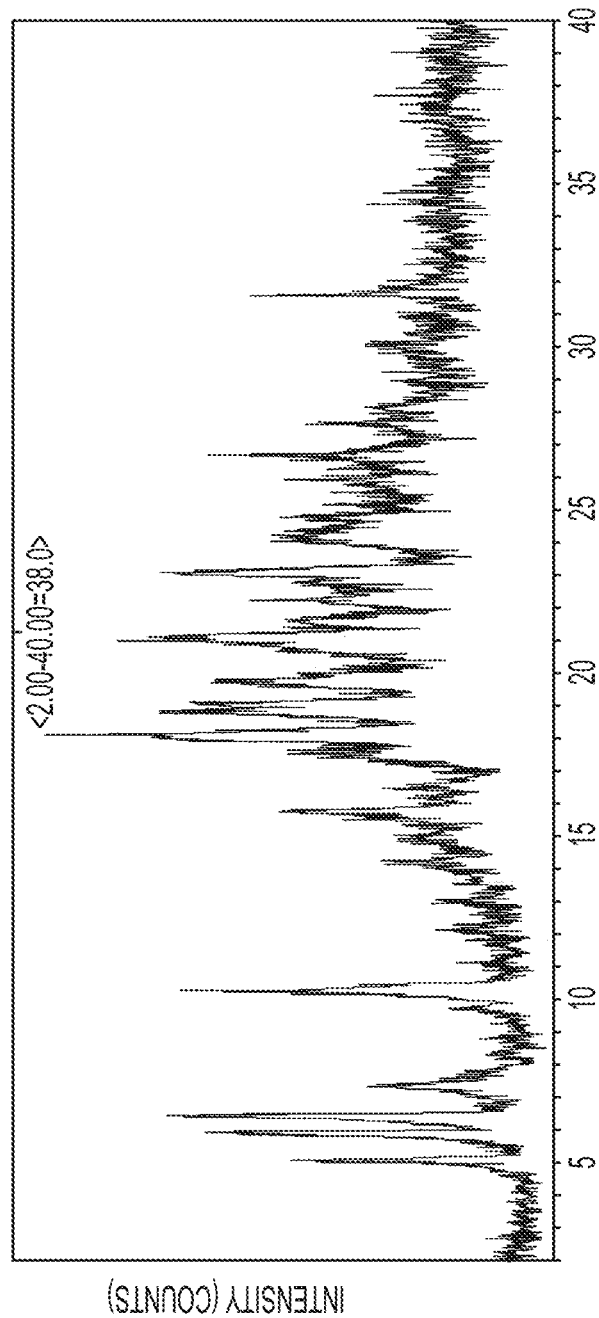
FIG. 23 shows the XRPD profile for a toluene solvate of compound of formula I formed by precipitating the solvate from toluene with a solvent.

Table 1 below and FIG. 5 show the characteristic XRPD peaks and pattern for the isolated (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride.

Therefore another aspect includes a form of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride having X-ray diffraction pattern that includes characteristic peaks, in 2-Theta (+/−0.2), occurring at 7.1. In an embodiment, the form also includes one or more characteristic peaks at 8.4, 8.8, 10.5, 12.7, 13.7, 13.9, 17.4, 21.1 and 22.3.

TABLE 1

| 2-Theta | d (Å) | BG | Height | H % | Area | A % | FWHM |
|---|---|---|---|---|---|---|---|
| 7.113 | 12.4168 | 30 | 104 | 100.0 | 1093 | 100.0 | 0.150 |
| 8.387 | 10.5334 | 29 | 24 | 23.5 | 389 | 35.6 | 0.227 |
| 8.835 | 10.0007 | 29 | 23 | 22.6 | 331 | 30.3 | 0.201 |
| 10.492 | 8.4248 | 25 | 28 | 27.0 | 212 | 19.4 | 0.108 |
| 12.693 | 6.9682 | 28 | 13 | 12.4 | 72 | 6.6 | 0.080 |
| 13.679 | 6.4684 | 31 | 26 | 25.3 | 322 | 29.4 | 0.174 |
| 13.875 | 6.3772 | 31 | 14 | 13.8 | 392 | 35.8 | 0.390 |
| 17.435 | 5.0824 | 37 | 21 | 20.1 | 279 | 25.5 | 0.190 |
| 21.095 | 4.2081 | 35 | 23 | 21.9 | 248 | 22.7 | 0.155 |
| 22.279 | 3.9870 | 35 | 15 | 14.9 | 144 | 13.2 | 0.133 |

EXAMPLE 2

Liquid Fill Capsule

Liquid fill formulations containing 47.5% w/w (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride were prepared in both capryol 90 and lauroglycol 90 to yield capsule dosage strength of 300 mg.

Capryol 90

Using a jacketed beaker, Capryol 90 (55.06 g) was heated to approximately 60° C., while mixing with a top down mixer at 300 RPM. BHA (149.9 mg) was added to the Capryol 90. (S)-2-(4-Chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride (49.96 g) was slowly added to the solution over the course of approximately 10 minutes. The impeller speed was increased to 1000 RPM and the solution mixed for approximately 80 minutes until all solids were dissolved. The solution was then sonicated for approximately 5 minutes to degas, and then allowed to cool to room temperature prior to capsule filling. The compounded liquid (700 mg) was filled into size 0 white gelatin capsules using a positive displacement pipette. All capsules were held upright in filling trays until banding. Using a gelatin banding solution of about 22% gelatin and 1% polysorbate 80 in water (% wt/wt), all capsules were banded using an automated capsule bander (Schaefer Technologies Laboratory Scale Bander). Sufficient solution was made to produce 150 capsules. After compounding and filling capsules, there were a total of 140 capsules produced. No capsules were rejected after filling, or banding. The total yield was 93%.

Lauroglycol 90

Using a jacketed beaker, Lauroglycol 90 (55.07 g) was heated to approximately 60° C., while mixing with a top down mixer at 400 RPM. BHA (150.2 g) was added to the Lauroglycol 90. (S)-2-(4-Chlorophenyl)-1-(4-((5R,7R)-7- hydroxy-5-methyl-6,7-dihydro-5H-cyclopenta[d]pyrimidin-4-yl)piperazin-1-yl)-3-(isopropylamino)propan-1-one monohydrochloride (49.97 g) was slowly added to the solution over the course of approximately 10 minutes. The impeller speed was increased to 1000 RPM and the solution mixed for approximately 100 minutes until all solids were dissolved. The solution was then sonicated for approximately 20 minutes to degas, and then allowed to cool to room temperature prior to capsule filling. The compounded liquid (700 mg) was filled into size 0 white HPMC capsules using a positive displacement pipette. All capsules were held upright in filling trays until banding. Using a gelatin banding solution of about 22% gelatin and 1% polysorbate 80 in water (% wt/wt), all capsules were banded using an automated capsule bander (Schaefer Technologies Laboratory Scale Bander). Sufficient solution was made to produce 150 capsules. After compounding and filling capsules, there were a total of 135 capsules produced, for a yield of 90%. While banding, 5 capsules were rejected. After the banding cooled overnight, and the capsules were inspected, an additional 7 capsules were rejected. A total of 123 acceptable capsules were obtained for a yield of 82%.

EXAMPLE 3

Tablet Formulation Containing a Dense Grade of Silica

| Ingredient | Amount (mg)/ 300-mg tablet | Amount (mg)/ 100-mg tablet | Amount (gm)/ 50 gm batch |
|---|---|---|---|
| (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride | 330 | 110 | 16.5 |
| Polyvinyl pyrolidone (PVP K30) | 25 | 8.33 | 1.25 |
| Butylated hydroxyl anisole | 1 | 0.33 | 0.05 |
| Croscarmellose sodium (internal phase) | 30 | 10 | 1.5 |
| Croscarmellose sodium (external phase) | 20 | 6.67 | 1.0 |
| Syloid 244 | 140 | 46.67 | 7.0 |
| Microcrystalline cellulose (PH 101) | 444 | 148 | 22.2 |
| *Ethanol/Water | q.s. | q.s. | q.s. |
| Stearic acid | 10 | 3.33 | 0.5 |

*Ethanol/water is evaporated during drying (S)-2-(4-Chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride (compound of formula I) was screened through a #30 screen to de-lump the large particles. BHA and PVP were dissolved into the ethanol-water solution (50:50 mix to make a total of 15 mL). The compound of formula I was slowly added to the solution with vigorous stirring conditions. Small amounts were added in incremental portions so as to allow complete dissolution. In a 0.5 L Diosna granulator bowl, the batch amounts of microcrystalline cellulose, Syloid 244 and croscarmellose sodium were mixed for 2 minutes in the high shear granulator using the impeller under a dry state so as to get a uniform mixture. This was followed by drop-wise addition of the solution containing the compound of formula I under constant agitation of the powder bed in the high shear granulator. After adding all the solution, the beaker was rinsed with about 2 mL of water and added dropwise into the granulation under agitation to so as to ensure the entire batch amount of solution is incorporated into the granulation. This was followed by a final rinse step of about 1 mL ethanol also added with agitation. After completion of the rinse addition, the impeller speed was increased and the chopper blade was turned on so as to perform the kneading or wet massing and facilitate particle growth. After about 2 minutes of kneading, a clear visual increase in particle size was observable and the granulation end-point could be confirmed by granule squeeze test. The granules were dried in a tray oven for about 4.5 hours to remove the ethanol and water. The final loss on drying from the granules was measured to be less than 3% w/w suggesting a dry granulation. Using the dried granules and re-calculating the exact amount of croscarmellose sodium and stearic acid required for the batch, pre-screened stearic acid was added stepwise to the batch and mixed on a turbula mixer. The final lubricated granulation was compressed on a Carver hydraulic press using capsule shaped tooling in order to compress 300-mg potency tablets at a press weight of 1000-mg.

EXAMPLE 4

Scale-Up Process for Tablet Manufacture

| Ingredient | Amount (mg)/ 300-mg tablet | Amount (mg)/ 100-mg tablet | Amount (gm)/ 1000 gm batch |
|---|---|---|---|
| (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride | 330 | 110 | 330 |
| Polyvinyl pyrolidone (PVP K30) | 25 | 8.33 | 25 |
| Butylated hydroxyl anisole | 1 | 0.33 | 1 |
| Croscarmellose sodium (internal phase) | 30 | 10 | 30 |
| Croscarmellose sodium (external phase) | 20 | 6.67 | 20 |
| Fumed silica (Cabosil MP-5) | 140 | 46.67 | 140 |
| Microcrystalline cellulose (PH 101) | 444 | 148 | 444 |
| *Ethanol/Water | q.s. | q.s. | q.s. |
| Stearic acid | 10 | 3.33 | 10 |

*Ethanol/water is evaporated during drying

The formulation shown above was processed in a Diosna 4 L granulator bowl. PVP-K-30 (25 g) and BHA (1 g) were dissolved into a mixture of 75 ethanol (200 proof) and 75 mL water. (S)-2-(4-Chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride (compound of formula I) was screened through a #30 mesh screen and slowly added to the vessel containing the BHA and PVP solution in ethanol-water. The compound of formula I was dissolved under high speed stirring in order to prevent clumping. The dissolver blade was rotated at 1000 rpm until a clear solution could be obtained. In a 4 L Diosna granulator bowl, the batch amounts of microcrystalline cellulose, CaboSil (fumed silica) and croscarmellose sodium were mixed for 2 minutes in the high shear granulator using the impeller under a dry state so as to get a uniform mixture. A persistaltic pump was set up to dispense the compound of formula I and granulating fluid at a controlled rate. A speed of 12 gram/minute provided a steady stream for the granulating solution containing compound of formula I being added into the bed while the impeller speed of the granulator was maintained at 150-rpm. After addition of the granulating fluid and the rinse solution making up a total of about 35% w/w ethanol-water with respect to the batch size, a clear growth in particle size was observed and also tracked by an increase in power consumption by the machine. This indicated an end-point of the granulation process. Finally, a wet-massing step was carried out at the impeller speed of 250 rpm and a chopper speed of 500-rpm in order to produce a uniform granulation. The granules were dried in fluid-bed drying equipment at 50° C. inlet air and 35 cubic feet per minute air swaps. The granules dried to moisture content of less than 3% w/w when the product temperature equilibrated at 42° C. The dried granules were then sized through a miller (Quadro-Comill) to obtain the desired particle size using a #16 mesh screen, a #18 screen and a #20 screen to identify the optimal screen size. These milled granules were mixed with the extra-granular portion of croscarmellose sodium and then lubricated with steric acid. Tablets having 100-mg and 300-mg strengths of compound of formula I were compressed on a Piccola tablet press using a 10-mm diameter round tooling for the 100-mg strength. The dissolution profiles in the figure below suggested that the milling screen size did not affect the dissolution behavior and either screen could be utilized.

EXAMPLE 5

Scale-Up of Tablet Formulation Up to 3-kg Using an Atomized Spray Process for Granulation

| Ingredient | Amount (mg)/ 300-mg tablet | Amount (mg)/ 100-mg tablet | Amount (gm)/ 3000 gm batch |
|---|---|---|---|
| (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride | 330 | 110 | 997.2 |
| Polyvinyl pyrolidone (PVP K30) | 25 | 8.33 | 75.0 |
| Butylated hydroxyl anisole | 1 | 0.33 | 3.0 |
| Croscarmellose sodium (internal phase) | 25 | 10 | 75.0 |
| Croscarmellose sodium (external phase) | 25 | 6.67 | 75.0 |
| Fumed silica (Aerosil 200) | 150 | 50.0 | 450.0 |
| Microcrystalline cellulose (PH 101) | 435.8 | 145.3 | 1307.3 |
| *Ethanol/Water | q.s. | q.s. | q.s. |
| Stearic acid | 12.5 | 4.20 | 37.5 |

*Ethanol/water is evaporated during drying

The formulation shown above was processed in a VG-25L Glatt granulator bowl. PVP-K-30 (75 g) and BHA (3 g) were dissolved into a mixture of 489 mL ethanol (200 proof) and 489 mL water. (S)-2-(4-Chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride (compound of formula I) was slowly added to the vessel containing the BHA and PVP solution in ethanol-water. The compound of formula I was dissolved under high speed stirring with a dissolver blade in order to prevent clumping. The dissolver blade was rotated at 1000 rpm until a clear solution could be obtained. In a VG-25L Glatt granulator bowl, the batch amounts of microcrystalline cellulose, Aerosil 200 (fumed silica) and croscarmellose sodium were mixed for 2 minutes in the high shear granulator using the impeller under a dry state so as to get a uniform mixture. A persistaltic pump was set up to dispense the compound of formula I and granulating fluid at a controlled rate and the solution was sprayed on to the powder bed of cellulose and silica using an atomization nozzle (Spray Systems) with a atomizing pressure of 3 psi. A speed of 91 gram/minute provided a good spray pattern for distributing the granulating solution containing compound of formula I over the powder bed while the impeller speed of the granulator was maintained at 100-rpm. After addition of the granulating fluid and the rinse solution (about 207 grams) making up a total of about 41% w/w ethanol-water with respect to the batch size, a clear growth in particle size was observed and also tracked by an increase in power consumption by the machine. This indicated an end-point of the granulation process. Finally, a wet-massing step was carried out at the impeller speed of 140 rpm and a chopper speed of 500-rpm in order to produce a uniform granulation. The granules were dried in fluid-bed drying equipment at 50° C. inlet air and 65 cubic feet per minute air swaps. The granules dried in a fluid-bed dryer to moisture content of less than 3% w/w when the product temperature equilibrated at 42° C. The dried granules were then sized through a miller (Fitz-mill with knives forward) to obtain the desired particle size using a #16 mesh screen, a #18 screen and a #20 screen to identify the optimal screen size. These milled granules were mixed with the extra-granular portion of croscarmellose sodium and then lubricated with steric acid. Tablets having 100-mg and 300-mg strengths of compound of formula I were compressed on a Piccola tablet press using a 10-mm diameter round tooling for the 100-mg strength and plain capsule shaped tooling having the dimensions of 0.3437"×0.7500" capsule for the 300-mg strength tablets.

Figure 24:
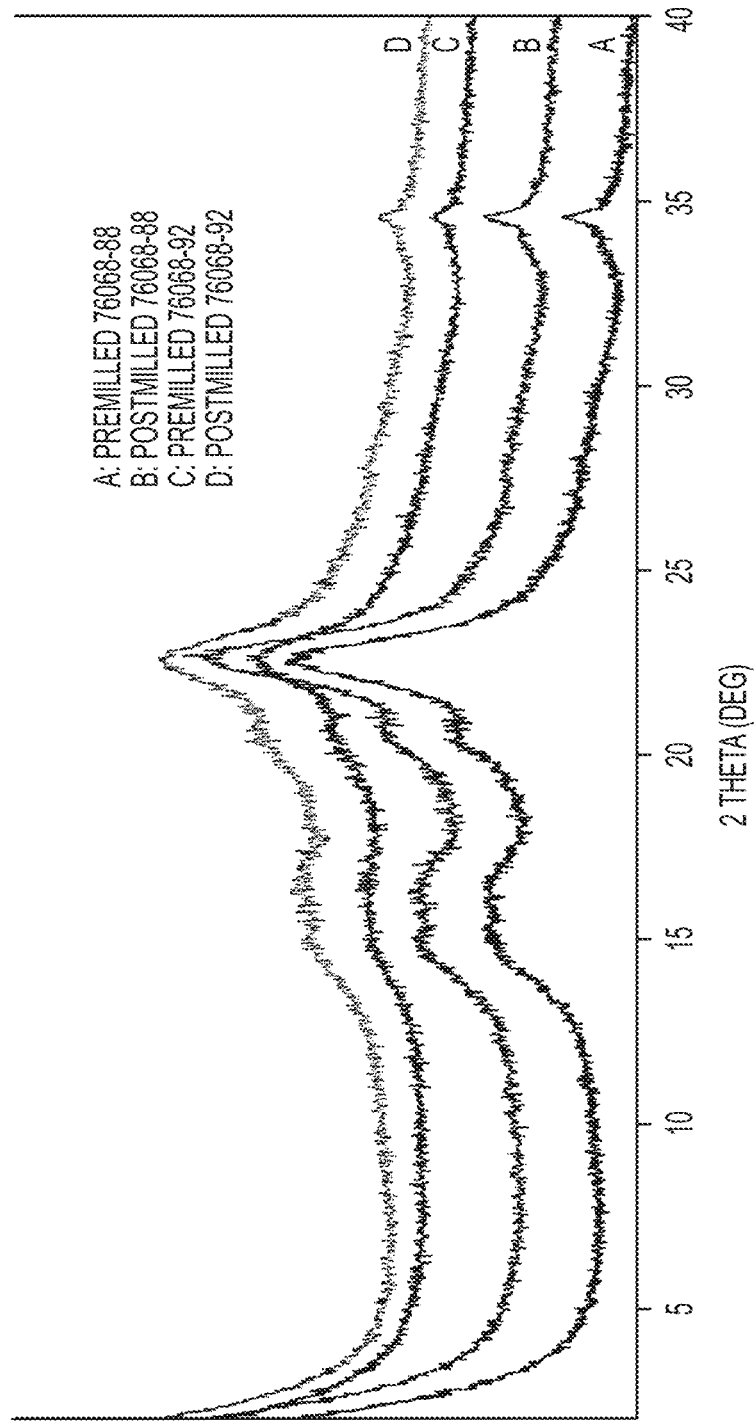
FIG. 24 shows the XRPD of pre and post milled batches of a compound of Formula I prepared by Direct Wet Granulation of a composition comprising partially crystalline compound of Formula I. Conversion of the partially crystalline form to amorphous form at 33% drug load, as well as at 43% drug load, occurs, without solution mediated precipitation.

FIG. 24 shows that the (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride is entrapped in an amorphous form in the formulation.

EXAMPLE 6

Tablet Formulation Using a Direct Wet Granulation Approach to Produce the Amorphous Form of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride

| Ingredient | Amount (mg)/ 300-mg tablet | Amount (mg)/ 100-mg tablet | Amount (gm)/ 150 gm batch |
|---|---|---|---|
| (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride | 325.7 | 108.6 | 48.9 |
| Polyvinyl pyrolidone (PVP K30) | 25 | 8.33 | 1.25 |
| Butylated hydroxyl anisole | 1 | 0.33 | 0.15 |

| Ingredient | Amount (mg)/ 300-mg tablet | Amount (mg)/ 100-mg tablet | Amount (gm)/ 150 gm batch |
|---|---|---|---|
| Croscarmellose sodium (internal phase) | 25 | 8.33 | 3.75 |
| Croscarmellose sodium (external phase) | 25 | 8.33 | 3.75 |
| Fumed Silica (Cabosil M5P) | 150 | 50.0 | 22.50 |
| Microcrystalline cellulose (PH 101) | 435.8 | 145.3 | 65.4 |
| *Ethanol/Water | q.s. | q.s. | q.s. |
| Stearic acid | 12.5 | 4.2 | 1.9 |

*Ethanol/water is evaporated during drying

BHA and PVP were dissolved into the ethanol-water solution (50:50 mix to make a total of 30 grams). In a 1.0 L Diosna granulator bowl, the batch amounts of (S)-2-(4-Chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride (compound of formula I), microcrystalline cellulose, Cabosil M5P and croscarmellose sodium were mixed for 2 minutes in the high shear granulator using the impeller under a dry state so as to get a uniform mixture. This was followed by drop-wise addition of the solution containing the BHA and PVP dissolved in ethanol and water, under constant agitation of the powder bed in the high shear granulator. After adding all the solution, the beaker was rinsed with about 30 grams of ethanol/water and added drop wise into the granulation under agitation to so as to ensure the entire batch amount of solution is incorporated into the granulation. This was followed by a final rinse step of about 20 grams ethanol/water also added with agitation. After completion of the rinse addition, the impeller speed was increased and the chopper blade was turned on so as to perform the kneading or wet massing and facilitate particle growth. After about 2 minutes of kneading, a clear visual increase in particle size was observable and the granulation end-point could be confirmed by granule squeeze test. The granules were dried in a tray oven for about 4.5 hours to remove the ethanol and water. The final loss on drying from the granules was measured to be less than 3% w/w suggesting a dry granulation. Using the dried granules and re-calculating the exact amount of croscarmellose sodium and stearic acid required for the batch, pre-screened stearic acid was added stepwise to the batch and mixed on a turbula mixer. The final lubricated granulation was compressed on a Carver hydraulic press using capsule shaped tooling in order to compress 300-mg potency tablets at a press weight of 1000-mg. The powder X-ray diffractograms for the granulation suggests that the compound (S)-2-(4-Chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride (compound of formula I) is converted to an amorphous state with this granulation method due to the exposure to an aqueous environment during granulation and removal of the ethanol water apparently and unexpectedly removes and residual crystalline order present in the material.

EXAMPLE 7

Scale-up of Tablet Formulation Using a Direct Wet Granulation Approach to Produce the Amorphous Form of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride

| Ingredient | Amount (mg)/ 300-mg tablet | Amount (mg)/ 100-mg tablet | Amount (gm)/ 600 gm batch |
|---|---|---|---|
| (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride | 325.7 | 108.6 | 195.4 |
| Polyvinyl pyrrolidone (PVP K30) | 25 | 8.33 | 15.0 |
| Butylated hydroxyl anisole | 1 | 0.33 | 0.60 |
| Croscarmellose sodium (internal phase) | 25 | 8.33 | 15.0 |
| Croscarmellose sodium (external phase) | 25 | 8.33 | 15.0 |
| Fumed Silica (Cabosil M5P) | 150 | 50.0 | 90.0 |
| Microcrystalline cellulose (PH 101) | 435.8 | 145.3 | 261.5 |
| *Ethanol/Water | q.s. | q.s. | q.s. |
| Stearic acid | 12.5 | 4.2 | 7.5 |

*Ethanol/water is evaporated during drying

BHA and PVP were dissolved into the ethanol-water solution (50:50 mix to make a total of 300 grams). In a 4.0 L Diosna granulator bowl, the batch amounts of (S)-2-(4-Chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride (compound of formula I), microcrystalline cellulose, Cabosil M5P and croscarmellose sodium were mixed for 2 minutes in the high shear granulator using the impeller under a dry state so as to get a uniform mixture. This was followed by addition of the solution using a peristaltic pump at a pump rate of 20 grams per minute to obtain a steady stream of granulating fluid containing the BHA and PVP dissolved in ethanol and water, under constant agitation of the powder bed in the high shear granulator at 170 rpm. After adding all the solution, the beaker was rinsed with about 30 grams of ethanol/water and added drop wise into the granulation under agitation to so as to ensure the entire batch amount of solution is incorporated into the granulation. After completion of the rinse addition, the impeller speed was increased to 200 rpm and the chopper blade was turned on so as to perform the kneading or wet massing and facilitate particle growth. After about 2 minutes of kneading, a clear visual increase in particle size was observable and the granulation end-point could be confirmed by granule squeeze test. The granules dried in a fluid-bed dryer to moisture content of less than 3% w/w when the product temperature equilibrated at 42° C. The dried granules were then sized through a miller (Fitz-mill with knives forward) to obtain the desired particle size using a #16 mesh screen, a #18 screen and a #20 screen to identify the optimal screen size. These milled granules were mixed with the extra-granular portion of croscarmellose sodium and then lubricated with steric acid. Tablets having 100-mg and 300-mg strengths of compound of formula I were compressed on a Piccola tablet press using a 10-mm diameter round tooling for the 100-mg strength and plain capsule shaped tooling having the dimensions of 0.3437"×0.7500" capsule for the 300-mg strength tablets.

Figure 25:
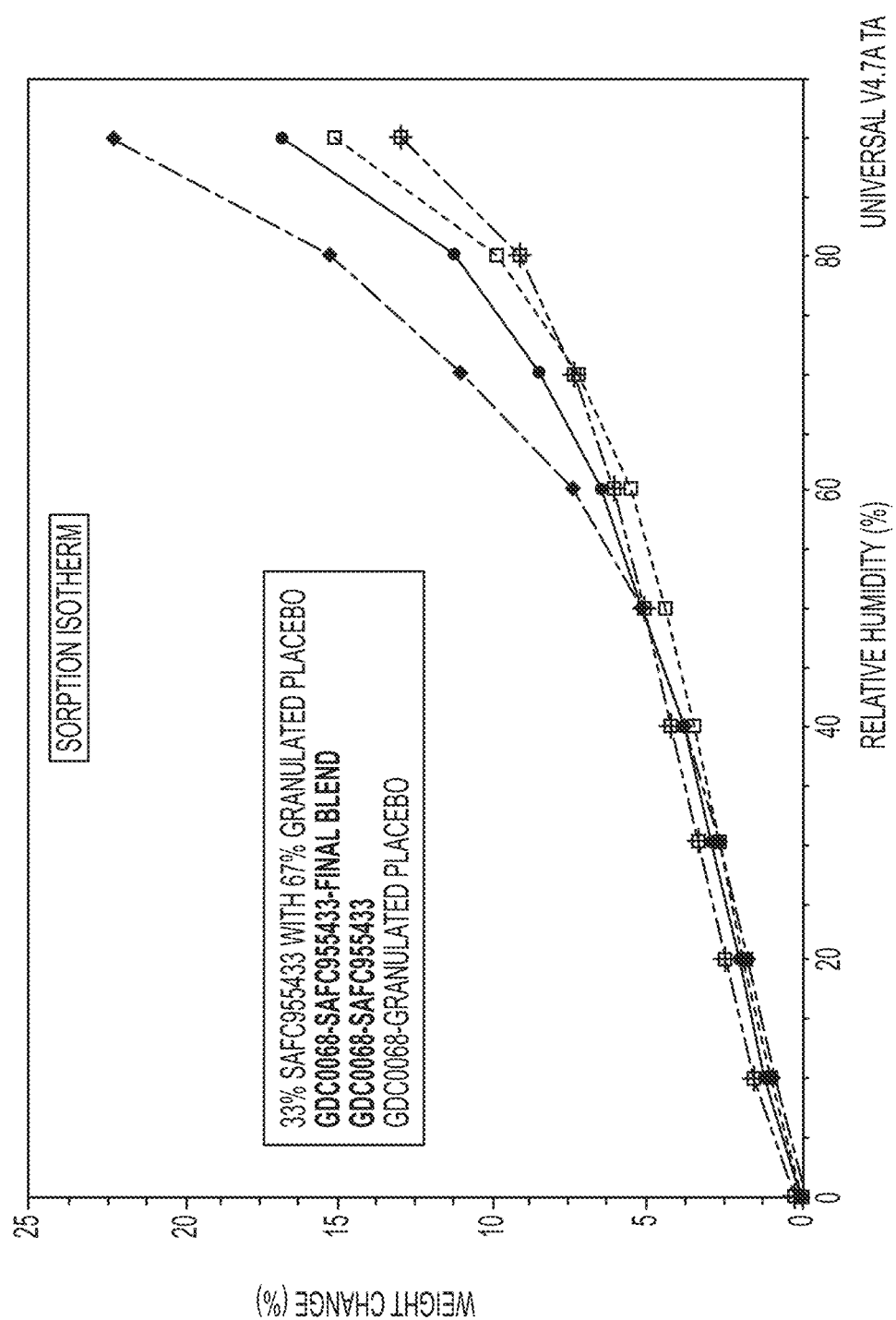
FIG. 25 shows the moisture sorption isotherm for a postmilled batch of a compound of Formula I prepared by Direct Wet Granulation of a composition comprising partially crystalline compound of Formula I at 43% drug load, which shows that the hygroscopicity of the compound is minimized by use of amorphous/fumed silica as an internal desiccant and the moisture sorption behavior is comparable to granules prepared from solution mediated precipitation of a compound of formula I.

FIG. 25 shows that the (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride is entrapped in an amorphous form in the formulation even after scaling up the process by a magnitude of 5×.

EXAMPLE 8

Tablet Formulation Using a Direct Wet Granulation Approach to Produce the Amorphous Form of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride in a 400-mg tablet

| Ingredient | Amount (mg)/ 400-mg tablet | Amount (mg)/ 100-mg tablet | Amount (gm)/ 150 gm batch |
|---|---|---|---|
| (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride | 434.3 | 144.8 | 65.2 |
| Polyvinyl pyrolidone (PVP K30) | 25 | 8.33 | 3.75 |
| Butylated hydroxyl anisole | 1 | 0.33 | 0.15 |
| Croscarmellose sodium (internal phase) | 25 | 8.33 | 3.75 |
| Croscarmellose sodium (external phase) | 25 | 8.33 | 3.75 |
| Fumed Silica (Cabosil M5P) | 150 | 50.0 | 22.50 |
| Microcrystalline cellulose (PH 101) | 327.2 | 109.1 | 49.1 |
| *Ethanol/Water | q.s. | q.s. | q.s. |
| Stearic acid | 12.5 | 4.2 | 1.9 |

*Ethanol/water is evaporated during drying

BHA and PVP were dissolved into the ethanol-water solution (50:50 mix to make a total of 30 grams). In a 1.0 L Diosna granulator bowl, the batch amounts of (S)-2-(4-Chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride (compound of formula I), microcrystalline cellulose, Cabosil M5P and croscarmellose sodium were mixed for 2 minutes in the high shear granulator using the impeller under a dry state so as to get a uniform mixture. This was followed by drop-wise addition of the solution containing the BHA and PVP dissolved in ethanol and water, under constant agitation of the powder bed in the high shear granulator at 150 rpm. After adding all the solution, the beaker was rinsed with about 30 grams of ethanol/water and added drop wise into the granulation under agitation to so as to ensure the entire batch amount of solution is incorporated into the granulation. This was followed by a final rinse step of about 30 grams ethanol/water also added with agitation. After completion of the rinse addition, the impeller speed was increased and the chopper blade was turned on so as to perform the kneading or wet massing and facilitate particle growth. After about 2 minutes of kneading, a clear visual increase in particle size was observable and the granulation end-point could be confirmed by granule squeeze test. The granules were dried in a tray oven for about 4.5 hours to remove the ethanol and water. The final loss on drying from the granules was measured to be less than 3% w/w suggesting a dry granulation. Using the dried granules and re-calculating the exact amount of croscarmellose sodium and stearic acid required for the batch, pre-screened stearic acid was added stepwise to the batch and mixed on a turbula mixer. The final lubricated granulation was compressed on a Carver hydraulic press using capsule shaped tooling in order to compress 400-mg potency tablets at a press weight of 1000-mg.

EXAMPLE 9

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride Capryolate and Lauryl glycolate solvate Capryolate Solvate (S)-2-(4-Chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride was dissolved 47.5% w/w in 52.5% w/w Capryol 90 with repeated sonication (sonicating bath and overhead sonicator), stirring and heating at 60-70° C. A clear solution was obtained which produced a white precipitate in 2 months upon standing at room temperature. The precipitate was characterized as capryol solvate.

Table 2 below shows the characteristic XRPD peaks of the crystalline solvate.

TABLE 2

| 2-Theta | d (Å) | BG | Height | H % | Area | A % | FWHM |
|---|---|---|---|---|---|---|---|
| 6.517 | 13.5521 | 604 | 31644 | 100.0 | 154231 | 100.0 | 0.069 |
| 6.934 | 12.7368 | 566 | 15942 | 50.4 | 76663 | 49.7 | 0.068 |
| 10.692 | 8.2674 | 531 | 8042 | 25.4 | 42607 | 27.6 | 0.075 |
| 12.282 | 7.2005 | 588 | 2507 | 7.9 | 14932 | 9.7 | 0.085 |
| 13.839 | 6.3936 | 509 | 2993 | 9.5 | 18931 | 12.3 | 0.090 |
| 15.607 | 5.6734 | 622 | 5271 | 16.7 | 30892 | 20.0 | 0.083 |
| 18.465 | 4.8012 | 622 | 19212 | 60.7 | 135634 | 87.9 | 0.100 |
| 18.918 | 4.6871 | 622 | 5360 | 16.9 | 65512 | 42.5 | 0.174 |
| 19.520 | 4.5440 | 957 | 2727 | 8.6 | 17618 | 11.4 | 0.092 |
| 21.409 | 4.1472 | 969 | 11517 | 36.4 | 89885 | 58.3 | 0.111 |

Lauryl Glycol Solvate (S)-2-(4-Chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride was dissolved 47.5% w/w in 52.5% w/w lauryl glycol with repeated sonication (sonicating bath and overhead sonicator), stirring and heating at 60-70° C. A clear solution was obtained which produced a white precipitate was obtained upon storage in 4 weeks at 25° C./60% RH. The precipitate was characterized as laurylglycolate solvate.

Table 3 below shows the characteristic XRPD peaks of the crystalline solvate.

TABLE 3

| 2-Theta | d (Å) | BG | Height | H % | Area | A % | FWHM |
|---|---|---|---|---|---|---|---|
| 6.515 | 13.5569 | 598 | 36382 | 100.0 | 259720 | 100.0 | 0.101 |
| 6.947 | 12.7146 | 596 | 20068 | 55.2 | 97362 | 37.5 | 0.069 |
| 10.677 | 8.2793 | 567 | 4232 | 11.6 | 25836 | 9.9 | 0.087 |
| 13.840 | 6.3936 | 547 | 4033 | 11.1 | 31256 | 12.0 | 0.110 |
| 15.592 | 5.6785 | 595 | 6471 | 17.8 | 45117 | 17.4 | 0.099 |
| 18.465 | 4.8011 | 662 | 10757 | 29.6 | 109728 | 42.2 | 0.145 |
| 18.918 | 4.6873 | 662 | 9863 | 27.1 | 103366 | 39.8 | 0.149 |
| 19.521 | 4.5438 | 1090 | 3760 | 10.3 | 31463 | 12.1 | 0.119 |
| 21.058 | 4.2155 | 974 | 3663 | 10.1 | 55103 | 21.2 | 0.214 |

TABLE 3-continued

| 2-Theta | d (Å) | BG | Height | H % | Area | A % | FWHM |
|---|---|---|---|---|---|---|---|
| 21.376 | 4.1534 | 996 | 6914 | 19.0 | 79912 | 30.8 | 0.164 |
| 23.598 | 3.7672 | 963 | 2793 | 7.7 | 58900 | 22.7 | 0.300 |

Variable temperature XRD showed that both solvates are stable up to 80° C. At temperatures ≥80° C., there is substantial loss of crystallinity. In both samples, they appear to be X-ray amorphous at 90° C. and above (due to melting of the lattice solvent and dissolution of the solid phase in it as confirmed by hot stage microscopy). Taken together, the analysis of the solvates shows them to be highly crystalline, stable, non-hygroscopic, have about 18-22% solvent uptake in the crystal lattice and at ambient temperature, exhibit almost 2 fold lower solubility in respective solvents than the material of Example 1.

EXAMPLE 10

Figure 26:
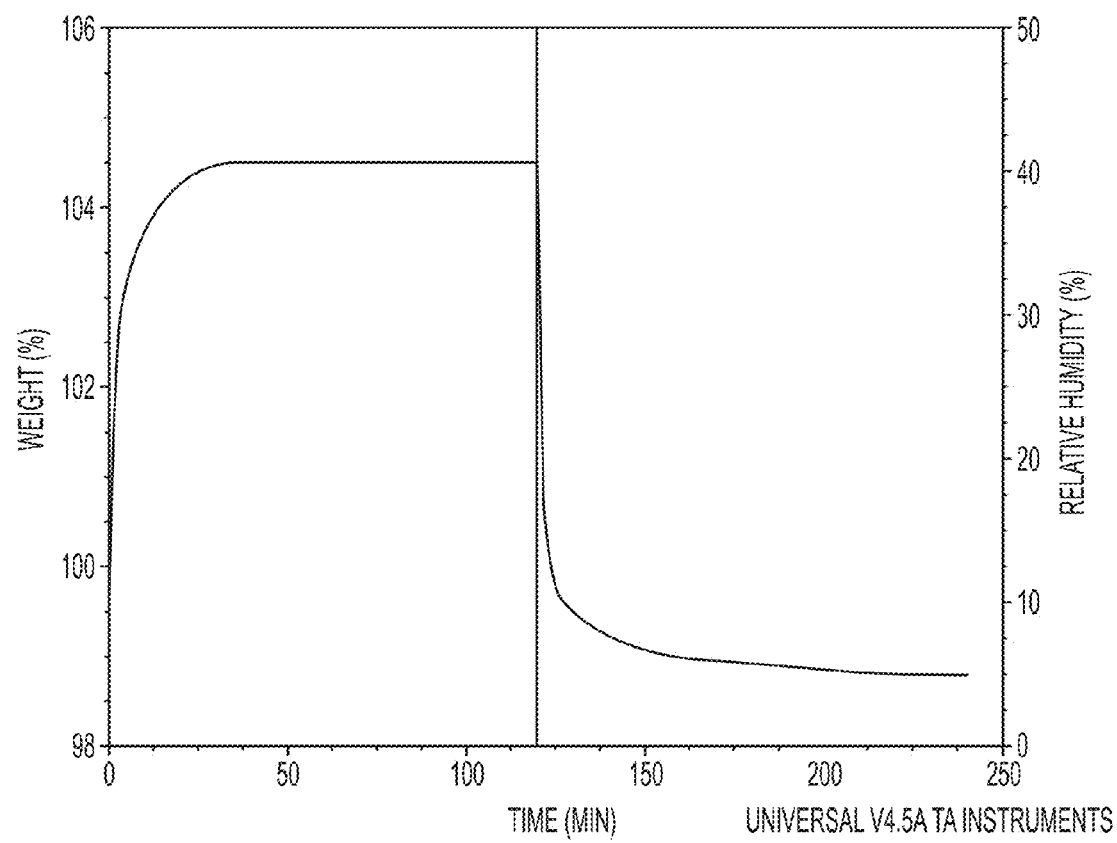
FIG. 26 shows the DVS program for the product of Example 10.
Figure 27:
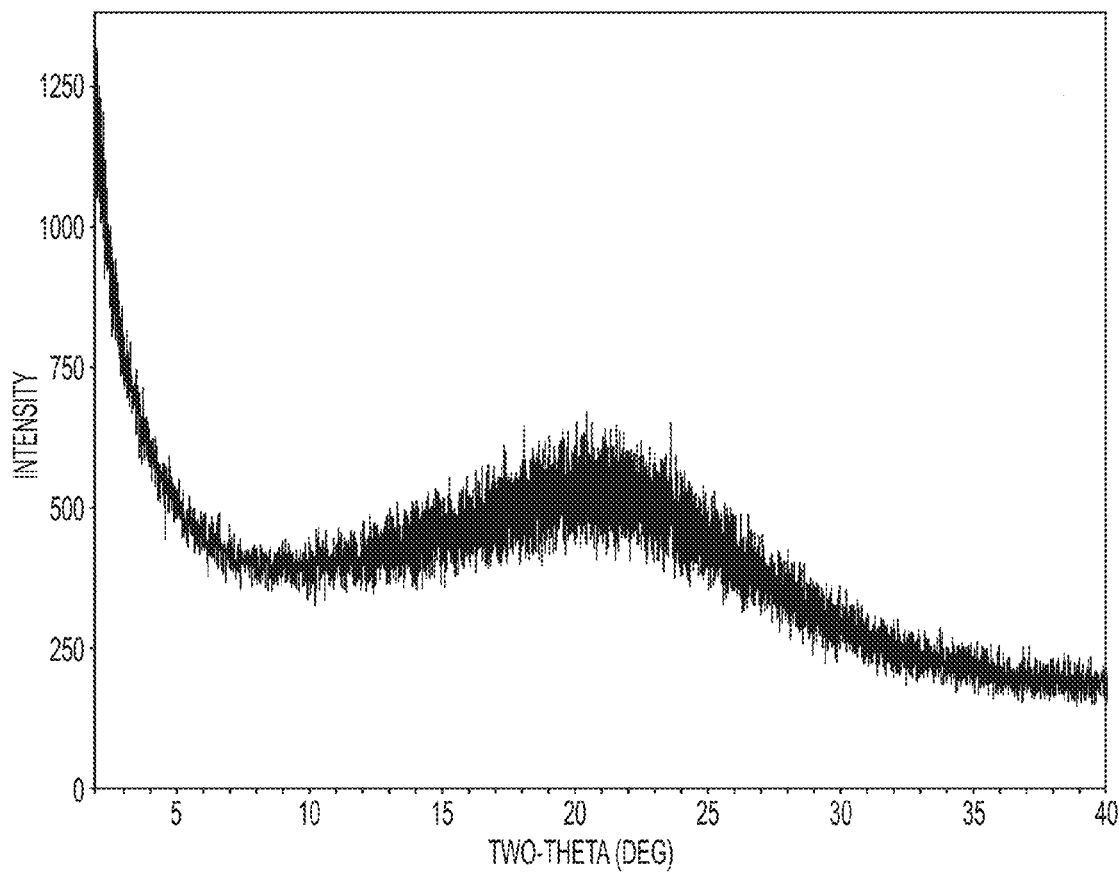
FIG. 27 shows the XRPD profile for the product of Example 10.
Figure 28:
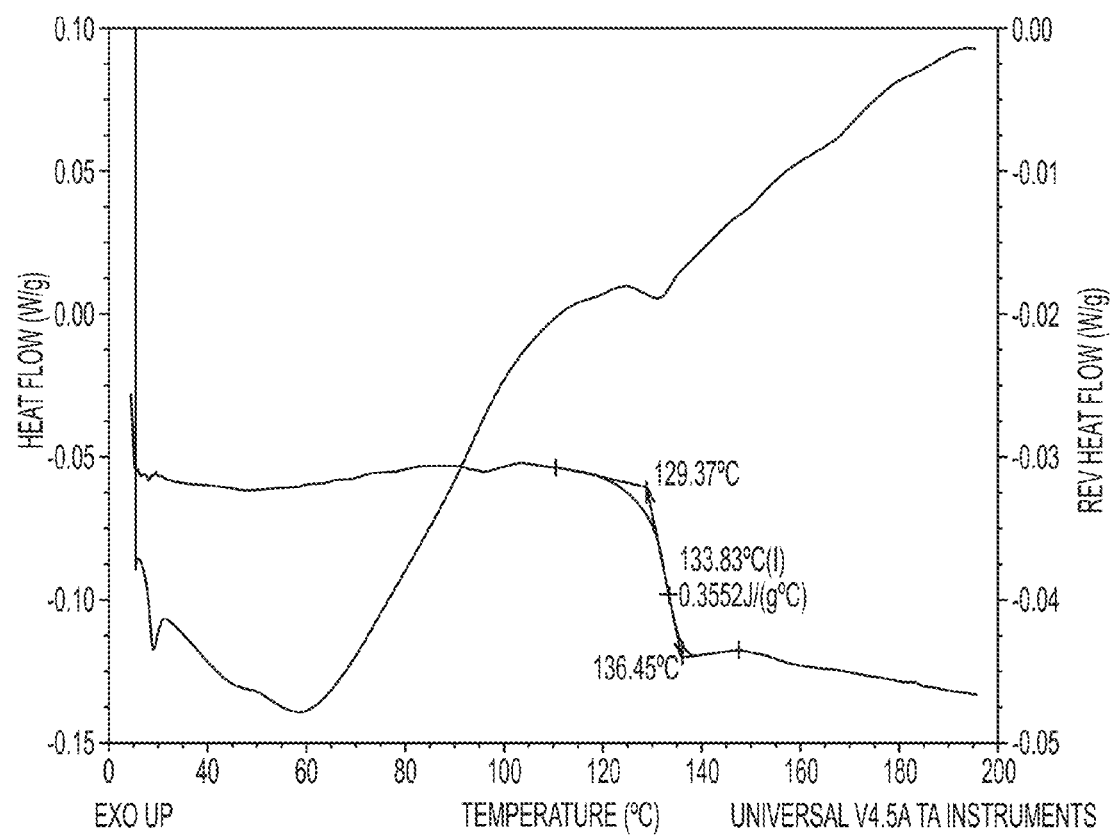
FIG. 28 shows the DSC profile for the product of Example 10.

Amorphous (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride The material of Example 1 was dissolved in 10 volumes of ethanol. A stir bar was added to the rotovap flask and the solvent was evaporated under reduced pressure on a rotary evaporator to give foam. The foam is scraped to knock down the foam and drying is continued until a free flowing solid is obtained. A sample of the product (4.70 mg), is placed in a pre-weighed aluminum pan and placed in the oven on a TA Instruments Q5000SA vapor sorption analyzer. The sample was heated to 50° C. under a stream of dry nitrogen and equilibrated. The relative humidity was increased to 50% at 50° C. and held there for 2 hours. The humidity was then lowered to 0% RH while the temperature was maintained at 50° C. and held there for 2 hours. The sample was then analyzed by XRPD (FIG. 27) and modulated DSC (FIG. 28). The DVS program is graphically shown in FIG. 26. The DSC method was done by using modulated DSC at a rate of 2° C./minute with modulation of ±1° C. every 60 seconds using a lightly crimped pan which allows solvent to escape during the run.

EXAMPLE 11

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride toluene solvate Toluene, 5 mL, was added to material from Example 1 (20 mg). The slurry was heated to 50° C. in a shaker block for 1 day. Most of the solid was dissolved and then a small amount precipitated from solution at 50° C. Most of the liquid was removed and the suspension was allowed to cool to room temperature. Crystals suitable for structure determination were obtained. The crystals obtained contained 0.64 moles of toluene/mole of the compound of Formula I.

Figure 29:
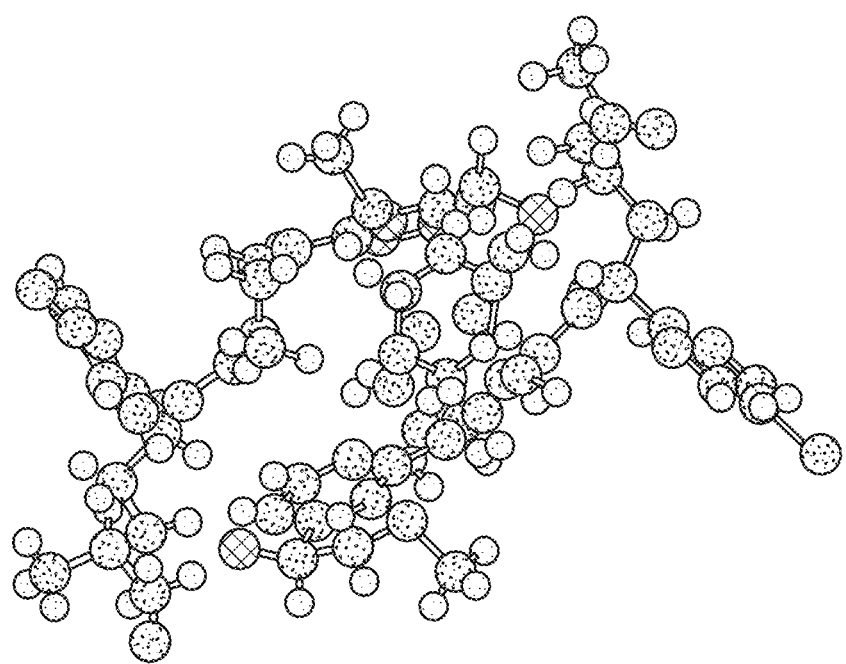
FIG. 29 shows the single crystal lattice structure for the product of Example 11.

A single crystal was obtained with the following data: formula C55H74Cl4N10O4, formula weight 1081.04, space group P 21 21 21 (No. 19), a, Å 14.074(2), b, Å 16.621(2), c, Å 24.363(3), α, deg 90, β, deg 90, γ, deg 90, V, Å$^3$ 5699.0(14), Z 4, $d_{calc}$, g cm$^{-3}$ 1.260, temperature, K 100. radiation (wavelength, Å) Cu K$_\alpha$ (1.54184), diffractometer BrukerAPEX-II CCD', h, k, l range −16 to 16 −19 to 20 −29 to 29, θ range, deg 3.29-68.397, programs used SHELXTL 2013, data collected 10425, unique data 9646, R(F$_o$) 0.076, R$_w$(F$_o^2$) 0.2010, goodness of fit 1.41, and is shown in FIG. 29.

Figure 30B:
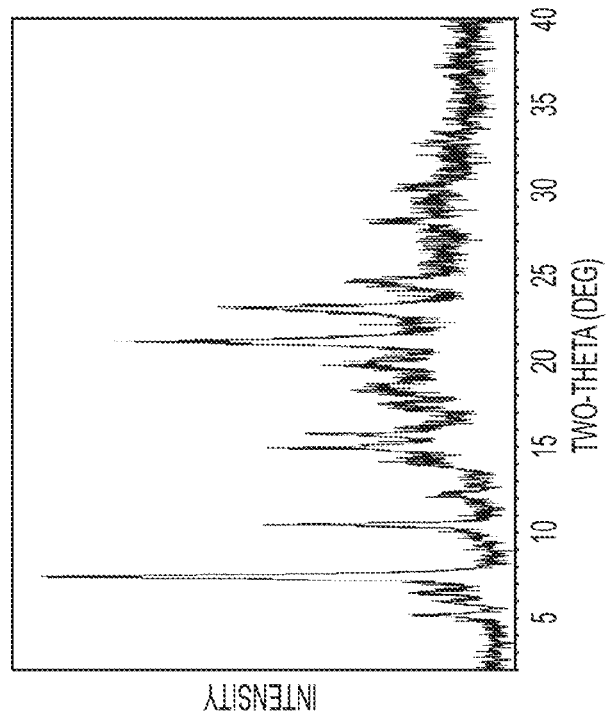
FIGS. 30A-B show the XRPD profiles for the products of Example 11.
Figure 30A:
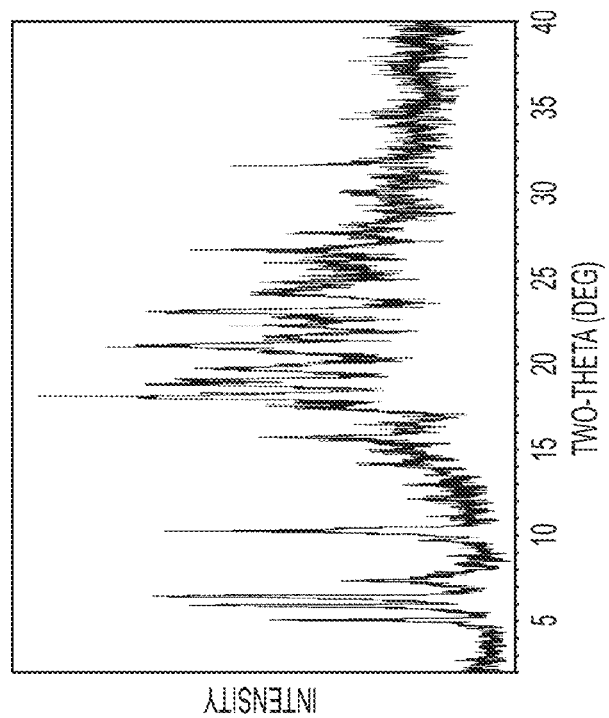

Amorphous compound of Formula I was dissolved in a mixture of toluene, 1 mL, and tetrahydrofuran, 600 µL. The solution was placed into a desiccator to slowly evaporate. The lid of the desiccator was opened periodically to allow the solvent vapors to escape. After 7 days, crystals were isolated from the remaining solution (FIG. 30A). The product was dried at 50° C. and 50 torr for 1 hour to give a partially desolvated toluene solvate. The XRPD of the solvate and partially desolvated solvate are shown in FIGS. 30A and 30B, respectively.

EXAMPLES 12 A-C

Figure 31A:
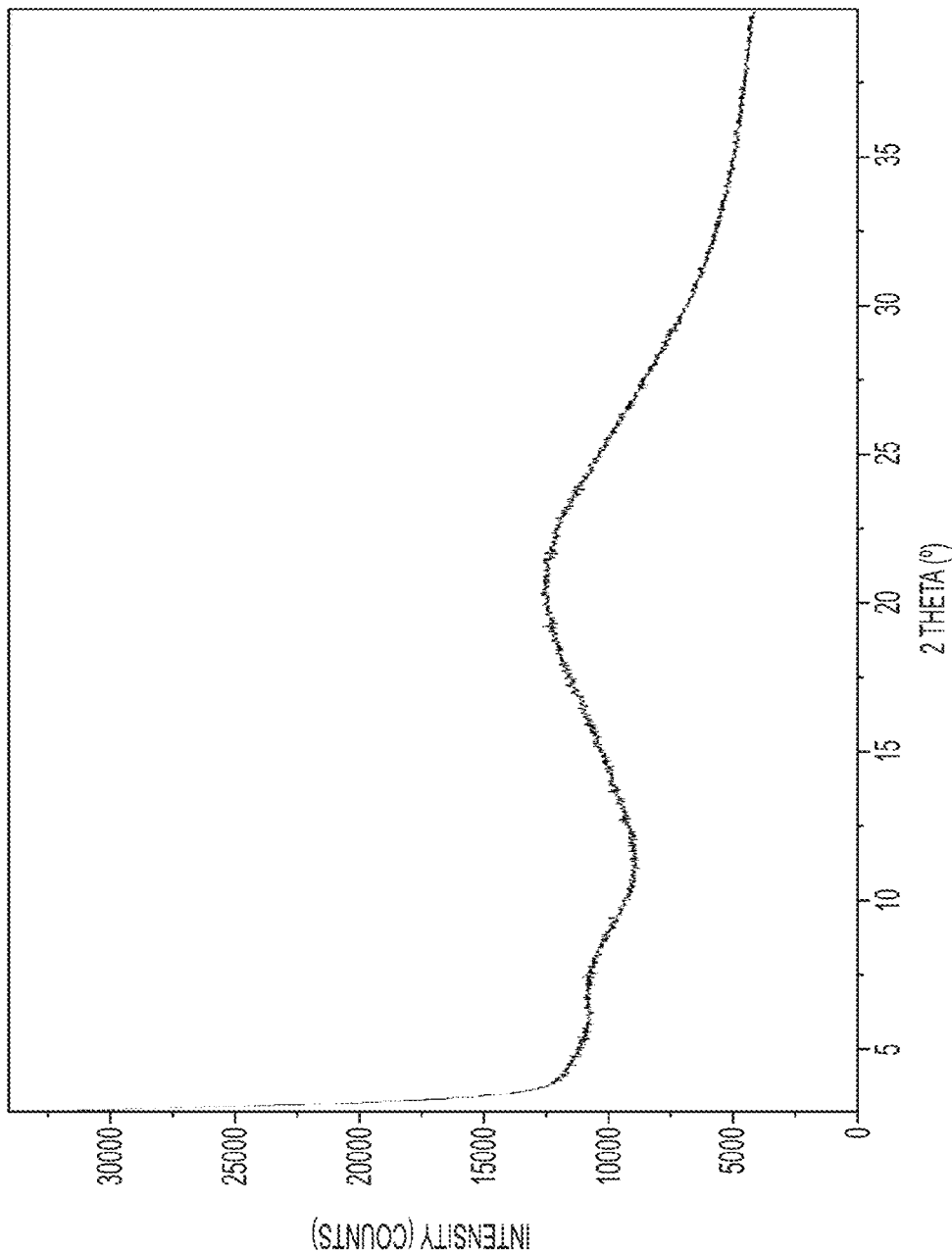
FIGS. 31A-C show the XRPD profiles for the products of Example 12 (amorphous spray dried compound of formula I).
Figure 31B:
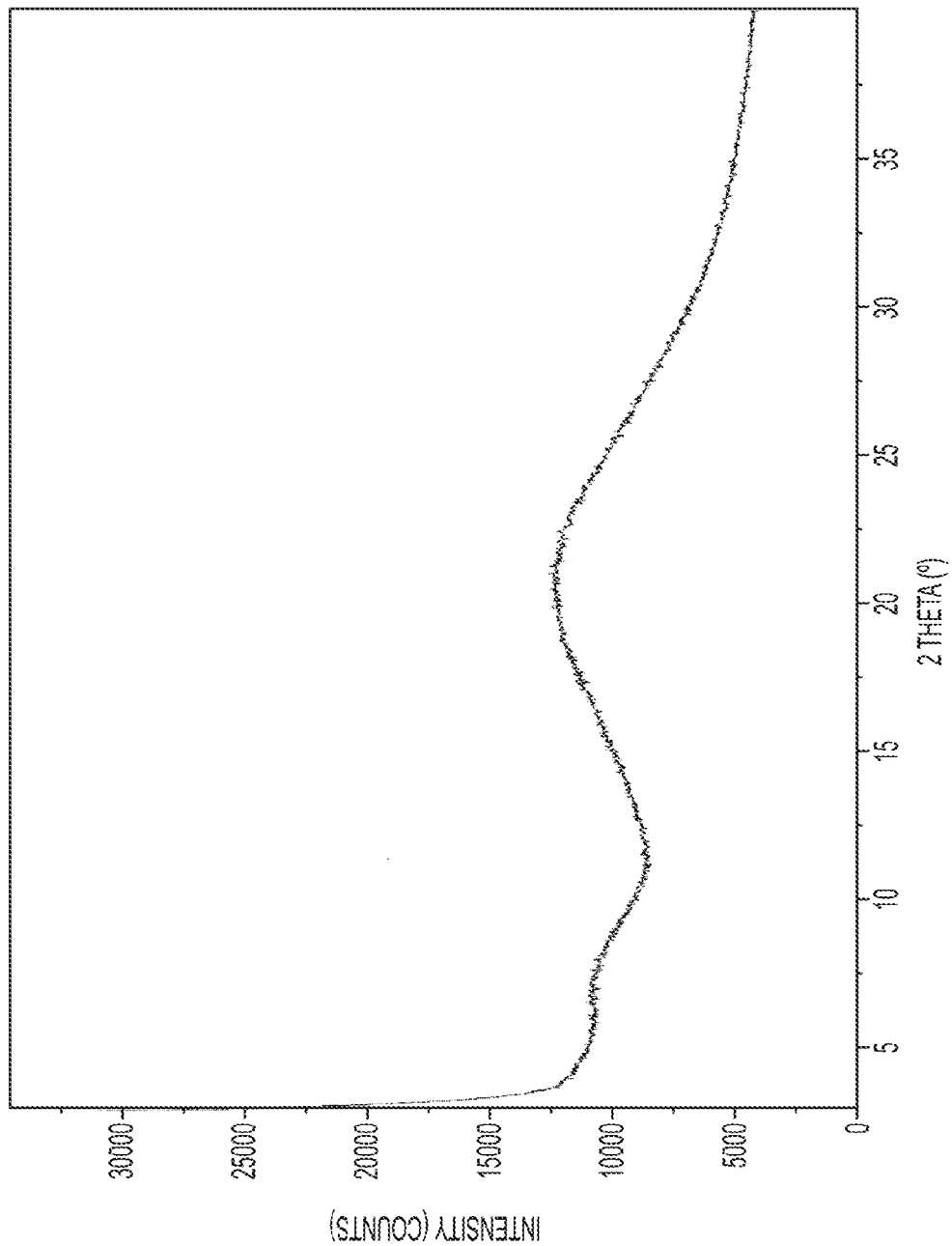
Figure 31C:
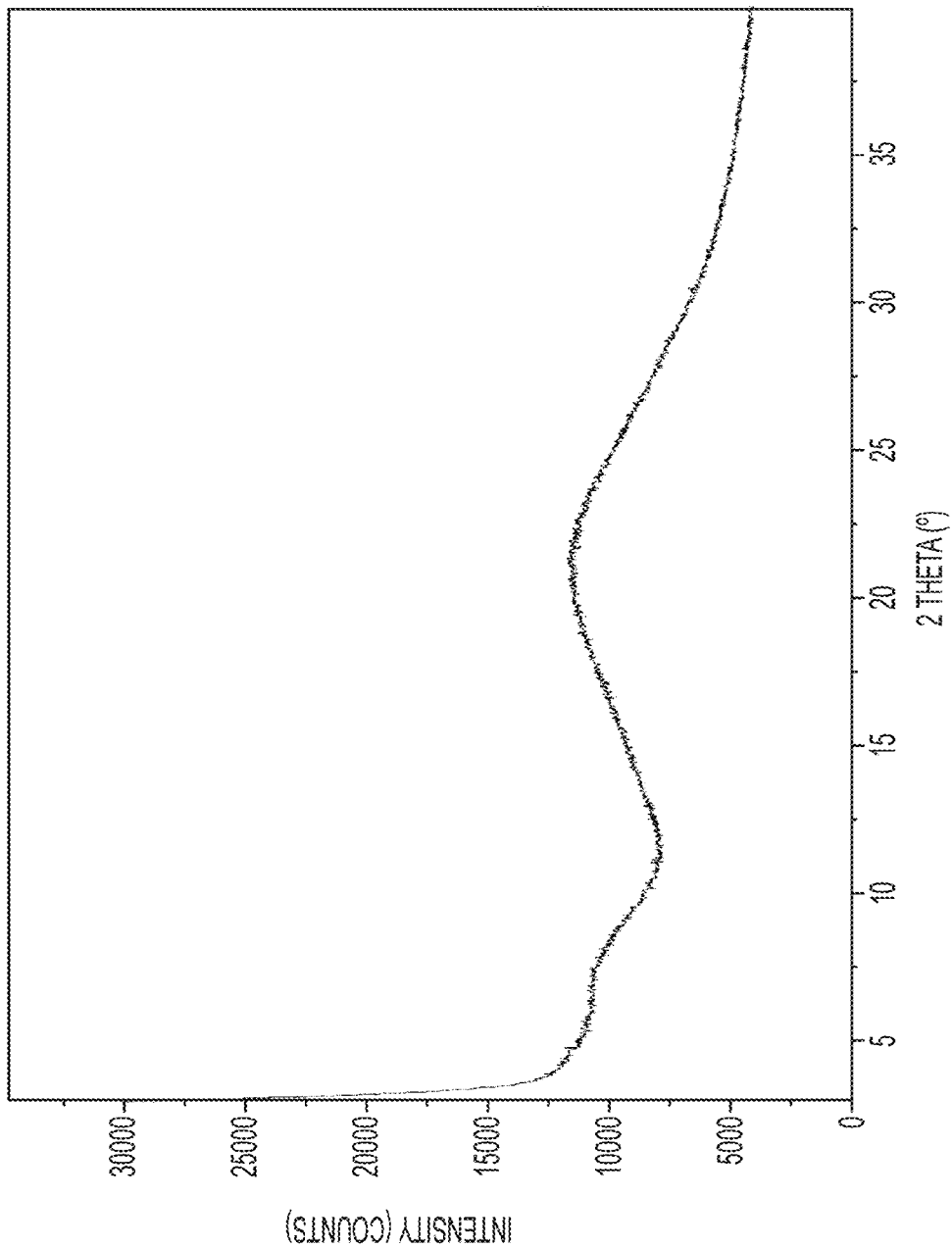
Figure 32:
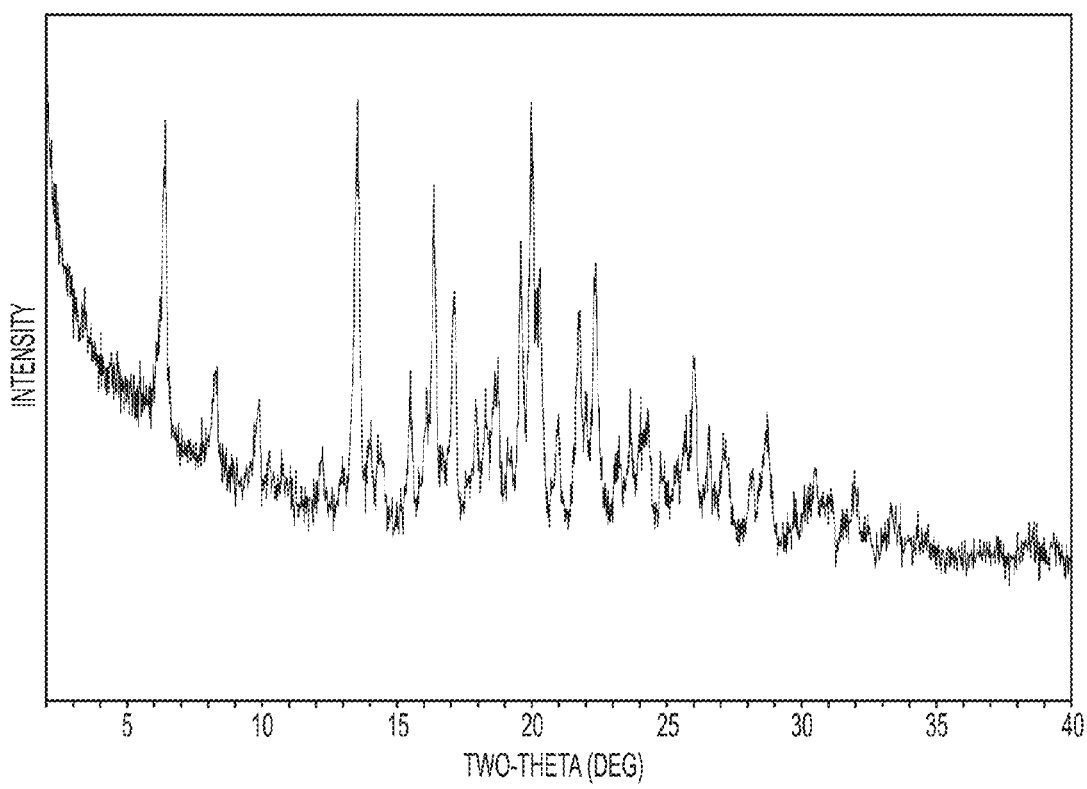
FIG. 32 shows the XRPD profile of ethyl acetate solvate of compound of formula I.
Figure 33:
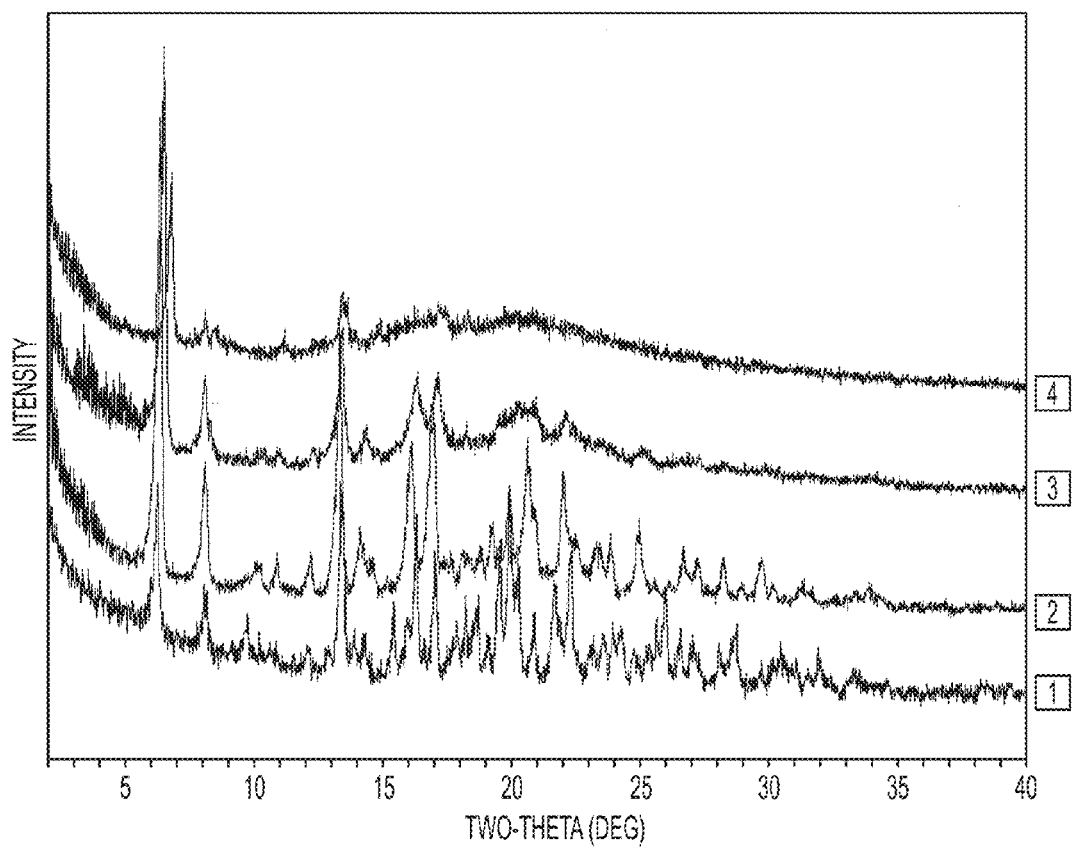
FIG. 33 shows the XRPD profiles of the ethyl acetate solvate of compound of formula I under varying drying conditions. Profile 1 shows the solvate analyzed in a "semi'sealed" sample holder; profile 2 shows the solvate analyzed in holder open to air; profile 3 shows the solvate analyzed after heating to 75° C. in a vacuum oven for 1 hour; and profile 4 shows the solvate heated at 75° C. in a vacuum oven for 5 hours.

Amorphous (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride prepared by spray-drying Amorphous (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride was prepared by spray drying solutions of various forms of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride. The conditions and results of several experiments are shown below in Table 4 (See FIGS. 31A for 12A, 31B for 12B and 31C for 12C).

TABLE 4

| Example Number | | 12A | 12B | 12C |
|---|---|---|---|---|
| Loop | | Open | Open | Open |
| Feed composition | | | | |
| Starting material | | Compound of Formula I Ethyl Acetate Solvate | Compound of Formula I (Example 1) | Compound of Formula I Ethyl Acetate Solvate |
| Process Solvent | | Ethanol | Ethanol | Water |
| Feed properties | | | | |
| Total Starting Material [a] | g | 50.0 | 50.0 | 25.0 |
| Total Process Solvent [a] | g | 250.0 | 250.0 | 100.0 |
| Feed solution | g | 300.0 | 300.0 | 125.0 |
| C_feed | % w/w | 16.7 | 16.7 | 20.0 |
| Spray drying parameters | | | | |
| T_in | ° C. | 120 ± 1 | 119 ± 1 | 154 ± 1 |
| T_out | ° C. | 69 ± 1 | 69 ± 1 | 90 ± 1 |
| F_feed | mL/min | 15 | 15 | 5 |
| Rotamer level | mm | 40 | 40 | 40 |
| Drying time | min | 23 | 23 | 23 |
| Process yield | | | | |
| Yield | g | 28.8 | 48.4 | 15.0 |
| Yield | % | 58 | 97 | 60 |
| Analytical results | | | | |
| Water content | % w/w | 0.89 | 0.43 | 1.02 |
| Ethanol | % w/w | 2.19 | 2.78 | 0.01 |
| Ethyl acetate | % w/w | 0.25 | 0.01 | 0.23 |

[a] No corrections were made to consider the amount of solvent in the crystal

EXAMPLE 11

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride ethyl acetate solvate In a visually clean 10 L jacketed cylindrical vessel under nitrogen was charged GDC-0068.HCl (500 g) and ethyl acetate (5 L). The resulting slurry was heated to 60° C. for 72 hours and aliquots were pulled to monitor the conversion to EtOAc solvate by XRPD analysis. The slurry was cooled to 5° C., filtered and dried under vacuum at room temperature for 5 min.

Alternative Procedure

Figure 34B:
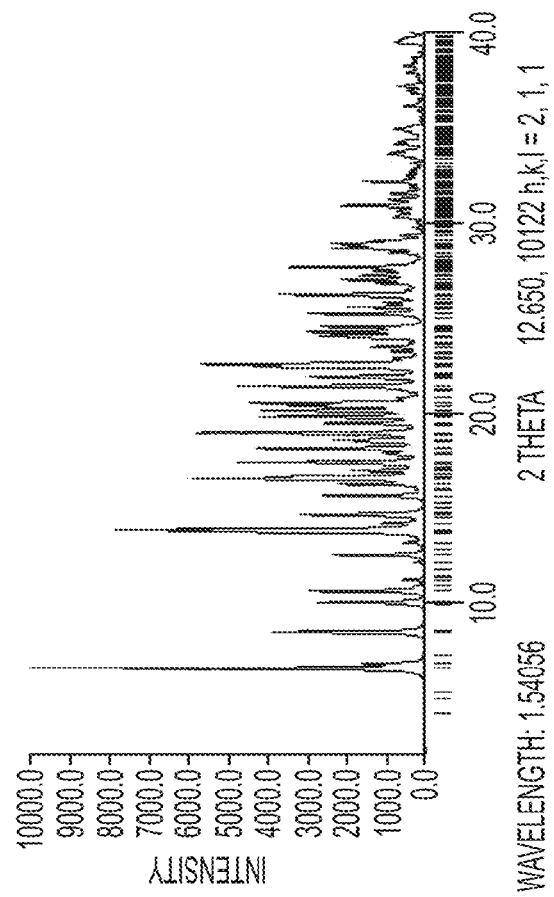
FIG. 34B shows the calculated X-ray diffraction profile of the single crystal.
Figure 34A:
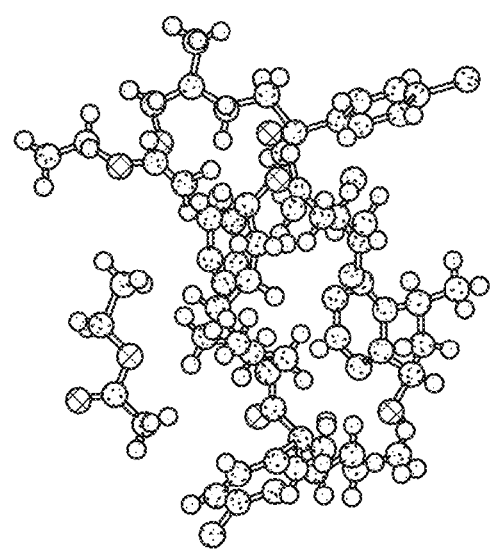
FIG. 34A shows the single crystal structure for the ethyl acetate solvate of a compound of formula I.
Figure 35:
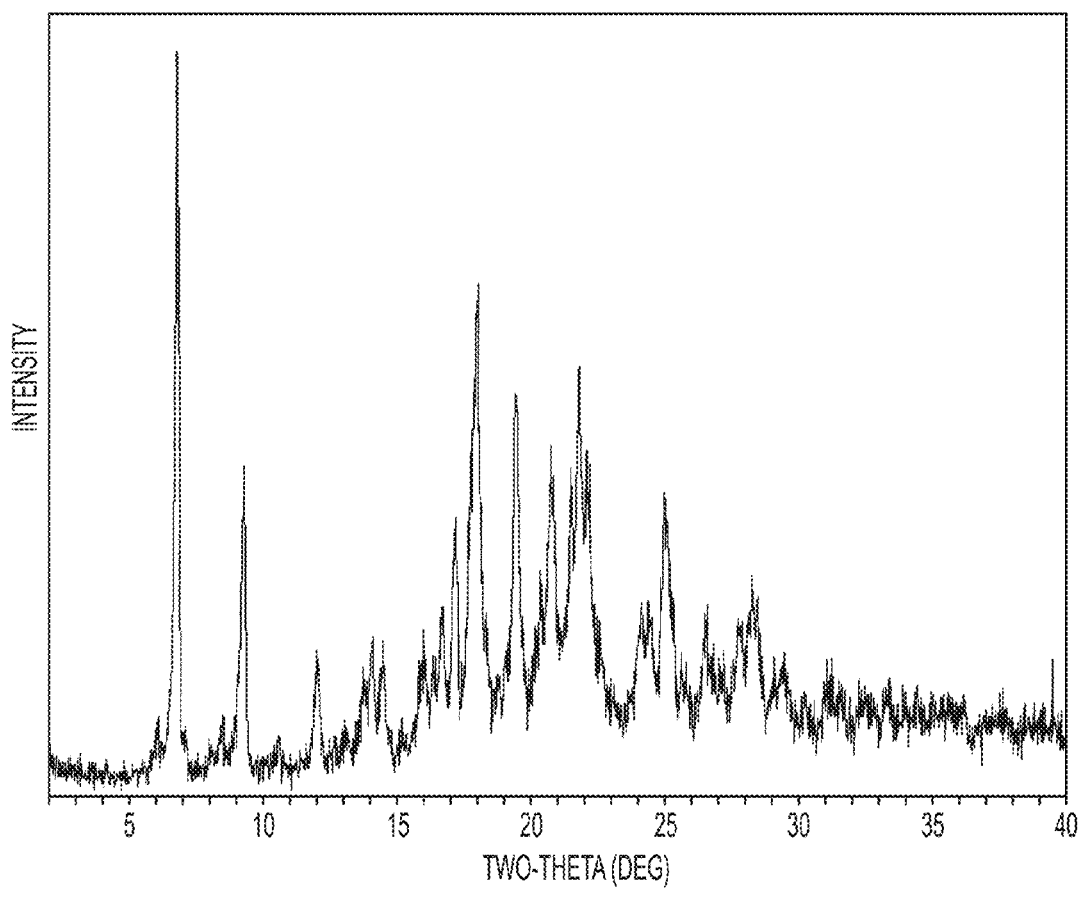
FIG. 35 shows the XRPD profile of ethylbenzene solvate of compound of formula I.
Figure 36:
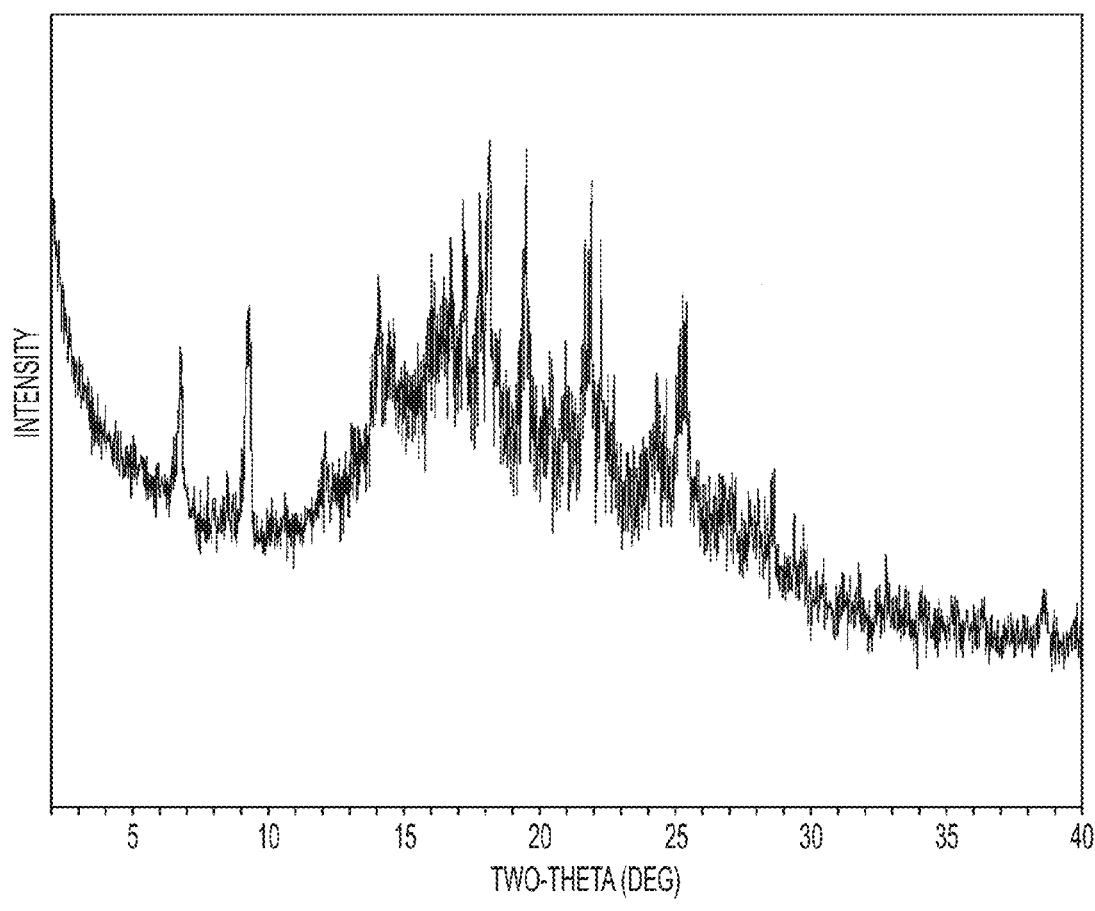
FIG. 36 shows the XRPD profile of ortho-xylene solvate of compound of formula I.
Figure 37:
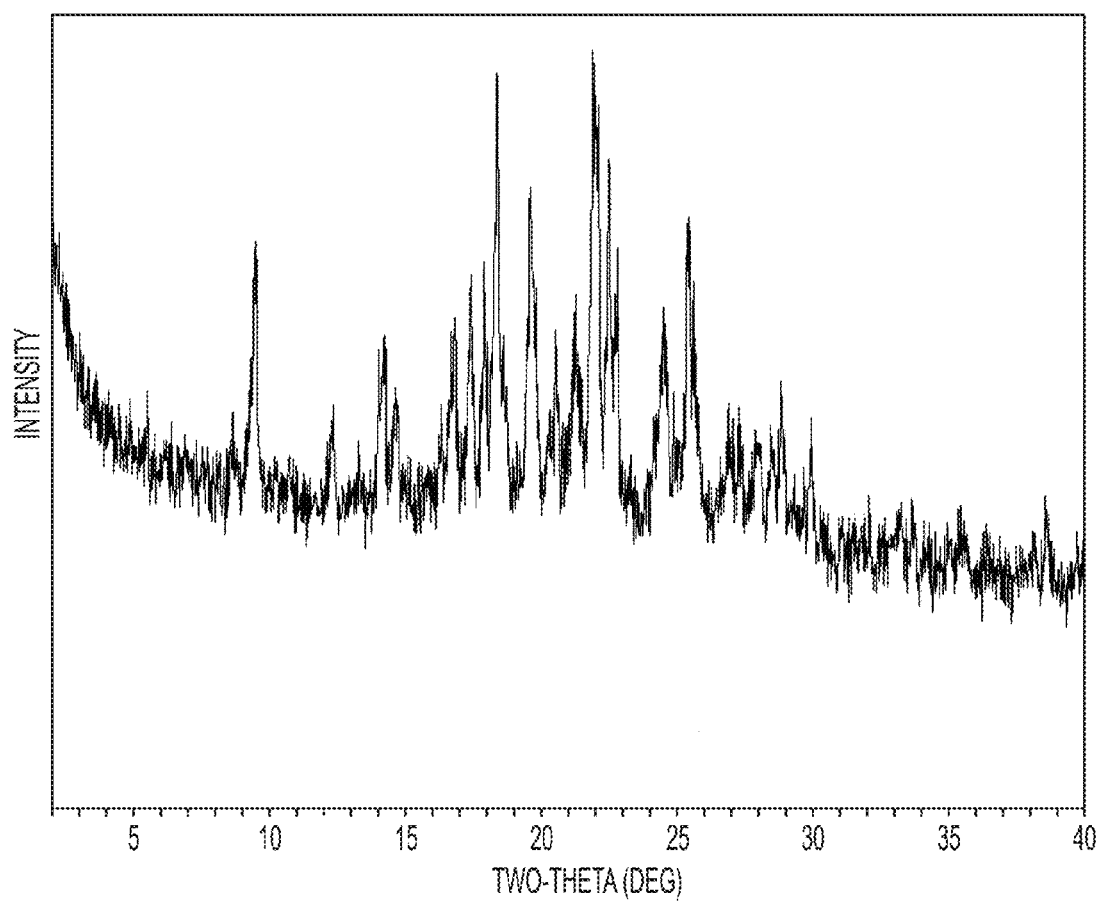
FIG. 37 shows the XRPD profile of meta-xylene solvate of compound of formula I.
Figure 38:
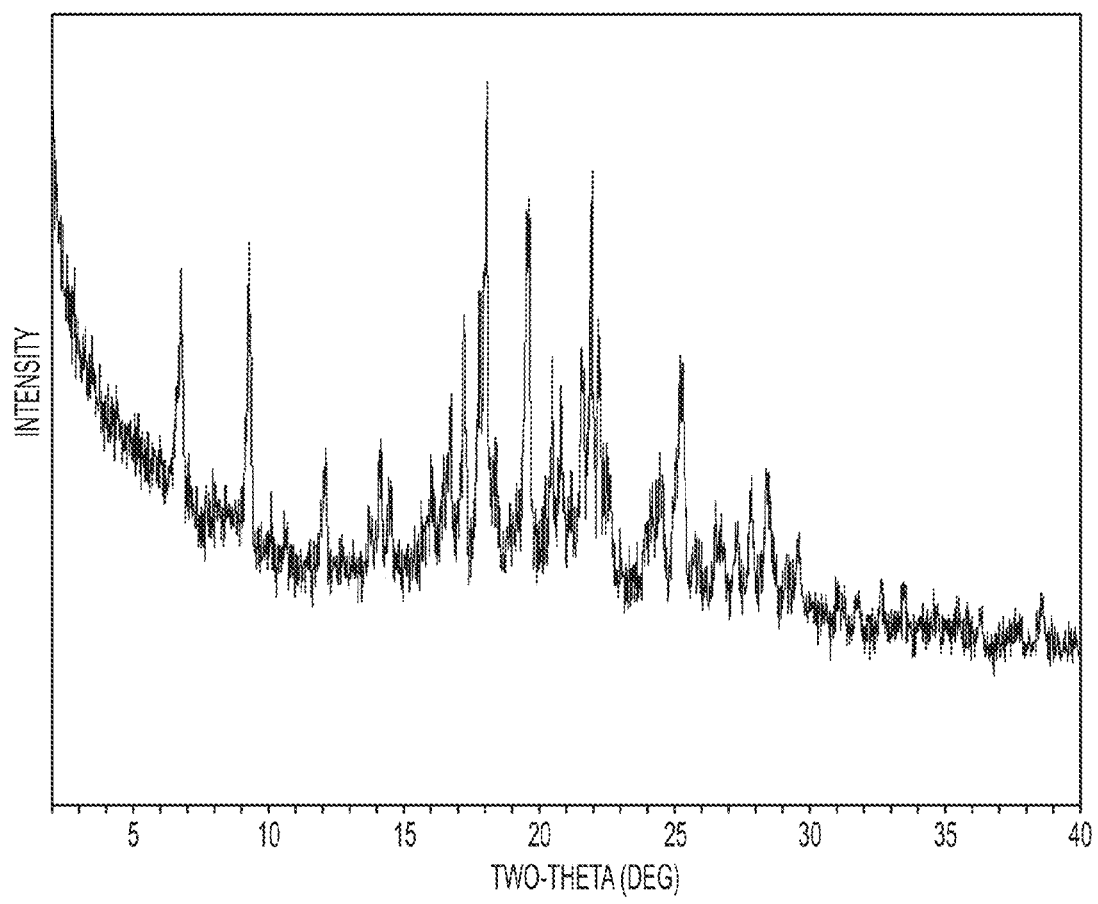
FIG. 38 shows the XRPD profile of para-xylene solvate of compound of formula I.
Figure 39:
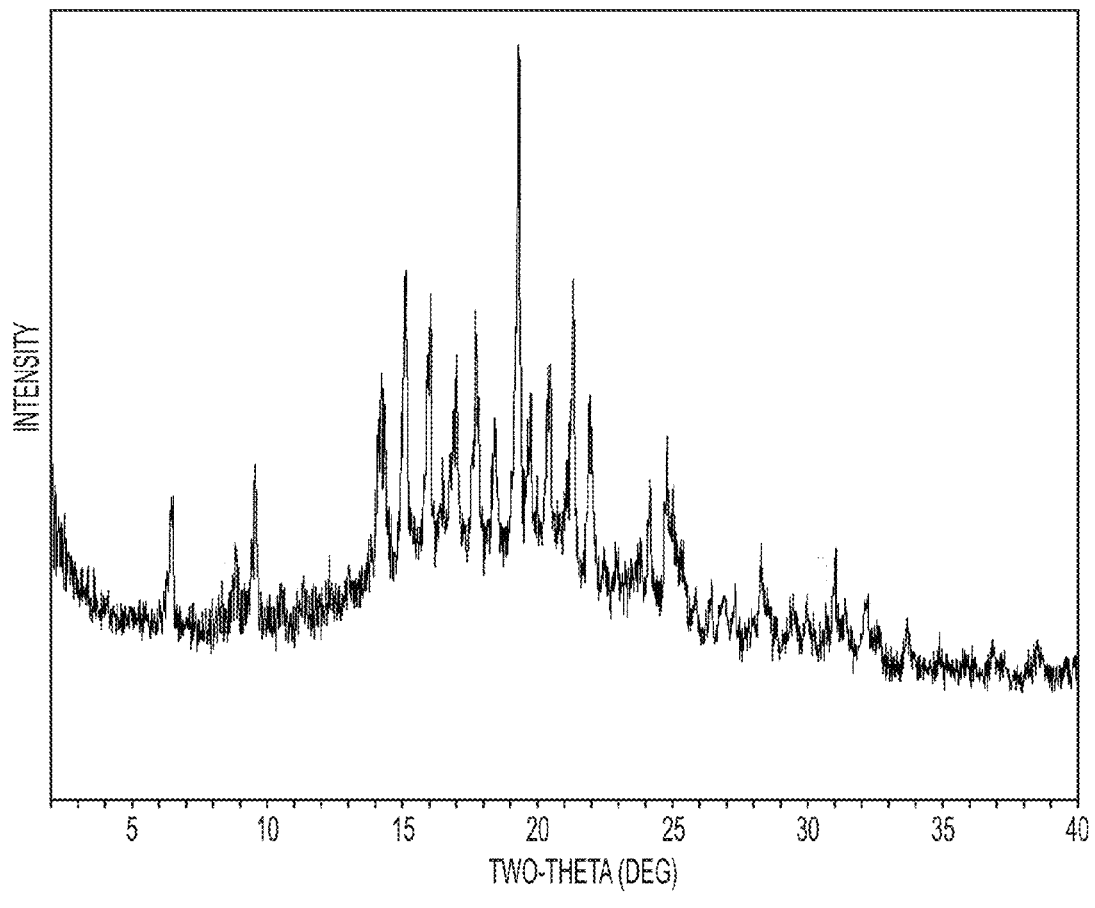
FIG. 39 shows the XRPD profile of cumene solvate of compound of formula I.
Figure 40:
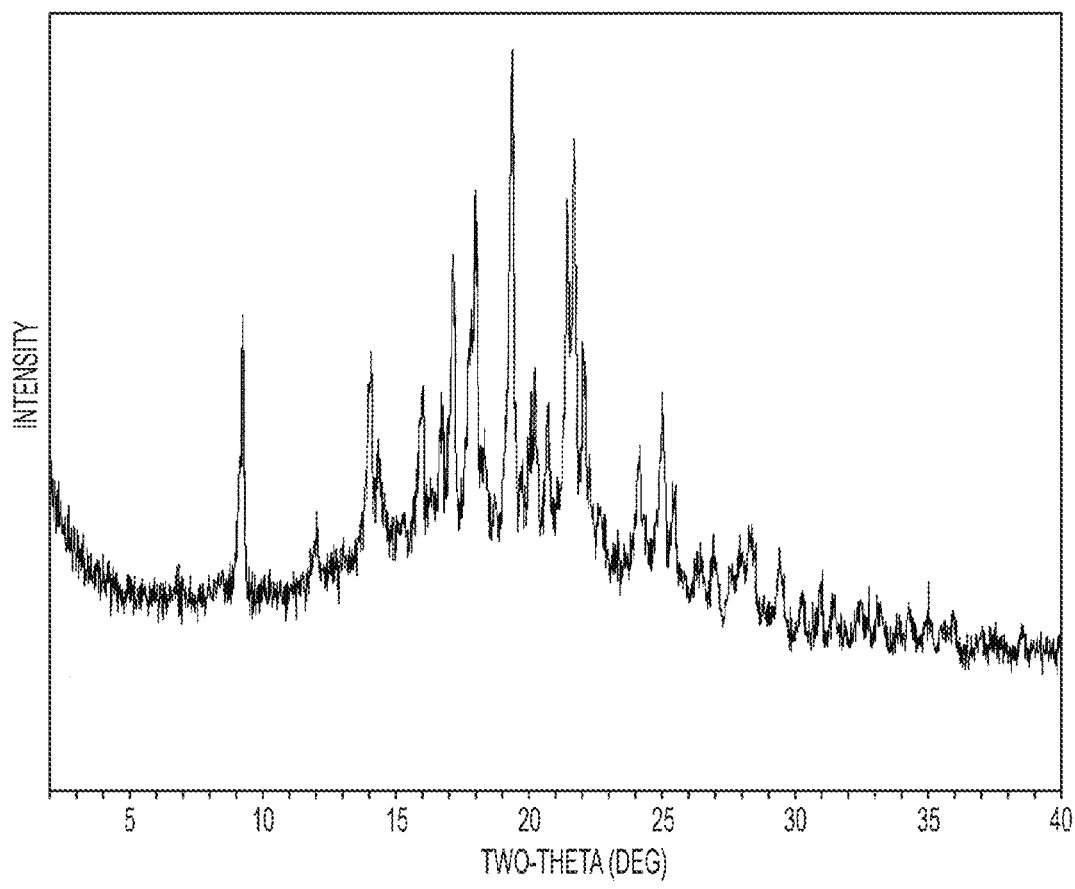
FIG. 40 shows the XRPD profile of tetralin solvate of compound of formula I.
Figure 41:
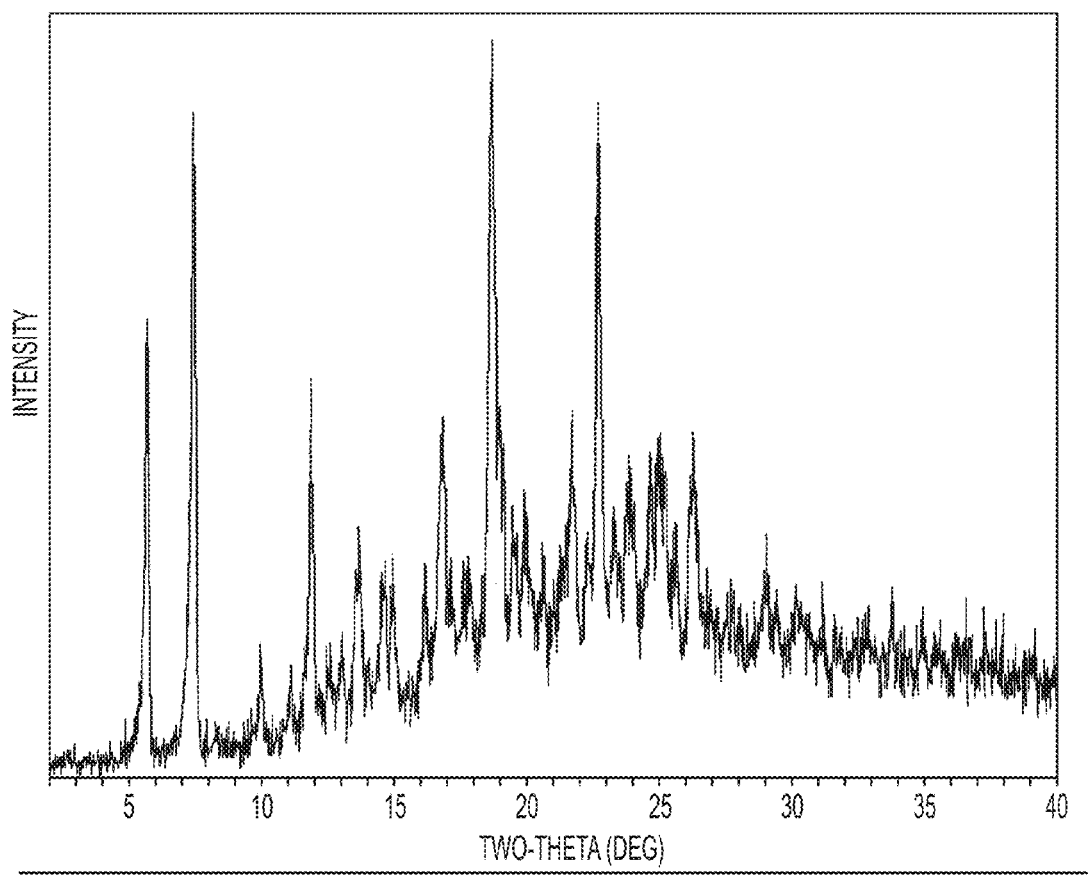
FIG. 41 shows the XRPD profile of MEK solvate of compound of formula I.
Figure 42:
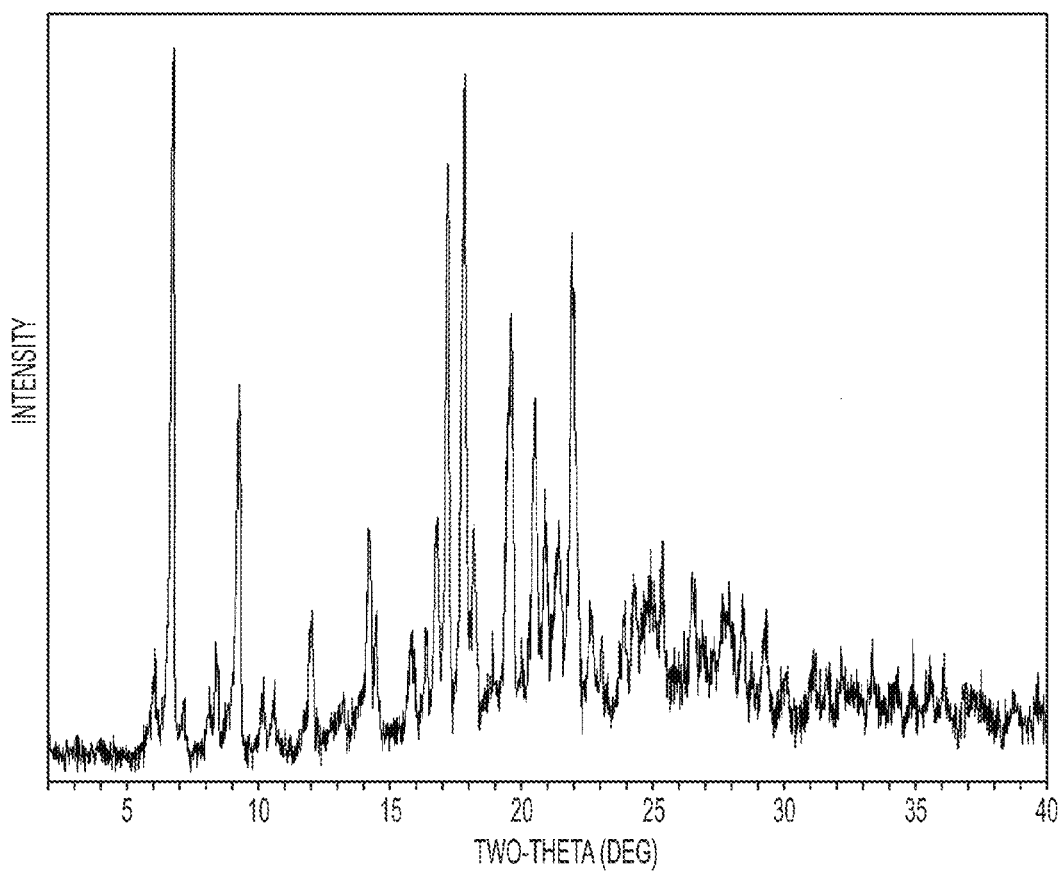
FIG. 42 shows the XRPD profile of MIBK solvate of compound of formula I.
Figure 43:
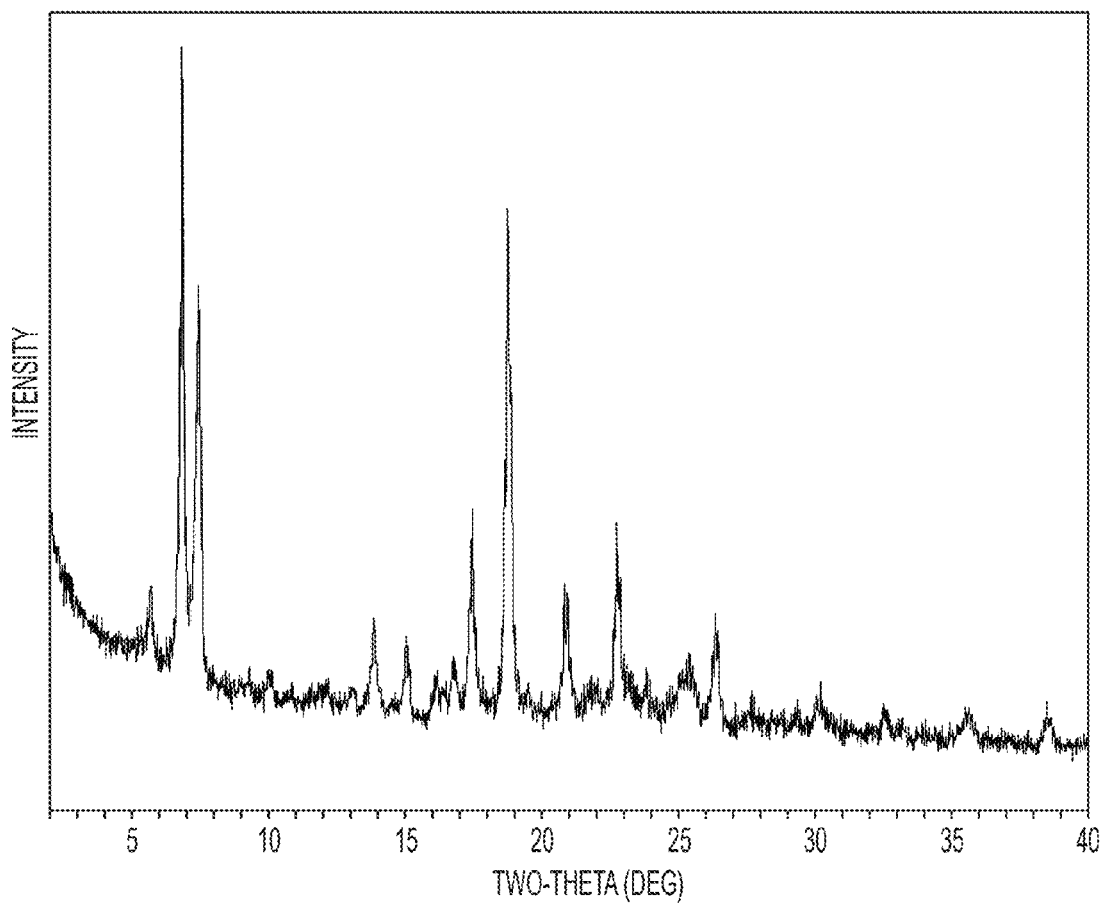
FIG. 43 shows the XRPD profile of MBK solvate of compound of formula I.
Figure 44:
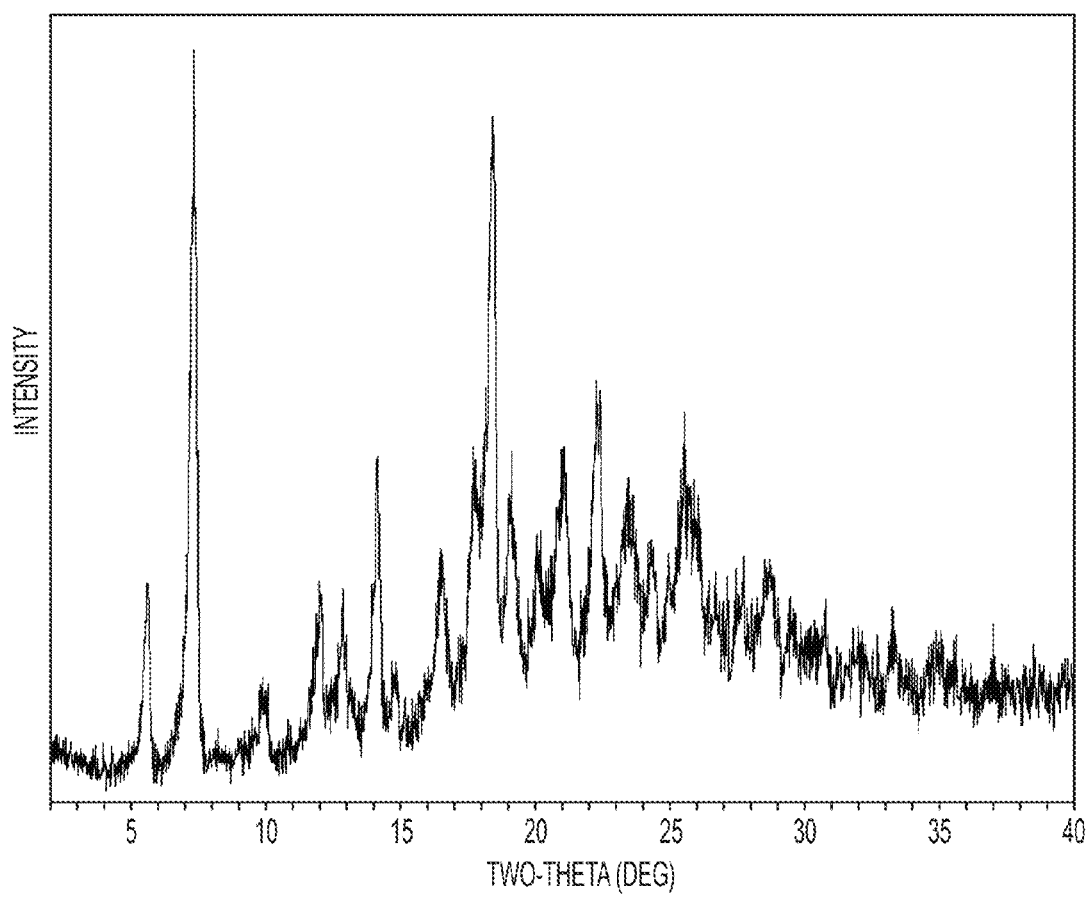
FIG. 44 shows the XRPD profile of diisobutylketone solvate of compound of formula I.
Figure 45:
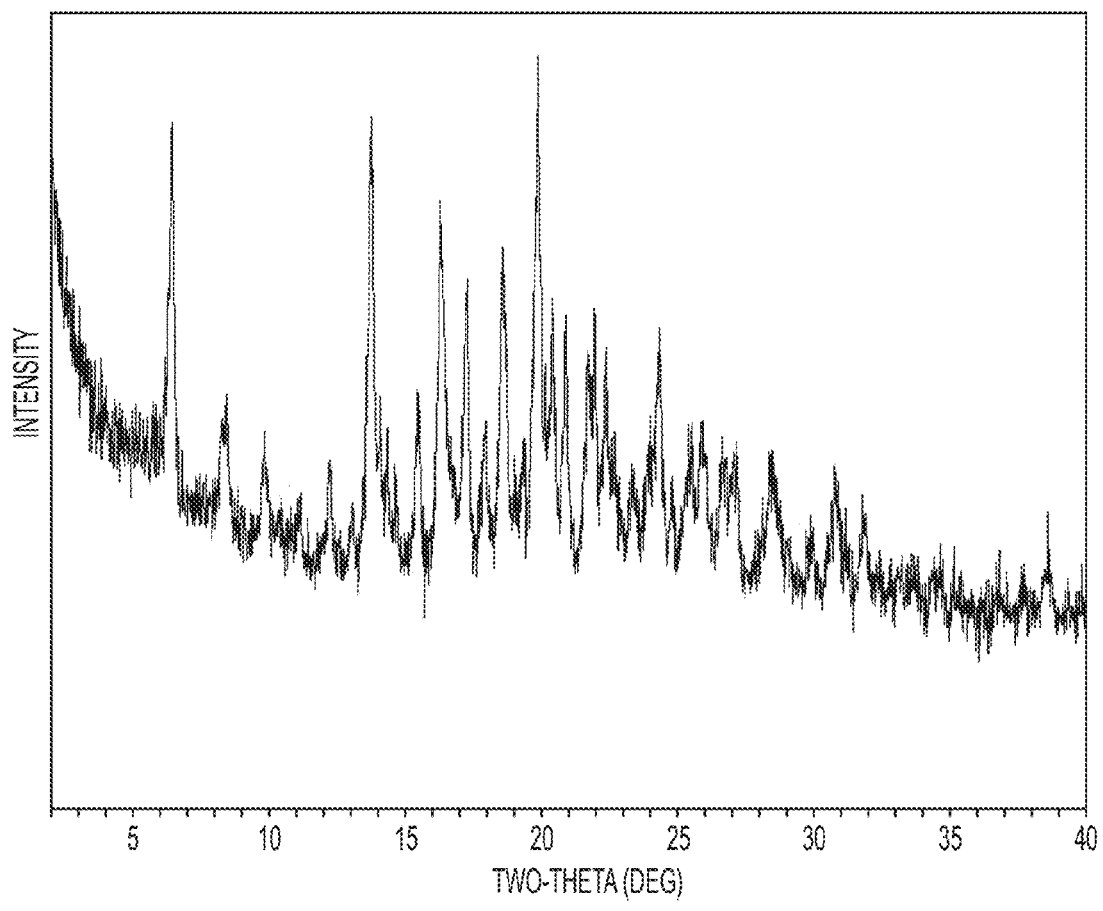
FIG. 45 shows the XRPD profile of methyl acetate solvate of compound of formula I.
Figure 46:
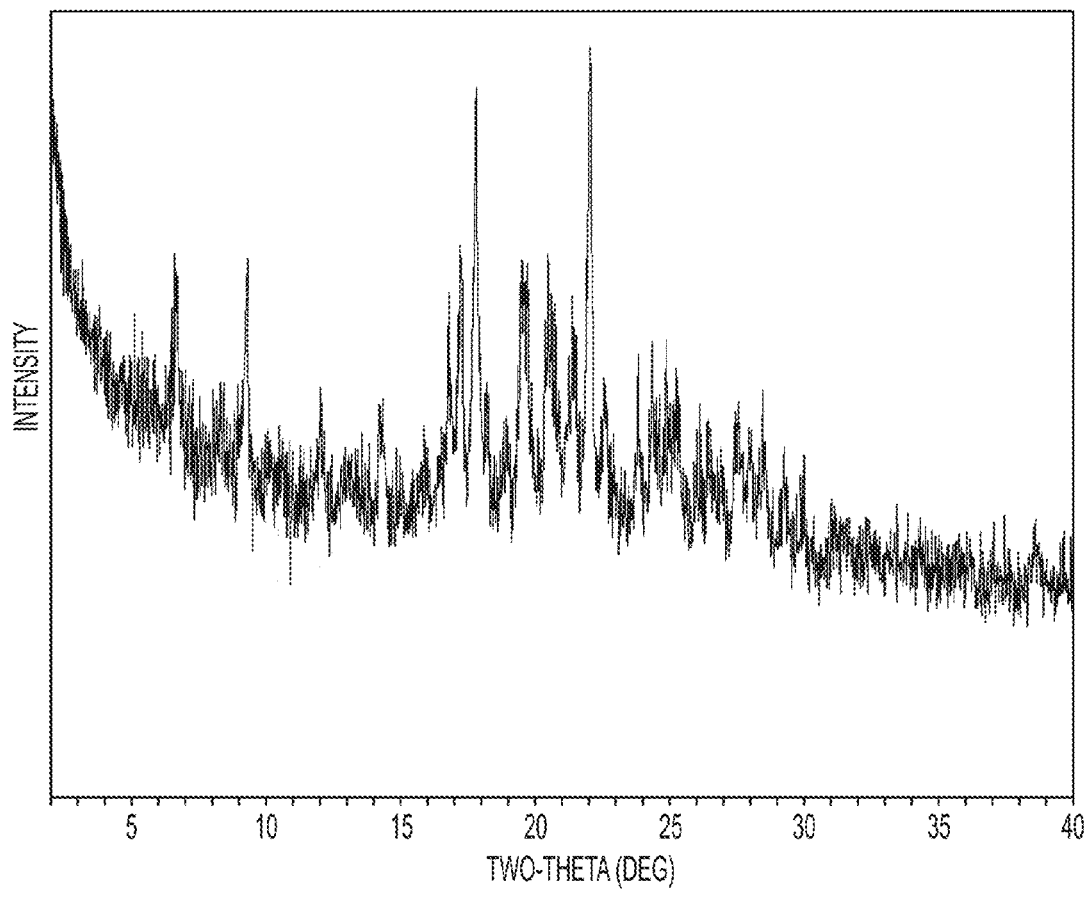
FIG. 46 shows the XRPD profile of propyl acetate solvate of compound of formula I.
Figure 47:
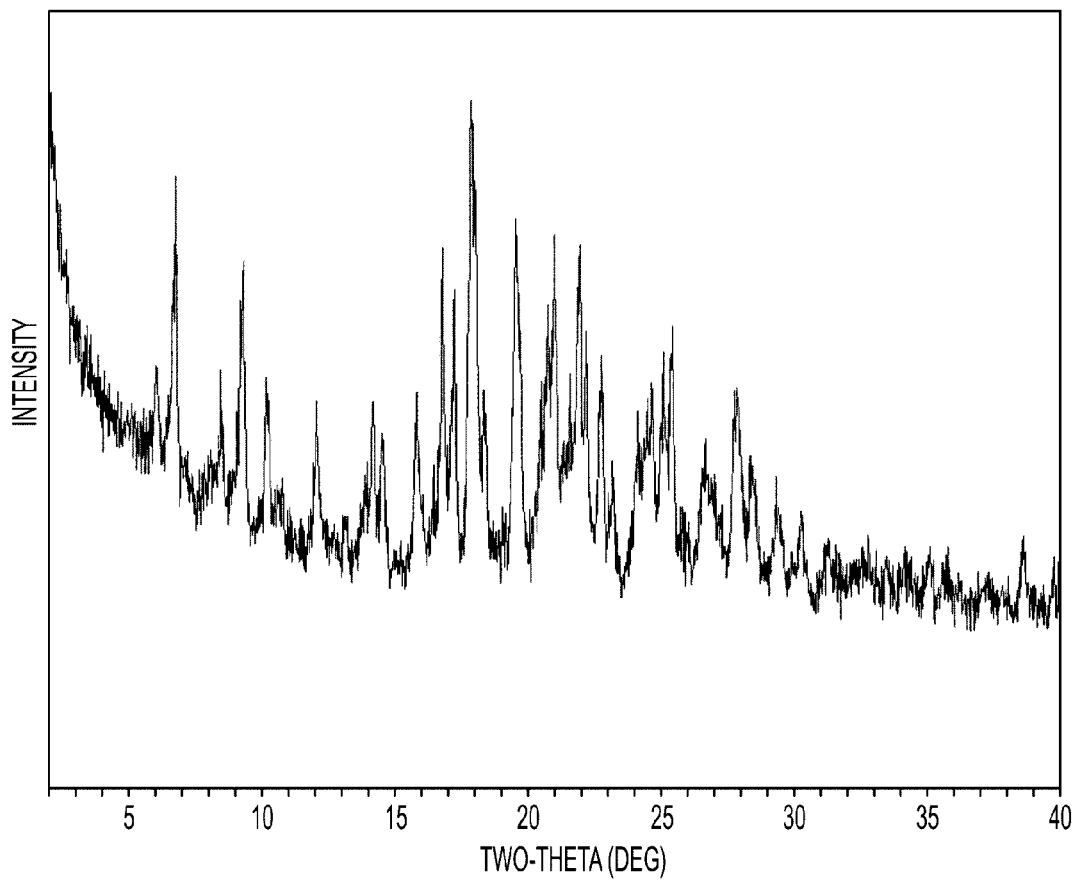
FIG. 47 shows the XRPD profile of isopropyl acetate solvate of compound of formula I.
Figure 48:
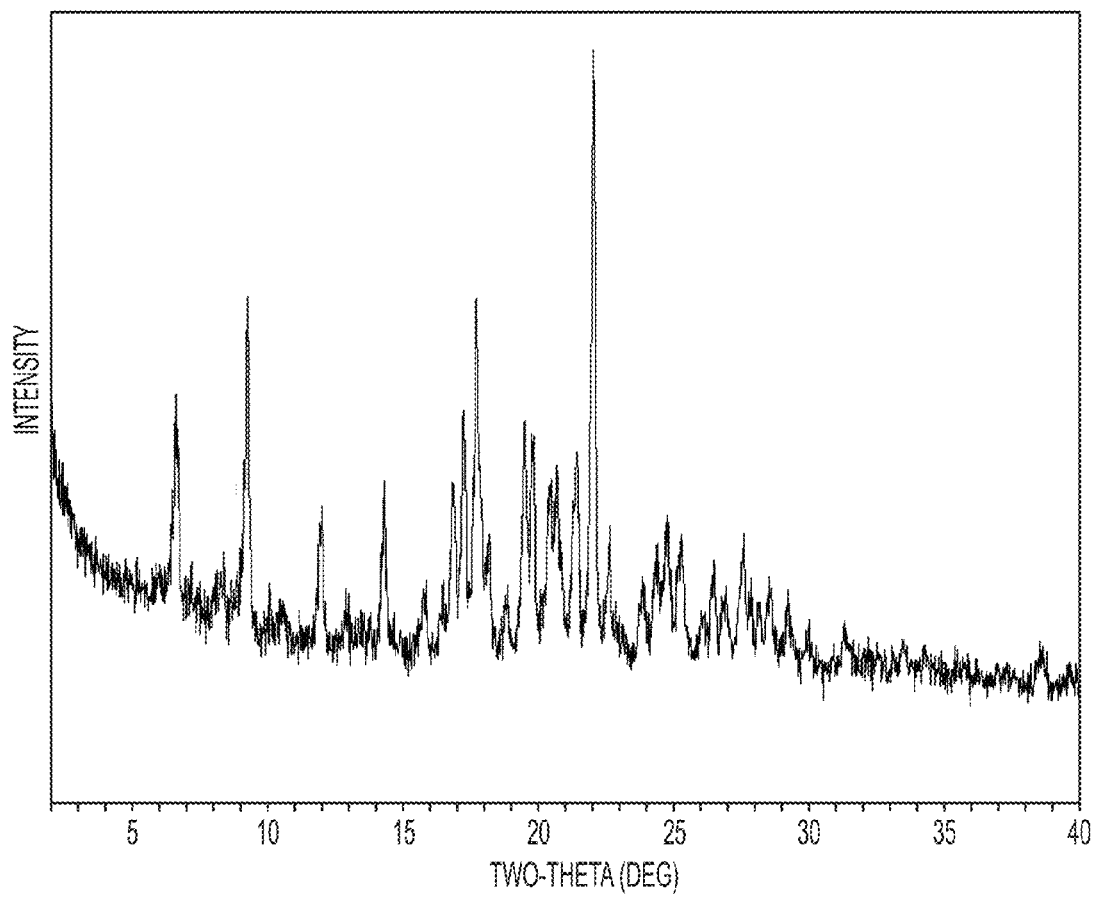
FIG. 48 shows the XRPD profile of isobutyl acetate solvate of compound of formula I.
Figure 49:
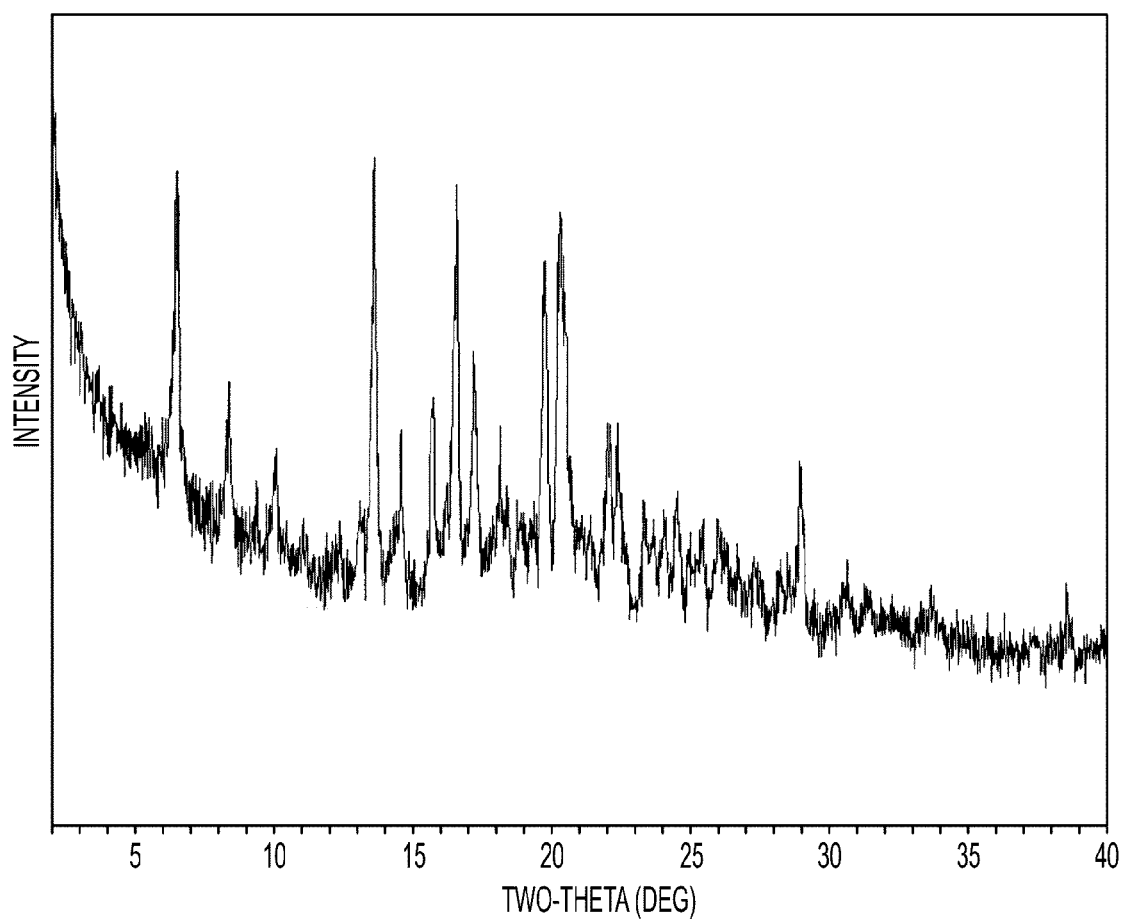
FIG. 49 shows the XRPD profile of t-butyl acetate solvate of compound of formula I.
Figure 50:
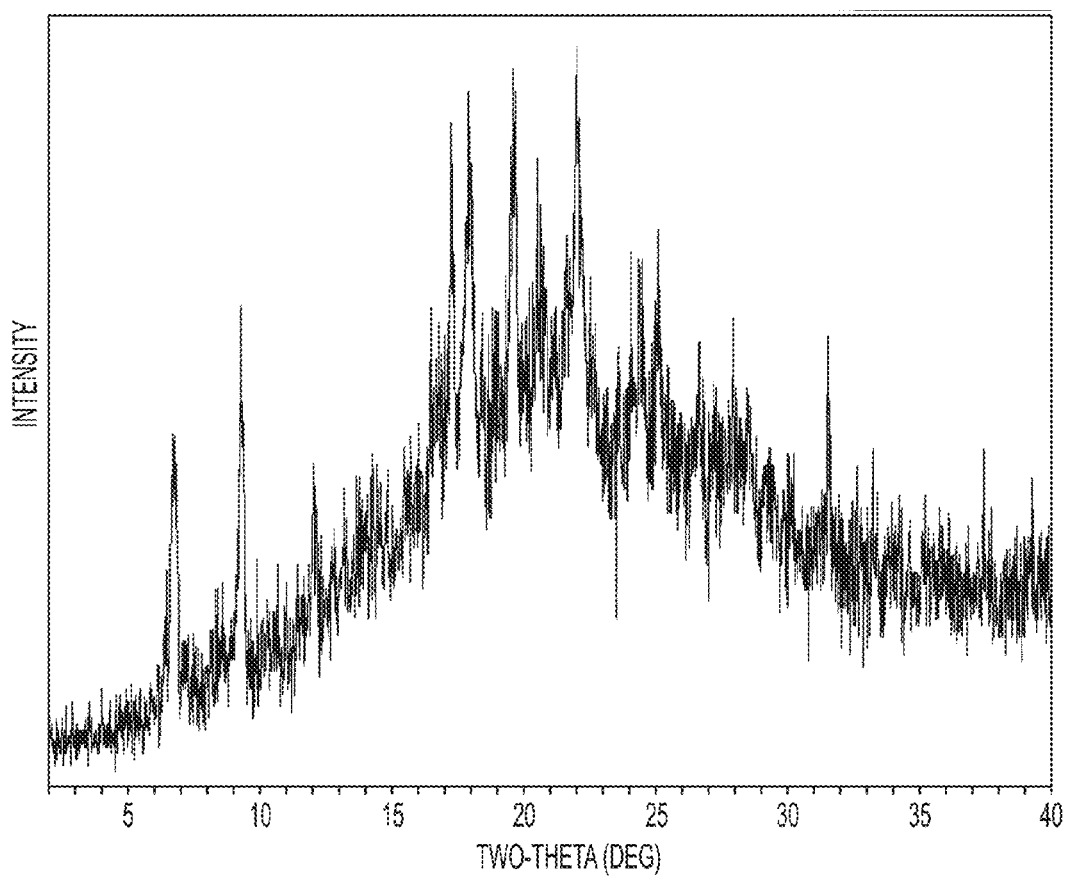
FIG. 50 shows the XRPD profile of ethyl ether solvate of compound of formula I.
Figure 51:
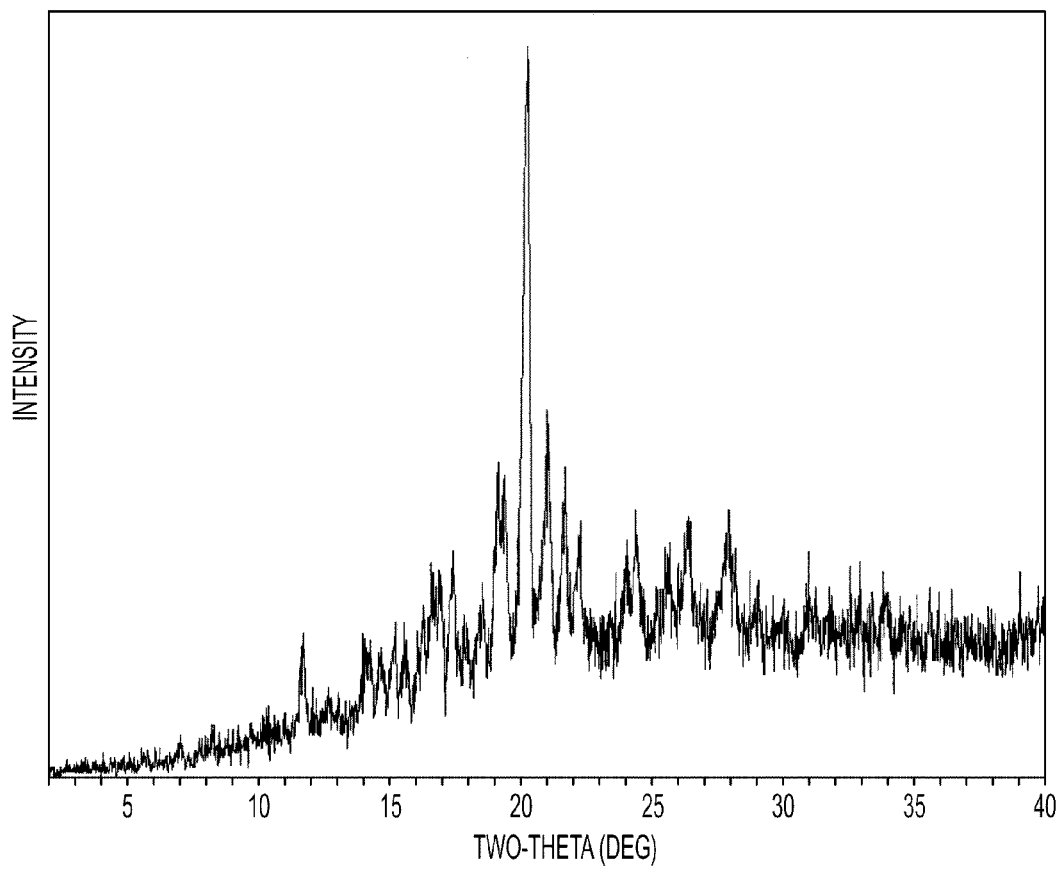
FIG. 51 shows the XRPD profile of amyl acetate solvate of compound of formula I.
Figure 52:
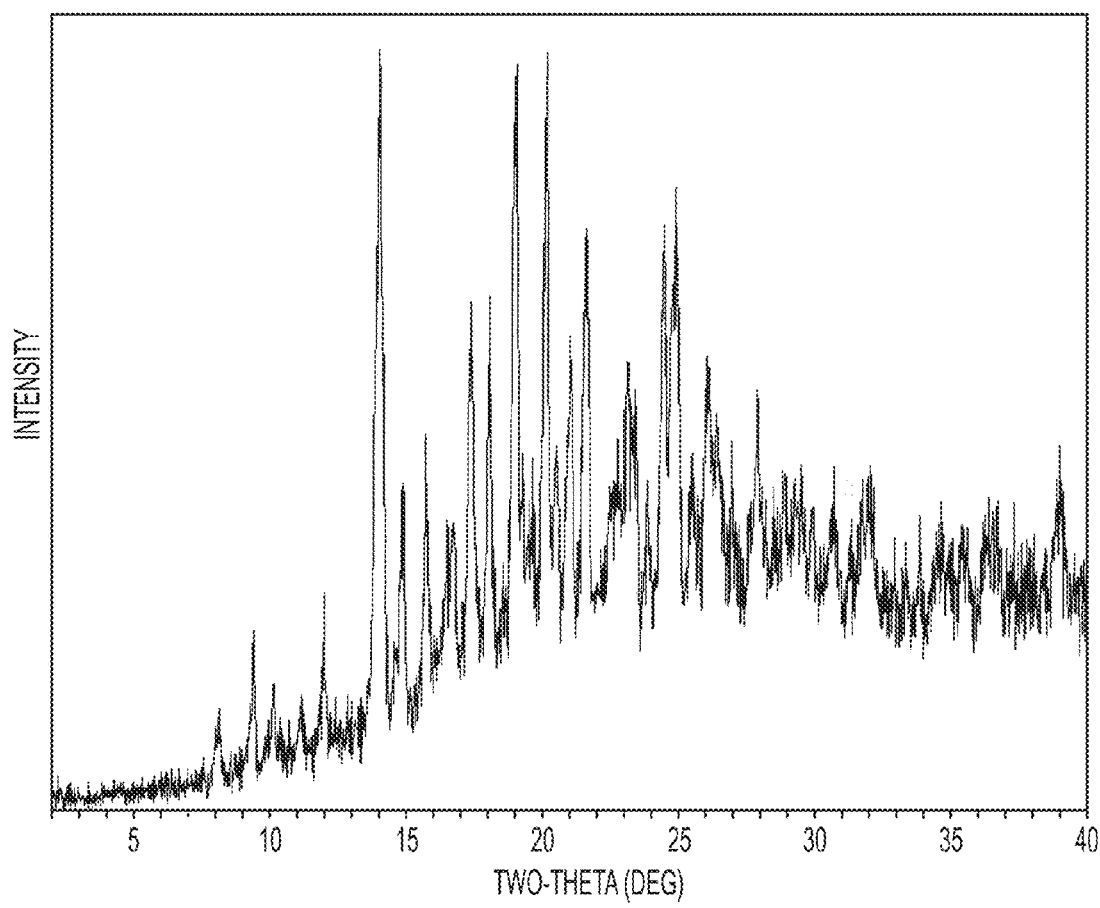
FIG. 52 shows the XRPD profile of glycerol triacetate solvate of compound of formula I.
Figure 53:
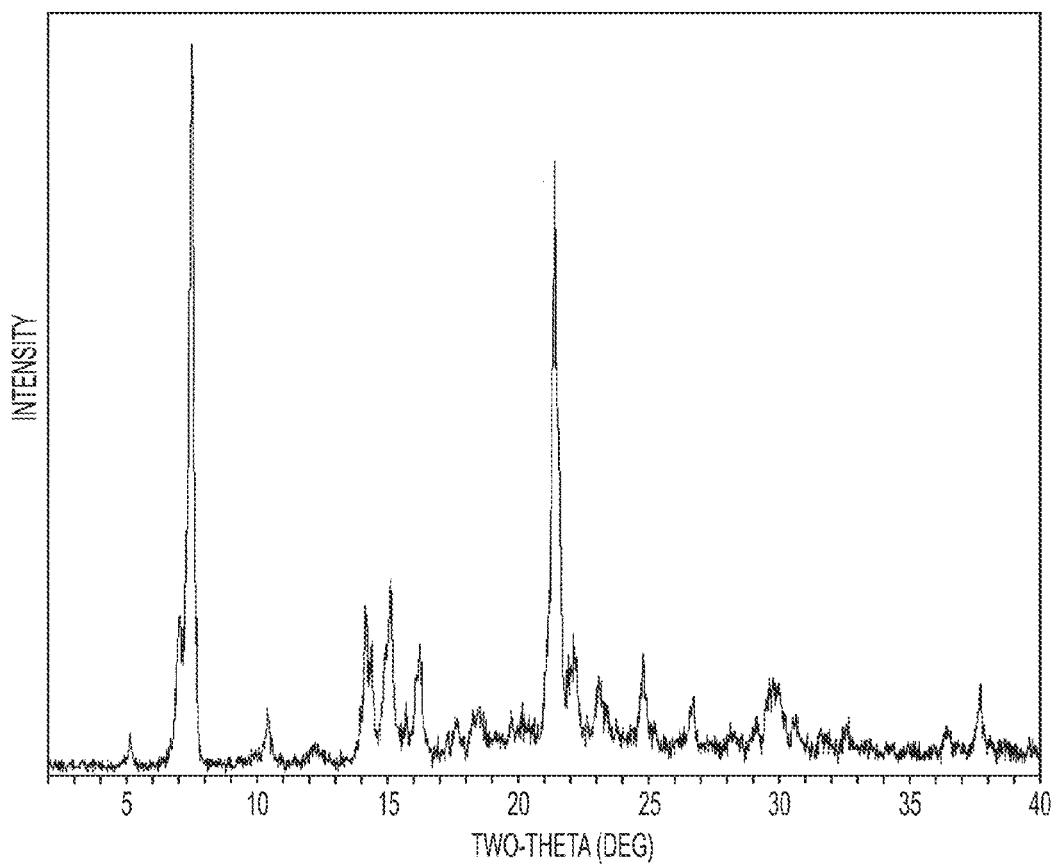
FIG. 53 shows the XRPD profile of ethyl ether ethanol hydrate solvate of compound of formula I.
Figure 54:
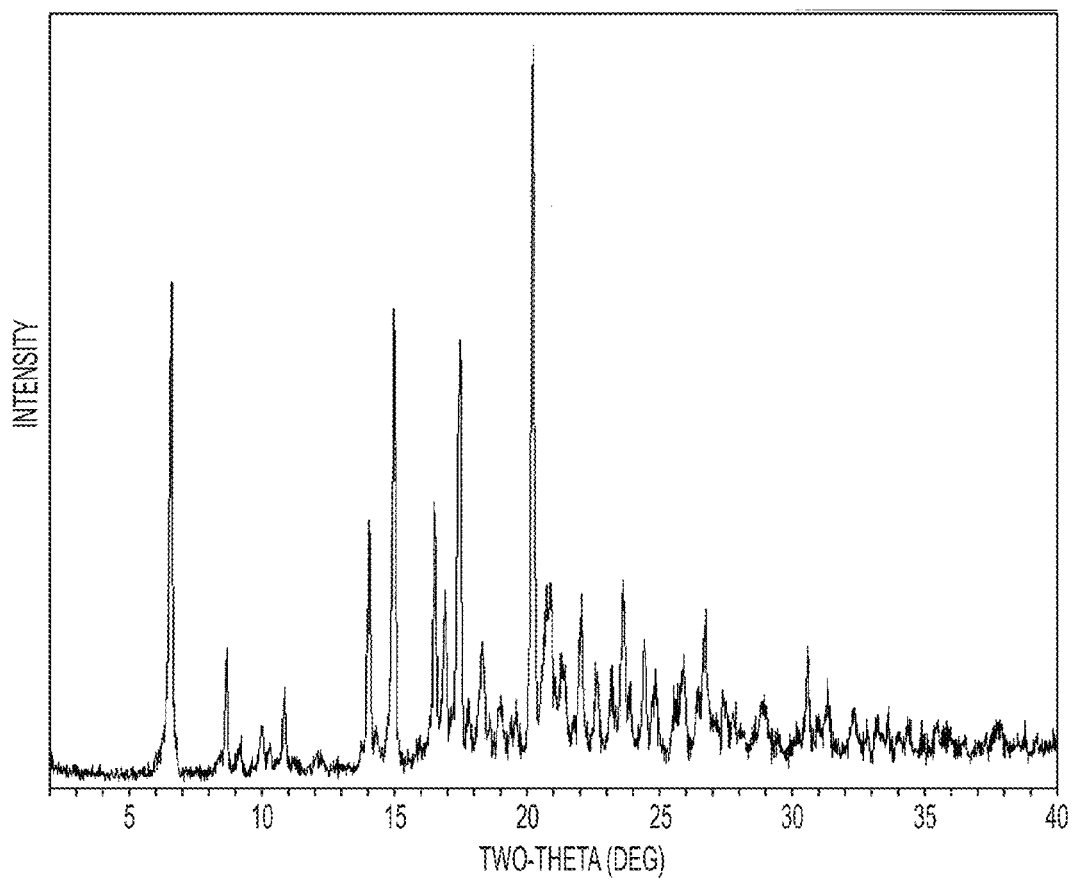
FIG. 54 shows the XRPD profile of t-butyl methyl ether solvate of compound of formula I.
Figure 55:
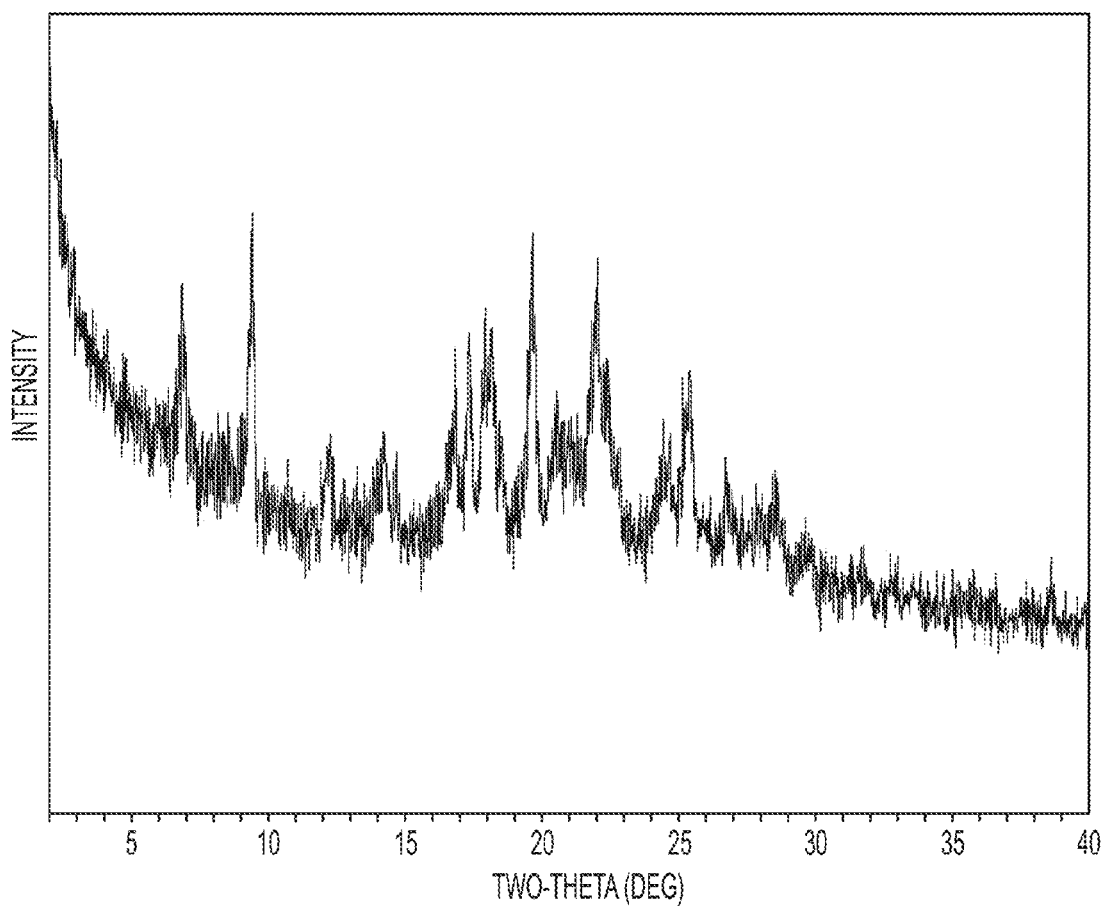
FIG. 55 shows the XRPD profile of dimethoxy ethane solvate of compound of formula I.
Figure 56:
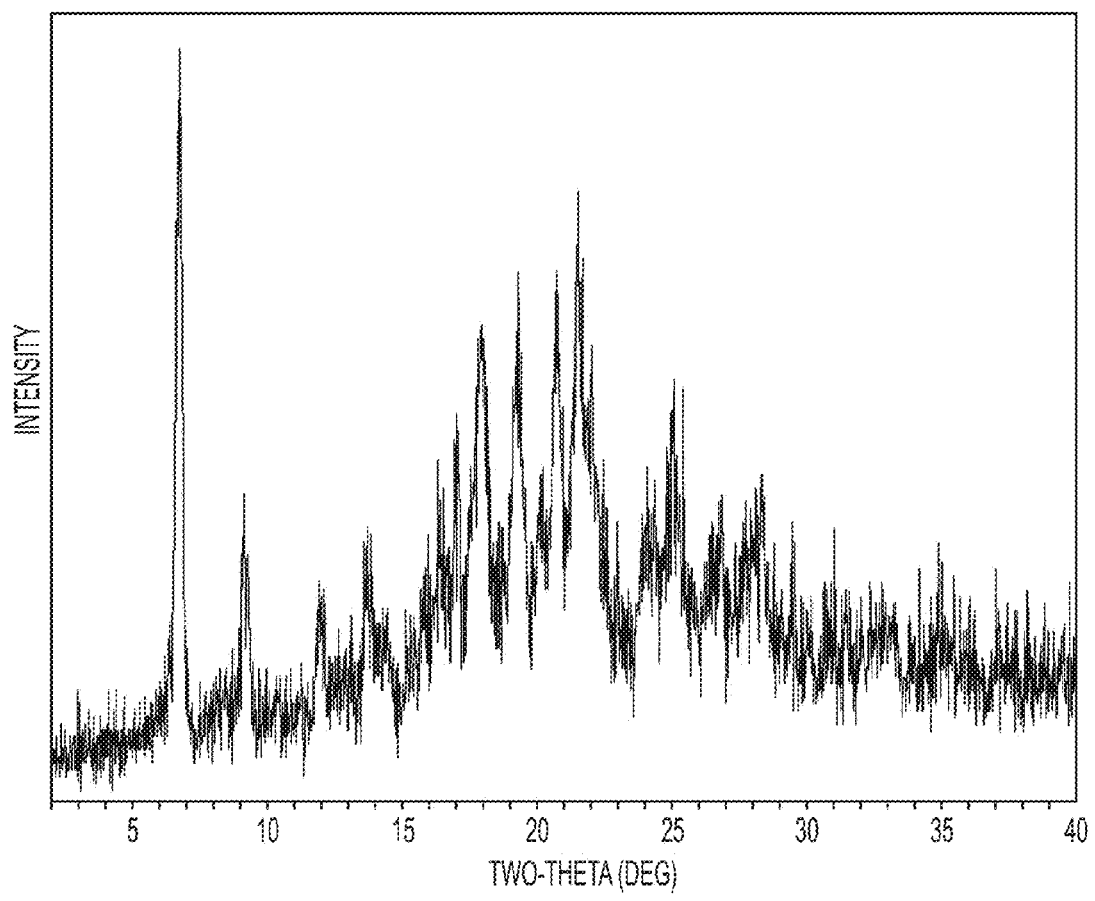
FIG. 56 shows the XRPD profile of diethoxy ethane solvate of compound of formula I.
Figure 57:
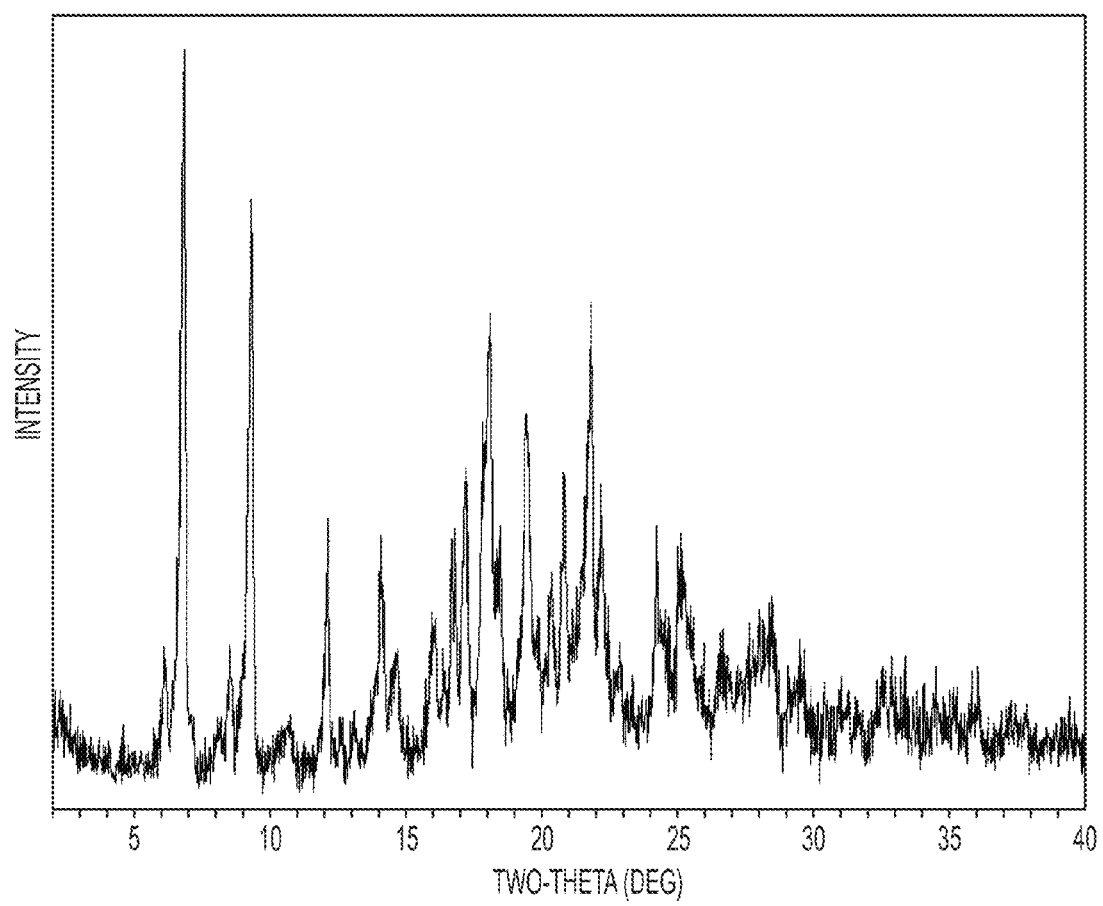
FIG. 57 shows the XRPD profile of dimethoxy propane solvate of compound of formula I.
Figure 58:
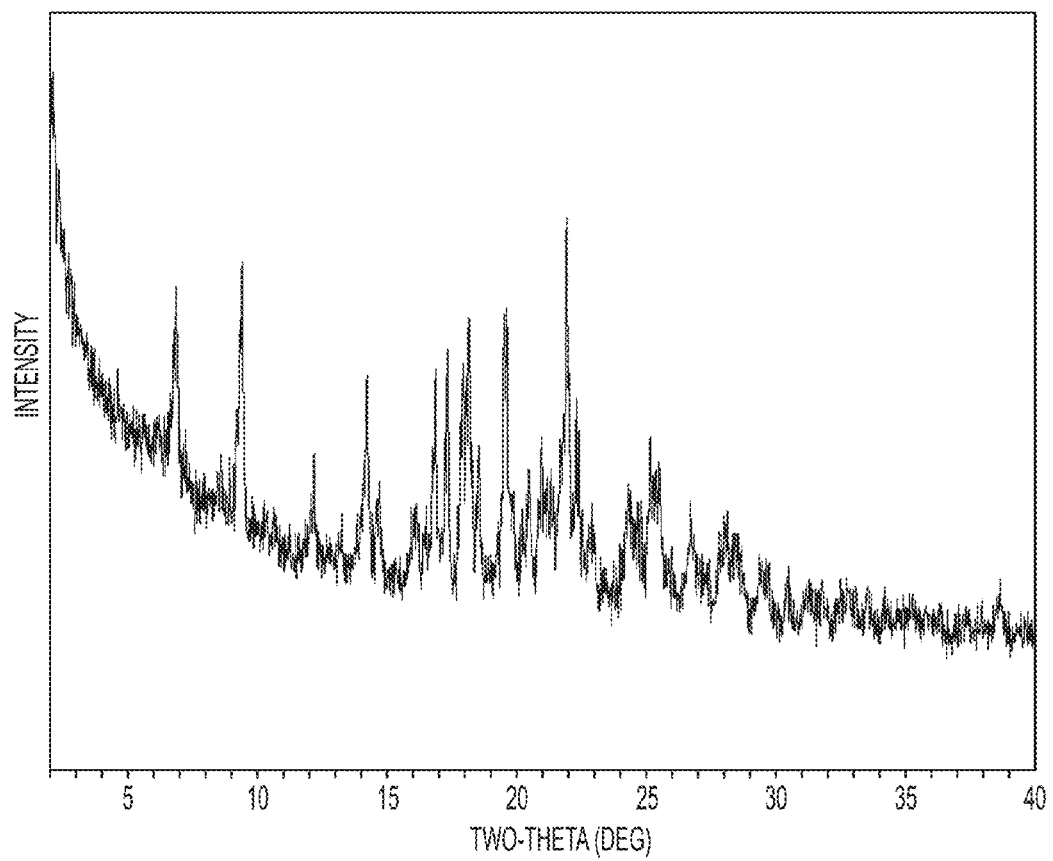
FIG. 58 shows the XRPD profile of 2-methyl tetrahydrofuran solvate of compound of formula I.

A saturated solution of material from Example 1 was prepared by slurrying material from Example 1 in ethyl acetate at 50° C. overnight and then filtering through a hot, 50° C., syringe filter fitted with a 0.45 μm filter while the slurry was still hot. The resulting solution was allowed to slowly cool to room temperature in a sealed vial and allowed to stand for 2 weeks. Crystals of suitable quality for structure determination were formed (See FIG. 34). and the data is shown in Table 5 below.

TABLE 5

| formula | $C_{28}H_{41}Cl_2N_5O_4$ |
| --- | --- |
| formula weight | 582.58 |
| space group | P 21 21 21 (No. 19) |
| a, Å | 16.5805(3) |
| b, Å | 17.6134(3) |
| c, Å | 20.7419(15) |
| V, Å$^3$ | 6057.4(5) |
| Z | 8 |
| $d_{calc}$, g cm$^{-3}$ | 1.278 |
| temperature, K | 150 |
| radiation (wavelength, Å) | Cu K$_\alpha$ (1.54184) |
| diffractometer | Rigaku RAPID-II |
| h, k, l range | −17 to 19 −11 to 20 −17 to 24 |
| θ range, deg | 4.26-133.19 |
| programs used | SHELXTL 2008 |
| data collected | 10507 |
| R(F$_o$) | 0.053 |
| R$_w$(F$_o^2$) | 0.108 |
| goodness of fit | 1.115 |
| absolute structure determination | Flack parameter (0.00(2)) |

Additional solvates: Chlorobenzene solvate: Chlorobenzene, approximately 2 mL, was added to material from Example 1, 66 mg. The slurry was heated to 50 C in a shaker block for 1 day. The solid dissolved. The solution was cooled to room temperature, placed in a freezer at approximately −18 C and allowed to stand for 24 days. Solid appeared. The solution was decanted while still cold to remove most of the solvent to give crystals of the chlorobenzene solvate.

Ethylbenzene solvate: Ethyl benzene, 5 mL, was added to material from example 1, 29 mg. The slurry was heated to 50 C on a shaking block for 2 days. The slurry was allowed to cool to room temperature and allowed to stand for 1 week to give the ethylbenzene solvate of compound of formula I. Solids were collected by filtration and analyzed while wet with solvent.

ortho-Xylene solvate: ortho-Xylene, 4 mL, was added to material from example 1, 66 mg. The slurry was heated to 50 C for 2 days and then cooled to room temperature and allowed to stand for 6 days at room temperature. Solid was pulled from the slurry and analyzed without drying. The suspension was allowed to stand for about 1 month. A second sample was collected by filtering the suspension and analyzing the solid was still damp with solvent to give the ortho-xylene solvate of compound of formula I.

meta-Xylene solvate: meta-Xylene, 3 mL, was added to material from example 1, 64 mg. The slurry was heated to 50 C for 2 days and then cooled to room temperature and allowed to stand for 12 days at room temperature. A sample was collected by filtering the suspension and analyzing the solid was still damp with solvent to give the meta-xylene solvate of compound of formula I. meta-Xylene, 5 mL, was added to material from example 1.24 mg. The slurry was heated to 50 C for 2 days and then cooled to room temperature and allowed to stand for 15 days at room temperature. A sample was collected by filtering the suspension and analyzing the solid was still damp with solvent to give the meta-xylene solvate of compound of formula I.

para-Xylene solvate: para-Xylene, 4 mL, was added to material from example 1, 81 mg. The slurry was heated to 50 C for 2 days and then cooled to room temperature and allowed to stand for 6 days at room temperature. A sample was collected by filtering the suspension and analyzing the solid was still damp with solvent to give the para-xylene solvate of compound of formula I.

Cumene solvate: Cumene, 2 mL, was added to material from example 1.64 mg. The slurry was heated to 50 C for 2 days and then cooled to room temperature and allowed to stand for 11 days at room temperature. A sample was collected by filtering the suspension and analyzing the solid was still damp with solvent to give the cumene solvate of compound of formula I.

Tetralin solvate: Tetralin, 3 mL, was added to material from example 1.64 mg. The slurry was heated to 50 C for 2 days and then cooled to room temperature and allowed to stand for 12 days at room temperature. A sample was collected by removing solid with a spatula from the suspension and analyzing the solid was still wet with solvent to give the tetralin solvate of compound of formula I.

Methyl ethyl ketone solvate: Methyl ethyl ketone (1 mL) was added to the amorphous material (222.7 mg). The material was sonicated at 28° C. for 5 minutes. The solid almost dissolved after 2 minutes. The sample was removed from the sonication bath and became cloudy prior to becoming a mass of solid with no visible solvent present. Methyl ethyl ketone (100 μL) was added to the amorphous material (22.2 mg). The solid dissolved. Heptane (100 μL) was added along with a seed of amorphous material. The material was slurried for 4 days and the solid isolated while still damp with solvent to give the MEK solvate.

Methyl isobutyl ketone solvate: Methyl isobutyl ketone, 1 mL, was added to solid from example 1, 32.3 mg. The slurry was heated to 50 C for 2 days on a shaking block and then allowed to stand at room temperature for 15 days. Sample was collected by filtering the suspension and analyzing the solid while the solid was still damp with solvent to give the methyl isobutyl ketone solvate of compound of formula I.

Methyl Butyl ketone solvate: Methyl butyl ketone, 3 mL, was added to material from example 1.63 mg. The solid dissolved. The solution was placed in a freezer at approximately −18 C and allowed to stand for 25 days. Solid appeared. The solution was decanted while still cold to remove most of the solvent to give crystals of the methyl butyl ketone solvate. The solid was initially analyzed by removing a solid aliquot from the suspension with a spatula. The solid was reanalyzed by collecting solid via filtration and analyzing the solid while still damp with solvent.

Diisobutyl ketone: A solution of diisobutyl ketone and isopropanol (90:10 v:v ratio) was added to the HCl salt at a concentration of 50 mg HCl salt to solvent. The solids dissolved and more HCl salt was added to give a slurry. A pasty solid was isolated after were stirred at room temperature. The material was dried at 50° C. under vacuum (50-100 torr) to give the diisobutyl ketone solvate.

Chloroform solvate hydrate: The HCl salt (2.63 mg) was treated with a mixture of heptane (2 mL) and chloroform (0.5 mL). The slurry was heated at 60° C. A cluster of solids, needles, were observed in the vial. The vial was allowed to stand for 23 days where most of the solvent had evaporated. A large plate was observed in the vial that was suitable for single crystal structure determination. The chloroform solvate hydrate was found to be partially desolvated and contained about 1 mole of chloroform and 0.25 mole of water per API molecule Methyl acetate solvate: Methyl acetate, 4 mL, was added to material from example 1, 24 mg. The solid dissolved. The solution was filtered into a 4 mL vial and the cap removed. The vial was placed inside a 20 mL scintillation vial containing heptane and the lid placed on the 20 mL vial. The vials were not disturbed. The solvents were allowed to diffuse into one another. Crystals suitable for structure determination were obtained. The crystal obtained contained 0.71 moles of methyl acetate/mole of compound of formula I and the solvent was disordered. Methyl acetate solvate: Methyl acetate, 2.5 mL, was added to solid from example 1, 111 mg. The slurry was heated to 50 C overnight on a shaking block and then allowed to stand at room temperature for 1 week. A sample was collected by filtering the suspension and analyzing the solid while the solid was still damp with solvent to give the methyl acetate solvate of compound of formula I.

Propyl acetate solvate: Propyl acetate, 6 mL, was added to material from example 1, 31 mg. The suspension was heated at 50° C. in a shaker block and then allowed to cool to room temperature. Crystals suitable for structure determination were obtained. Propyl acetate, 2 mL, was added to material from example 1. The slurry was heated to 50° C. overnight and allowed to stand for 1 week. Solid was collected by vacuum filtration and the solid collected while still damp with liquid to give the propyl acetate solvate.

Isopropyl acetate solvate: Isopropyl acetate, 1 mL, was added to material from example 1, 55 mg. The slurry was heated to 50 C for 2 days and then cooled to room temperature and allowed to stand for 15 days at room temperature. A sample was collected by filtering the suspension and analyzing the solid was still damp with solvent to give the isopropyl acetate of compound of formula I.

Isobutyl acetate solvate: Isobutyl acetate, 2 mL, was added to solid from example 1, 68 mg. The slurry was heated to 50 C for 2 days on a shaking block and then allowed to stand at room temperature for 2 weeks. Sample was collected by filtering the suspension and analyzing the solid while the solid was still damp with solvent to give the methyl isobutyl ketone solvate of compound of formula I.

Tert-butyl acetate solvate: Tert-butyl acetate, 2 mL, was added to solid from example 1.63 mg. The slurry was heated to 50 C for 2 days on a shaking block and then allowed to stand at room temperature for 2 weeks. Sample was collected by filtering the suspension and analyzing the solid while the solid was still damp with solvent to give the methyl isobutyl ketone solvate of compound of formula I.

Ethyl ether solvate: (69659-50) Material from example 1 was dissolved in ethanol and the solvent removed under reduced pressure on a rotary evaporator to give amorphous material. The solid was slurried for 22 days at room temperature. Sample was collected by filtering the suspension and analyzing the solid while the solid was still damp with solvent to give the ethyl ether solvate of compound of formula I.

Amyl acetate solvate: A solution of amyl acetate and isopropanol (95:5 v:v ratio) was added to the HCl salt contained in a 1 mL vial at a concentration of 60 mg HCl salt to solvent. The material was heated to 100°X at a rate of 0.3° C./minute and then cooled to room temperature at the same rate. The visual contents were stirred at room temperature over the weekend. The solid was collected by filtration and dried at 50° C. under vacuum (50-100 torr).

Glycerol triacetate solvate: Triacetyl glycerol (0.2 mL) was added to solid from example 1, 19.5 mg. The slurry was mixed on a shaking block at 25° C. for 2 months. The solid was isolated by centrifugation on an ultra centrifuge at 1400 rpm using a 0.45 µm pore filter to give a white solid that was identified as the glycerol triacetate solvate.

Ethyl ether-ethanol-hydrate: Material from example 1 was dissolved in ethanol and the solvent removed under reduced pressure on a rotary evaporator to give amorphous material. The solid was dissolved in dichloromethane using a 4 mL vial and was placed inside a larger vial, 20 mL, containing diethyl ether. The small vial cap was removed and a cap placed on the larger vial. The solvents were allowed to diffuse into one another by vapor diffusion. Large crystals were obtained that were suitable for structure determination. The structure was solved and found to be the diethyl ether-ethanol-hydrate of compound of formula I.

Tert-Butyl methyl ether solvate: Tert-Butyl methyl ether, 5 mL, was added to solid from example 1, 26 mg. The slurry was heated to 50 C for 2 days on a shaking block and then allowed to stand at room temperature for 15 days. Sample was collected by filtering the suspension and analyzing the solid while the solid was still damp with solvent to give the tert-butyl methyl ether solvate of compound of formula I.

1,2-dimethoxyethane solvate: 1,2-Dimethoxyethane, 0.5 mL, was added to solid from example 1, 27 mg. The solid dissolved. The solution was filtered into a 4 mL vial and the cap removed. The vial was placed inside a 20 mL scintillation vial containing octane and the lid placed on the 20 mL vial. The vials were not disturbed. The solvents were allowed to diffuse into one another. Crystals suitable for structure determination were obtained. The crystal obtained contained 0.32 moles of 1,2-dimethoxyethane/mole of compound of formula I.

1,2-diethoxyethane solvate: 1,2-diethoxyethane, 5 mL, was added to solid from example 1, 21.9 mg. The slurry was heated to 50 C for 2 days on a shaking block and then allowed to stand at room temperature for 8 days. Sample was collected by filtering the suspension and analyzing the solid while the solid was still damp with solvent to give the 1,2-diethoxyethane of compound of formula I.

2,2-dimethoxypropane solvate: 2,2-dimethoxypropane, 5 mL, was added to solid from example 1, 30.5 mg. The slurry was heated to 50 C for 2 days on a shaking block and then allowed to stand at room temperature for 8 days. Sample was collected by filtering the suspension and analyzing the solid while the solid was still damp with solvent to give the 2,2-dimethoxypropane solvate of compound of formula I.

2-methyltetrahydrofuran solvate: 2-methyltetrahydrofuran, 3 mL, was added to solid from example 1, 92.2 mg. The slurry was heated to 50 C for 2 days on a shaking block and then allowed to stand at room temperature for 15 days. Sample was collected by filtering the suspension and analyzing the solid while the solid was still damp with solvent to give the 2-methyltetrahydrofuran solvate of compound of formula I.

The amounts of solvent present in solvates of a compound of formula I was analysed and is given below in Table 6.

TABLE 6

| Solvent | 1 molar equiv solvent % solvent | Single crystal solvent amount moles | Single crystal calculated weight % | Actual moles solvent experimental | Weight percent experimental |
|---|---|---|---|---|---|
| Toluene | 15.7 | 0.64 | 10.7 | 0.24 | 4.3 |
| Chlorobenzene | 18.5 | — | — | | |
| Ethylbenzene | 17.7 | — | — | 0.47 | 9.2% |
| o-xylene | 17.7 | | | — | — |
| m-xylene | 17.7 | | | 0.32 | 6.4 |
| p-xylene | 17.7 | | | 0.42 | 8.3 |
| cumene | 19.5 | | | 0.34 | 7.6 |
| tetralin | 21.1 | | | | |
| MEK | 12.7 | | | | |
| MIBK | 16.8 ½ molar 9.2% | 0.14 | 2.8 | 0.35 | 6.6 |
| MBK | 16.8 ½ molar 9.2% | | | 0.54 | 9.9 |
| DIBK | 22.3 ½ molar equiv 12.6 | | | 0.38 | 9.9 |
| Chloroform | 1.5 molar equivalents | 1 + ¼ water | | | |
| MeOAc | 13.0 | 0.71 | 9.6 | 0.5 | 7.0 |
| PrOAc | 17.1 | 0.33 | 6.4 | | |
| iBuOAc | 19.0 | | | 0.36 | 7.8 |
| tBuOAc | 19.0 | | | 0.39 | 8.4 |
| AmylOAc | 20.8 | | | 0.41 | 9.7-9.8 |
| glycerol triacetate | 30.6 0.5 molae equiv 18.08 | | | 0.26 | 10.3 |
| TBME | 15.1 | | | | |
| DME | 15.4 | 0.32 | 5.5 | | |
| DEE | 19.3 | | | 0.37 | 7.3 |
| DMP | 17.4 | | | 0.37 | 7.3 |
| MeTHF | 14.8 | | | 0.43 | 6.9 |

ADDITIONAL EMBODIMENTS

Embodiment 1

A pharmaceutical formulation comprising amorphous (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride.

Embodiment 2

The formulation of embodiment 1, further comprising antioxidant.

Embodiment 3

The formulation of embodiment 2, wherein the antioxidant is BHA or BHT.

Embodiment 4

The formulation of embodiment 1, wherein the formulation is liquid fill capsule for oral delivery.

Embodiment 5

The formulation of embodiment 4, further comprising a liquid fill solvent selected from propylene glycol monocaprylate, PEG-32 glyceryl laurate, PEG-6 glyceryl oleate, PEG-6 glyceryl linoleate, Propylene glycol monolaurate, Poloxamer 188, Poloxamer 407, Polyethyleneglycol 1500, Propylene glycol, Glycerol (Glycerin), d-alpha tocopheryl PEG-1000 succinate and PEG-8 caprylic/capric glycerides.

Embodiment 6

The formulation of embodiment 5, comprising 100 to 400 mg of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one.

Embodiment 7

The formulation of embodiment 1, comprising (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride, liquid fill solvent selected from capryol 90 and lauroglycol 90 and antioxidant selected from BHT or BHA.

Embodiment 8

The formulation of embodiment 1, wherein the formulation is a tablet for oral delivery.

Embodiment 9

The formulation of embodiment 8, further comprising polyvinylpyrolidone.

Embodiment 10

The formulation of embodiment 9, further comprising anhydrous silicon dioxide (precipitated silica/fumed silica/amorphous silica) and microcrystalline cellulose.

Embodiment 11

The formulation of embodiment 9, further comprising colloidal silicon dioxide (fumed silica) and microcrystalline cellulose.

Embodiment 12

The formulation of embodiment 10, further comprising antioxidant selected from BHA and BHT or Propyl gallate.

Embodiment 13

The formulation of embodiment 11, comprising 100 to 400 mg of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one.

Embodiment 14

The formulation of embodiment 1, comprising amorphous (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride, Polyvinyl pyrolidone, Butylated hydroxyl anisole, Croscarmellose sodium, Fumed silica, Microcrystalline cellulose and Stearic acid.

Embodiment 15

A crystalline (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride propylene glycol monocaprylate solvate.

Embodiment 16

A crystalline (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride propylene glycol monolaurate solvate.

What is claimed is:

1. A crystalline form of (S)-2-(4-chlorophenyl)-1-(4-((5R, 7R)-7-hydroxy-5-methyl-6,7-dihydro-5H-cyclopenta[d]pyrimidin-4-yl)piperazin-1-yl)-3-(isopropylamino)propan-1-one monohydrochloride having X-ray diffraction pattern that includes a characteristic peak at about 7.1.

2. The crystalline form of claim 1, further comprising one or more characteristic peaks selected from 8.4, 8.8, 10.5, 12.7, 13.7, 13.9, 17.4, 21.1 and 22.3.

3. A liquid fill capsule comprising (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino) propan-1-one monohydrochloride and a solvent selected from mono-esters, di-esters, tri-esters and combinations thereof, of fatty acids ($C_{3-20}$ alkyl or $C_{8-18}$ alkyl) and glycerol, ethylene glycol, propylene glycol or polyethylene glycol.

4. The capsule of claim 3, wherein the solvent is selected from glyceryl stearate, esters of natural fatty, stearic and palmitic acids with glycerin, alkylglycol caprylates, propylene glycol monocaprylate, polyethyleneglycol glyceryl laurate, polyethyleneglycol glyceryl oleate, polyethyleneglycol glyceryl linoleate, propylene glycol monolaurate, poloxamer, polyethyleneglycol, propylene glycol, glycerol, d-alpha tocopheryl polyethyleneglycol succinate, polyethyleneglycol caprylic or capric glyceride, and esters of caprylic or capric fatty acids with glycerin or propylene glycol.

5. The capsule of claim 3, wherein the solvent is propylene glycol caprylate or propylene glycol monolaurate.

6. A crystalline composition comprising (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride and solvent selected from the group consisting of capryol glycol, lauryl glycol, MEK, MIBK, MTBK, chloroform, dichloromethane, ethyl acetate, toluene, chlorobenzene, ethylbenzene, THF, 2-methylTHF, 1,2-dichloroethane, ortho-xylene, meta-xylene, para-xylene, anisole, methyl acetate, cumene, tetralin, propyl acetate, isopropyl acetate, diisobutyl ketone, isobutyl acetate, t-butyl acetate, amyl acetate, glycerol triacetate, 1,2-dimethoxyethane, 1,2-diethoxyethane, 2,2-dimethoxypropane, ethyl ether, t-butyl methyl ether, water and mixtures thereof.

7. The composition of claim 6, further comprising said solvent solvated to said (S)-2-(4-chlorophenyl)-1-(4-((5R, 7R)-7-hydroxy-5-methyl-6,7-dihydro-5H-cyclopenta[d]pyrimidin-4-yl)piperazin-1-yl)-3-(isopropylamino)propan-1-one monohydrochloride.

8. The composition of claim 7, further comprising said (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride solvated in a 1:1 molar ratio with said solvent.

9. The composition of claim 7, further comprising said (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride solvated in a w/w % (solvent:compound) in the range of about 0.1% to about 20%.

10. Mesomorphous (S)-2-(4-chlorophenyl)-1-(4-((5R, 7R)-7-hydroxy-5-methyl-6,7-dihydro-5H-cyclopenta[d]pyrimidin-4-yl)piperazin-1-yl)-3-(isopropylamino)propan-1-one monohydrochloride.

11. A process of producing mesomorphous (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride, comprising contacting (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride with a solvent comprising antisolvent, and removing said solvent.

12. The process of claim 11, wherein said solvent has solubility greater than about 20 mg/mL for (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride.

13. The process of claim 12, wherein said solvent comprises water, ethyl acetate, methanol, ethanol, isopropanol, 2-butanol, t-butanol and 2-methoxy ethanol, tetrahydrofuran, 2-methyltetrahydrofuran, toluene, chloroform, dichloromethane, 1,2-dichloroethane or acetone.

14. The process of claim 12, wherein said solvent comprises ethyl acetate.

15. The process of claim 14, wherein said solvent comprises ethyl acetate:isopropanol in 1:1 mixture.

16. The process of claim 11, wherein said antisolvent has solubility less than about 20 mg/mL for (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride.

17. The process of claim 16, wherein said antisolvent comprises pentane, hexane, cyclohexane, heptane, ethyl acetate, iso-propyl acetate, methyl t-butyl ether (MTBE) or methyl iso-butyl ketone.

* * * * *